United States Patent
Wang et al.

(10) Patent No.: US 9,090,915 B2
(45) Date of Patent: Jul. 28, 2015

(54) SULFITE PRETREATMENT FOR BIOREFINING BIOMASS

(75) Inventors: Gaosheng Wang, TianJin (CN); Xuejun Pan, Fitchburg, WI (US); Jun Yong Zhu, Madison, WI (US); Roland L. Gleisner, Jefferson, WI (US)

(73) Assignees: Wisconsin Alumni Research Foundation, Madison, WI (US); The United States of America as represented by the Secretary of Agriculture, Washington, DC (US)

( * ) Notice: Subject to any disclaimer, the term of this patent is extended or adjusted under 35 U.S.C. 154(b) by 729 days.

(21) Appl. No.: 12/425,773

(22) Filed: Apr. 17, 2009

(65) Prior Publication Data

US 2009/0298149 A1     Dec. 3, 2009

Related U.S. Application Data

(60) Provisional application No. 61/047,024, filed on Apr. 22, 2008.

(51) Int. Cl.
| | |
|---|---|
| *C12P 7/10* | (2006.01) |
| *C07G 1/00* | (2011.01) |
| *C08H 8/00* | (2010.01) |
| *C08L 97/02* | (2006.01) |
| *C10L 1/02* | (2006.01) |
| *C13K 1/02* | (2006.01) |
| *D21C 5/02* | (2006.01) |

(52) U.S. Cl.
CPC ... *C12P 7/10* (2013.01); *C07G 1/00* (2013.01); *C08H 8/00* (2013.01); *C08L 97/02* (2013.01); *C10L 1/023* (2013.01); *C13K 1/02* (2013.01); *D21C 5/022* (2013.01); *Y02E 50/16* (2013.01)

(58) Field of Classification Search
CPC ............ C07G 1/00; C08H 8/00; C08L 97/02; C12P 7/10; C13K 1/02; D21C 5/022; C10L 1/023; Y02E 50/16
See application file for complete search history.

(56) References Cited

U.S. PATENT DOCUMENTS

| | | | | |
|---|---|---|---|---|
| 2,269,985 | A * | 1/1942 | Olsen | 162/79 |
| 2,924,547 | A | 2/1960 | Knapp et al. | 162/83 |
| 3,652,387 | A * | 3/1972 | Wilder | 162/25 |
| 3,808,090 | A | 4/1974 | Logan et al. | 162/23 |
| 3,998,688 | A | 12/1976 | Fischer et al. | 162/50 |
| 3,998,845 | A * | 12/1976 | Goldstein et al. | 549/87 |
| 4,017,642 | A * | 4/1977 | Orth et al. | 426/69 |
| 4,089,745 | A * | 5/1978 | Antrim et al. | 435/99 |
| 4,211,605 | A * | 7/1980 | Saxton et al. | 162/64 |
| 4,326,032 | A * | 4/1982 | Grove | 435/148 |
| 4,767,499 | A | 8/1988 | Simonson et al. | 162/25 |
| 5,004,523 | A * | 4/1991 | Springer et al. | 162/76 |
| 5,205,496 | A * | 4/1993 | O'Donnell et al. | 241/34 |
| 5,540,392 | A * | 7/1996 | Broderick et al. | 241/28 |
| 5,597,714 | A | 1/1997 | Farone et al. | 435/100 |
| 5,676,795 | A * | 10/1997 | Wizani et al. | 162/30.11 |
| 6,017,870 | A * | 1/2000 | Bower et al. | 510/392 |
| 6,027,610 | A * | 2/2000 | Back et al. | 162/111 |
| 6,555,350 | B2 | 4/2003 | Ahring et al. | 435/162 |
| 7,182,836 | B2 | 2/2007 | Patt et al. | 162/90 |
| 2002/0026991 | A1 * | 3/2002 | Stromberg et al. | 162/19 |
| 2003/0098272 | A1 * | 5/2003 | Marsh et al. | 210/321.74 |
| 2005/0207971 | A1 * | 9/2005 | Cortright et al. | 423/657 |
| 2009/0229771 | A1 * | 9/2009 | Warnes et al. | 162/28 |

FOREIGN PATENT DOCUMENTS

EP            105937 A1 *  4/1984

OTHER PUBLICATIONS

Lindgren, B. Acta Chemica Scandinavica (1951) 5: 603-615.*
Chen et al. Biomass and Bioenergy (2005) 28: 411-417.*
Ohgren et al. Applied Biochem. Biotechnol. (2005) 121-124: 10551067.*
Ooshima et al. Biotecnol. Bioeng. (1986) vol. XXVIII: 1727-34.*
Yean et al. Pulp and Paper Magazine of Canada (1957) 58(7): 197-210.*
Allen et al., "A comparison of aqueous and dilute-acid single-temperature pretreatment of yellow of poplar sawdust," *Ind. Eng. Chem. Res.*, 40:2352-2361, 2001.
Ballesteros et al., "Effect of chip size on steam explosion pretreatment of softwood," *Applied Biochem. Biotechnol.*, 84-86:97-110, 2000.
Cadoche and López, "Assessment of size reduction as a preliminary step in the production of ethanol from lignocellulosic wastes," *Biological Wastes*, 30:153-157, 1989.
Chum et al., "Pretreatment-catalyst effects of the combined severity parameter," *Appl. Biochem. Biotechnol.*, 24-25:1-14, 1990.
Chundawat et al., "Effect of particle size based separation of milled corn stover on AFEX pretreatment and enzymatic digestibility," *Biotechnol. Bioengineer.*, 85:219-231, 2007.
Cullis et al., "Effect of initial moisture content and chip size on the bioconversion efficiency of softwood lignocellulosics," *Biotechnol. Bioengineer.*, 85:413-421, 2004.
Dasari and Berson, "The effect of particle size on hydrolysis reaction rates and rheological properties in cellulosic slurries," *Applied Biochem. Biotech.*, 137:289-299, 2007.
De Bari et al., "$SO_2$-catalyzed steam fractionation of aspen chips for bioethanol production: optimization of the catalyst impregnation," *Ind. Eng. Chem. Res.*, 46:7711-7720, 2007.
Eggeman and Elander, "Process and economic analysis of pretreatment technologies," *Bioresour. Technol.*, 96:2019-2025, 2005.
Excoffier et al., "Saccharification of steam-exploded poplar wood," *Biotechnol. Bioeng.*, 38:1308-1317, 1991.

(Continued)

*Primary Examiner* — Susan Hanley
(74) *Attorney, Agent, or Firm* — Parker Highlander PLLC

(57) ABSTRACT

The present invention relates to a method using sulfite pretreatment to overcome recalcitrance of lignocellulose (SPORL). More specifically, it relates to a sulfite-based chemical process for pretreating biomass in solutions to reduce access barriers of enzymes to the lignocellulose, resulting in efficient conversion through enzymatic saccharification.

11 Claims, 39 Drawing Sheets

(56) References Cited

OTHER PUBLICATIONS

Galbe and Zacchi, "A review of the production of ethanol from softwood," *Appl. Microbiol. Biotech.*, 59:618-628, 2002.

Guy et al., In: *Comparison of fiber length analyzers*, Proc. 2005 TAPPI Papermarkers Conf., Milwaukee, WI, 2005.

Heitz et al., "Fractionation of Populas tremuloides at the pilot scale: optimization of steam explosion pretreatment conditions using the STAKE II technology," *Bioresour. Technol.*, 35:23-32, 1991.

Himmel et al., "Biomass recalcitrance: engineering plants and enzymes for biofuels production," *Science*, 315:804-807, 2007.

Holtzapple et al., "Energy requirements for the size reduction of poplar and aspen wood," *Biotech. Bioeng.*, 33:207-210, 1989.

Hoque et al., In: *Review and anlysis of performance and productivity of size equipment for fibrous materials*, ASABE Annual International Meeting, Minneappolis, MN, 2007.

Jeoh et al., "Cellulase digestibility of pretreated biomass is limited by cellulose accessibility," *Biotechnol. Bioeng.*, 98:112-122, 2007.

Kenealy et al., "Vapor phase diethyl oxalate pretreatment of wood chips: Part 1, energy saving and improved pulps," *Holzforschung*, 61:223-229, 2007.

Larsson et al., "The generation of fermentation inhibitors during dilute acid hydrolysis of softwood," *Enzyme Microbial. Tech.*, 24:151-159, 1999.

Laureano-Perez et al., "Understanding factors that limit enzymatic hydrolysis of biomass: characterization of pretreated corn stover," *Appl. Biochem. Biotech.*, 121-124:1081-1099, 2005.

Lynd, "Overview and evaluation of fuel ethanol from cellulosic biomass: technology, economics, the environment, and policy," *Annu. Rev. Energy and the Environment*, 21:403-465, 1996.

Mabee et al., "Updates on softwood-to-ethanol process development," *Appl. Biochem. Biotech.*, 129-132:55-70, 2006.

Mani et al., "Grinding performance and physical properties of wheat and barley straws, corn stover and switchgrass," *Biomass. and Bioenergy*, 27:339-352, 2004.

Mansfield et al., "Substrate and enzyme characterization that limit cellulose hydrolysis," *Biotech. Progress*, 15:804-816, 1999.

Mooney et al., "The effect of fiber characteristics on hydrolysis and cellulase accessibility to softwood substrates," *Enzyme and Microbial. Technol.*, 25:644-650, 1999.

Mosier et al., "Features of promising technologies for pretreatment of lignocellulosic biomass," *Bioresour. Tech.*, 96:673-686, 2005.

Nguyen et al., "Two-stage dilute-acid pretreatment of softwoods," *Appl. Biochem. Biotech.*, 84-86:561-576, 2000.

Pan et al., "Biorefining of softwoods using ethanol organosolv pulping: preliminary evaluation of process streams for manufacture of fuel-grade ethanol and co-products," *Biotech. Bioengin.*, 90:473-481, 2005.

Pan et al., "Bioconversion of hybrid poplar to ethanol and co-products using an organosolv fractionation process: optimization of process yields," *Biotech. Bioengin.*, 94:851-861, 2006.

Reinke, "A new multiple-unit constant-pressure micro-respirometer," *J. Appl. Physiol.*, 16:944-946, 1961.

Rivers and Emert, "Lignocellulose pretreatment: a comparison of wet and dry ball attrition," *Biotechnology Letters*, 9:365-8, 1987.

Sangseethong et al., "Rationale for particular size effect on rates enzymatic saccharification of microcrystalline cellulose," *J. Food. Biochem.*, 22:321-330, 1998.

Schell and Harwood, "Milling of lignocellulosic biomass: results of pilot scale testing," *Appl. Biochem. Biotech.*, 45/46:159-168, 1994.

Stenberg et al., "Effect of substrate and cellulase concentration on simultaneous saccharification and fermentation of steam-pretreated softwood for ethanol production," *Biotechnol. Bioeng.*, 68:204-10, 2000.

Sun and Cheng, "Hydrolysis of lignocellulosic materials for ethanol production: a review," *Bioresource Technol.*, 83:1-11, 2002.

Tillman et al., "Effect of transient variation of temperature on acid hydrolysis of aspen hemicellulose," *Applied Biochem. Biotechnol.*, 20-21:107-117, 1989.

Tillman et al., "Effect of transient acid diffusion on pretreatment/hydrolysis of hardwood hemicellulose," *Applied Biochem. Biotechnol.*, 24-25:103-113, 1990.

Wingren et al., "Techno-economic evaluation of producing ethanol from softwood: comparison of SSF and SHF and identification of bottlenecks," *Biotechnol. Prog.*, 19:1109-1117, 2003.

Yang and Wyman, "Effect of xylan and lignin removal by batch and flowthrough pretreatment on the enzymatic digestibility of corn stover cellulose," *Biotech. Bioengin.*, 86:88-95, 2004.

Zhao et al., "Enhanced enzymatic hydrolysis of spruce by alkaline pretreatment at low temperature," *Biotechnol. Bioengin.*, 99:1320-1328, 2008.

Zhu et al., "Effects of plantation density on wood density anatomical properties of red pine (*Pinus resinosa* ait)," *Wood and Fiber Sci.*, 39:502-512, 2007.

Zhu et al., "Optimization of dilute-acid pretreatment of corn stover using a high-solids percolation reactor," *Biochem. Biotech.*, 121-124:1045-1054, 2005.

Zhu et al., "Specific surface to evaluate the efficiencies of milling and pretreatment of wood enzymatic saccharification," *Chem. Eng. Sci.*, 64:474-485, 2009.

Zhu et al., "Sulfite pretreatment (SPORL) for robust enzymatic saccharification of spruce and red pine," *Bioresource Technology*, 100:2411-2418, 2009.

\* cited by examiner

FIGS. 6A-D

US 9,090,915 B2

SULFITE PRETREATMENT FOR BIOREFINING BIOMASS

PRIORITY CLAIM

The present application claims benefit of priority to U.S. Provisional Application Ser. No. 61/047,024, filed Apr. 22, 2008, the entire contents of which are hereby incorporated by reference.

FEDERAL FUNDING

This invention was made with government support under USDA/FS 07-JV-11111122-012 awarded by United States Department of Agriculture. The government has certain rights in the invention.

BACKGROUND OF THE INVENTION

I. Field of the Invention

The present invention relates generally to the field of biomass biorefining. More particularly, it concerns sulfite pretreatment processes to overcome recalcitrance of lignocellulose for robust conversion of biomass (SPORL) and processes to reduce energy consumption by optimizing solids-loading and size reduction.

II. Description of Related Art

Biofuel and biochemicals, such as cellulosic ethanol, have a wide use, including as an alternative liquid fuel and commodity products. If the ethanol and chemical production process only uses energy and materials from renewable sources, no net carbon dioxide is added to the atmosphere, and therefore environmental friendly. Biological conversion, such as fermentation, of biomass to ethanol is an attractive route to energy feedstocks that supplements the depleting stores of fossil fuels. Biomass is a carbon-neutral source of energy, since it comes from dead plants, which means that the combustion of ethanol produced from lignocelluloses will produce no net carbon dioxide in the earth's atmosphere. Also, biomass is readily available, and the fermentation of lignocelluloses provides an attractive way to dispose of many industrial and agricultural waste products. Finally, lignocellulosic biomass is a very renewable resource. Many of the dedicated energy crops can provide high energy biomass, which may be harvested multiple times each year.

One barrier to the production of fuel such as ethanol and chemicals from biomass is that the sugars necessary for chemical and biological conversion, such as fermentation are trapped inside the lignocellulose, a combination of lignin, hemicellulose and cellulose that strengthens biomass plant cells. Lignocellulose has evolved to resist degradation and to confer hydrolytic stability and structural robustness to the cell walls of the plants. In addition to the physical barrier of lignin, this robustness or "recalcitrance" is partially attributable to the crosslinking between the polysaccharides (cellulose and hemicellulose) and the lignin via ester and ether linkages. Ester linkages arise between oxidized sugars, the uronic acids, and the phenols and phenylpropanols functionalities of the lignin. To extract the fermentable sugars, one may need to first disconnect the celluloses from the lignin, and then acid- or enzyme-hydrolyze the newly freed celluloses to break them down into simple monosaccharides. Another challenge to biomass fermentation is the high percentage of pentoses in the hemicellulose, such as xylose, or wood sugar. Unlike hexoses, such as glucose, pentoses are difficult to ferment. The problems presented by the lignin and hemicellulose fractions are the foci of much contemporary research.

Thus, the key impediment in cellulose bioconversion is the physical and chemical barriers posed by plant cell walls that limit hydrolytic enzymes access to the biomass macrostructure (cellulose) (Eggeman and Elander, 2005; Sun and Cheng, 2002; Jeoh et al., 2007). Extensive research efforts have been devoted to various chemical pretreatments of biomass to overcome the barriers and to enhance enzyme accessibility to cellulose, by removing chemical components of biomass (lignin and/or hemicellulose). Alkaline, dilute acid, hot water, ammonia, organosolv pretreatment technologies have been developed (Mosier et al., 2005; Pan et al., 2005) with some level of success.

However, there are four major pitfalls of almost all existing chemical pretreatment processes. First, significant reduction in biomass feedstock size from chip or chop to particle of one millimeter or less (fiber or powder), is required (except for organosolv process) before chemical pretreatment can effectively remove barriers of enzyme access to cellulose to get satisfactory cellulose bioconversion efficiencies over 90%. The size reduction of biomass feedstock consumes a significant amount of electrical-mechanical or thermal energy. The size reduction is particularly critical to woody biomass because of the large native physical size and the strong integrity of wood that requires significant energy inputs to disintegrate logs into small particles. About 200-400 Watt hours (Wh) electric-mechanical energy in disk or hammer milling of one kilogram (kg) oven-dry woody biomass (Schell and Harwood, 1994; Reineke, 1961) is required, which is equivalent to 30-65% of the wood ethanol energy assuming thermal to electrical energy conversion efficiency of 30%.

The second pitfall of the existing pretreatment processes is that the enzymatic hydrolysis cellulose conversion efficiency of softwood is less than 70% (Galbe and Zacchi 2002). However, forestry is a significant source of renewable biomass feedstock for biorefining and softwood is the major woody biomass in several parts of the U.S., such as inner Pacific Northwest and Southeast, and in Canada as well as Scandinavian countries. Most forest biomass from the U.S. National Forest is mixed softwood. Efficient technologies for pretreatment of softwood for biorefining are highly desired.

The third pitfall is the limited digestibility of the substrates pretreated using the existing pretreatment processes. The slow rate of saccharification limits the productivity and yield of the bioconversion. It also requires increased enzyme loading to achieve a satisfactory cellulose-to-glucose yield. The low yield and increased enzyme dosage are two major factors that affect the economics of cellulosic ethanol and other bio-based products (Hinman et al. 1992).

The fourth is the barrier to commercialization. There is no mature equipment and technologies available for most of the existing pretreatment methods, such as reactors or extractors for steam explosion or organosolv pretreatments, and therefore capital-intensive research and development is required.

In view of these pitfalls, a practical and viable pretreatment process for conversion, such as biomass bioconversion, remains to be developed. This is especially true for woody biomass, in particular softwood, despite much research progress having been made in biomass pretreatment for bioconversion in the last several decades.

SUMMARY OF THE INVENTION

Thus, in accordance with certain aspects of the present invention, there is provided a method for treating a cellulose-containing material comprising the steps of (a) providing a material comprising cellulose; and (b) treating the material in an aqueous solution comprising sulfite or bisulfate, wherein said treating is at a pH ranging from about 0 to about 10, particularly about 1.5 to about 5.0, more particularly in a range of about 1.5-4.5 or about 1.5 to 4.0, even more particularly at 1.8 to about 3.5 or 1.8 to about 2.5, at a temperature between about 130-250° C., more particularly between about 150-220° C., 160-190° C., or 170-180° C., and specifically at about 180° C. In an embodiment, the step (b) may comprise a period of 0.1 to about 120 min, more particularly in a range of 0.5 to about 30 min, depending on the size reduction process used. Generally, higher temperatures permit shorter times of treating. Step (b) can also be carried by steaming the materials preimpregnated with the aqueous treatment solution described below with or without steam explosion.

In certain aspects, this method may further comprise adjusting pH with a reagent. The regent in this regard may be sulfur dioxide, sulfurous acid, sulfuric acid, hydrochloric acid, oxalate acid, or acetic acid or any reagent known to be capable of adjusting pH and compatible with the efficacy of the sulfite or bisulfite in the above method. Particularly, sulfuric acid may be used for convenience.

In some aspects, the sulfite or bisulfite may further comprise sulfur dioxide. For example, the mass ratio between the sulfite or bisulfite and the material is in the range of 1:500 to 1:5 depending on the feedstock used, more particularly at about 1:400 to 1:5, about 1:100 to 1:10, or about 1:40 to 1:10, and most particularly at about 1:40 to about 1:10 or about 1:15 to about 1:10 for softwood, at about 1:100 to about 1:20 or about 1:40 to about 1:15 for hardwood, agriculture residues, waste paper, etc. Exemplary bisulfite include, but are not limited to, sodium bisulfite, magnesium bisulfite, ammonia bisulfite, calcium bisulfite, or potassium bisulfite or any bisulfite salt not interfering with the treating method or process.

In certain embodiments, the material can be in the order of millimeters in its smallest dimension (e.g., 100 nm, 500 nm, 1 mm, 2 mm, 3 mm, 4 mm, 5 mm, 6 mm, 7 mm, 8 mm, 9 mm, 1 cm). The material may comprise softwood, hardwood, herbaceous plants or other biomass feedstock. Specific examples of softwood include fir (e.g., Douglas fir, Grand fir, White fir), spruce and pine (e.g., red pine, Southern pine, Lodgepole pine or Jack Pine). Hardwood may comprise Maple, Birch, Oak, Ash, Eucalyptus, Aspen or Poplar in particular. The herbaceous plants may comprise agriculture residue (e.g., wheat straw, rice straw, herbage, corn stover) and energy crops (e.g., switchgrass). And the other biomass feedstocks may comprise saw dust or waste paper.

Optionally, but not necessarily, the method may further comprise impregnating the material with the aqueous pretreatment solution before step (b) at a temperature range of about 0-130° C., more particularly about 20-90° C. or 25-90° C. for 0.001-500 hours depending on the temperature of impregnation. Combining impregnation with steam pretreatment (without explosion) of the preimpregnated wood chips may save thermal energy consumption in pretreatment. In a further embodiment, the method may further comprise a mechanical size reduction step, such as disk milling or hammer milling, before or after step (b). In a still further embodiment, step (b) could take place in a feeder coupled to a device used for the mechanical size reduction step. Moreover, the method may further comprise a steam explosion step at the same time as step (b) for effective pretreatment for later cellulose conversion. The method may further comprise enzymatic hydrolysis and fermentation, or simultaneous saccharification and fermentation (SSF), of the material after step (b) to convert cellulose into ethanol, and the enzymatic hydrolysis may further comprise adding a surfactant, e.g., PEG (polyethylene glycol), to increase conversion efficiency.

The method may further comprise chemical conversions of cellulose and hemicellulose sugars to valuable other form of biofuels and biochemicals.

The invention is also directed in certain aspects to a product comprising ethanol, biofuel, biochemicals, or bioproducts produced by the method in accordance with above embodiments.

"SPORL" as used herein, refers to a process using Sulfite Pretreatment to Overcome Recalcitrance of Lignocellulose for robust conversion of biomass through enzymatic saccharification, it not only includes sulfite pretreatment for altering the biomass chemical structure, but also including the thermal/mechanical treatment for biomass size reduction.

The terms sulfite and bisulfite are used interchangeably in the present invention because the active reagents in the pretreatment liquor can be sulfite ($SO_3^{-2}$), bisulfite ($HSO_3^{-1}$), or the combination of sulfite ($SO_3^{-2}$) or bisulfite ($HSO_3^{-1}$) with sulfur dioxide ($SO_2$)/sulfurous acid ($H_2SO_3$) or any other acids depending on the pH of the pretreatment liquor at pretreatment temperatures (Ingruber, 1985).

In accordance with certain aspects of the present invention, there also is provided a method to significantly reduce energy consumption (by a factor of 10 or more) for size-reduction of biomass feedstock to produce enzyme digestible substrates in the form of particles, fibers, fiber bundles. The method is particularly suitable for feedstock with strong physical integrity, such as wood, forest biomass, bamboo, giant reed, wood crops, etc. The method may comprise (1) conducting size-reduction of feedstock after chemical or biological pretreatments; (2) using low solids-loading in milling, such as disk milling solids-loading between 0.1% to 50%, even more particularly between 1% to 35%. Solids-loading is defined as the percentage of oven dry mass of biomass feedstock of the total wet mass feed into the size-reduction; (3) reducing milling intensity, such as through increasing milling disk plate gap, greater than 0.005 mm. The maximum disk plate gap depends on the physical dimension of the feedstock and the desired enzymatic cellulose conversion efficiency. When wood chips are used, the maximum disk plate gap can be as large as the maximum size of the wood chips, for example for pulp mill wood chips of maximum dimension of about 50 mm, the maximum disk plate gap is about 50 mm, but preferably between 0.2 mm to 20 mm. Enzymatic cellulose conversion are not affected by using low solids-loadings with proper chemical pretreatment, such as SPORL as discussed in the preceding paragraphs.

In certain aspects of the present invention, there is provided a method to characterize the size of the biomass substrate using wet imaging. The wet imaging is comprised of a flow channel in which biomass substrate suspension can flow through, a camera to capture the image of each particle of the substrate. The present invention may also provide various models for the particle/fiber/fiber bundle to calculate the substrate mean specific surface and specific surface distribution from the imaging data. The cylindrical model is preferred for simplification.

In certain aspect of the present invention, there is provided a method to realize in-situ control of size-reduction process by using the measured substrate specific surface, size, and energy consumption in size-reduction. Maximum enzymatic cellulose conversion of the feedstock with minimal energy consumption in size-reduction can be achieved through this type of process control.

Other embodiments of the invention are discussed throughout this application. Any embodiment discussed with respect to one aspect of the invention applies to other aspects of the invention as well and vice versa. The embodiments in the Example section are understood to be embodiments of the invention that are applicable to all aspects of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

I. The Present Invention

Figure 1:
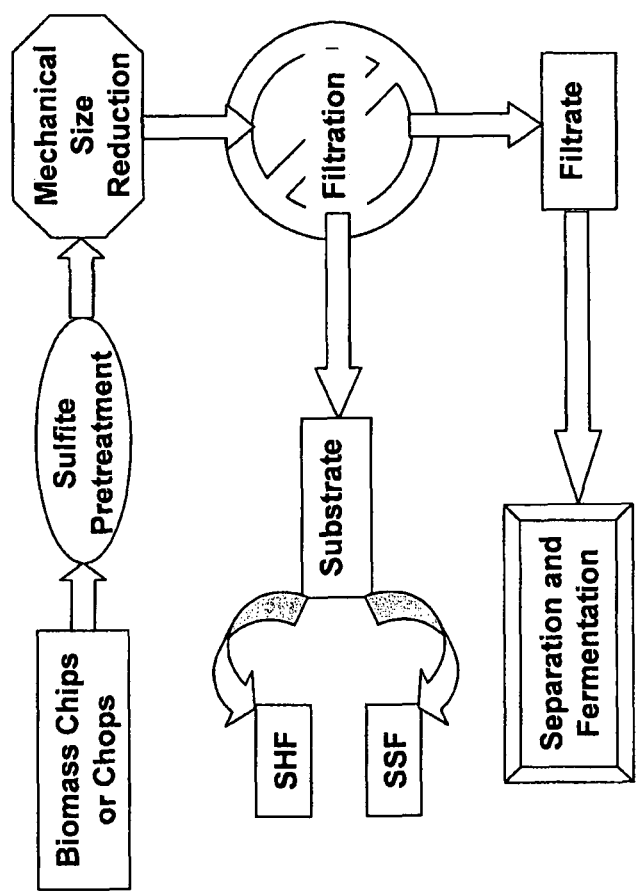
FIG. 1. An exemplary embodiment of SPORL process flow.

It is believed that a commercially viable biomass conversion process needs to simultaneously meet the requirements of the high cellulose conversion within a short time (such as within two days) of enzymatic hydrolysis and low size reduction energy consumption. In a particular embodiment, the process would meet 90% cellulose bioconversion efficiency with 90 Wh/kg (oven-dry biomass) size reduction energy consumption, i.e., a target of 90/90. For most biomass resources, good cellulose bioconversion efficiency has been achieved when pretreatment was applied to significantly size reduced biomass feedstock at the expense of consuming significant electric-mechanical energy (Allen et al. 2001; Zhu et al. 2005; Nguyen et al. 2000). As a result of the approach of size reduction prior to pretreatment, the 90 Wh/kg energy consumption target in size reduction was not achieved for any woody even some nonwoody biomass. Most literature work did not report the energy consumption in size reduction and simply focused on achieving 90% cellulose bioconversion efficiency by using biomass substrates with very small unknown sizes or energy consumptions. Therefore, data on cellulose bioconversion have limited practical value. To achieve the 90 Wh/kg energy consumption target for size reduction, there is a need to develop a pretreatment process that can effectively treat chip or chop form of biomass prior to further size reduction without sacrificing cellulose bioconversion efficiency. The new pretreatment is expected to alter the biomass structure, helping to reduce the energy consumption for size reduction in subsequent milling of pretreated chips or chops.

Thus, in accordance with certain embodiments of this invention, there is provided a process using Sulfite Pretreatment to Overcome Recalcitrance of Lignocellulose (SPORL) for robust conversion of biomass through enzymatic saccharification. SPORL can be effective in directly pretreating chip or chop size biomass without further size reduction and chip impregnation. Embodiments of the invention establish SPORL operating conditions that can significantly alter the chemical and physical structure of biomass, allowing it to be easily digested in enzymatic saccharification with cellulose conversion efficiency of above 90% in a very short period of time and low enzyme application dosage. The pretreatment may also help to reduce mechanical energy consumption during size reduction of chip or chop biomass in the subsequent process. Certain aspects of the present invention was demonstrated over a range of operating conditions, such as chemical dosage, acid (pH), etc., using softwood, hardwood, agriculture residuals and waste paper. The present invention may be able to achieve over 90% cellulose conversion efficiency for softwood, which has never been reported by using of other existing processes except the organosolv process.

Certain aspects of this invention also establish processes using chemical/biological/thermal pretreatment and mechanical size-reduction techniques to significantly reduce energy consumption in biomass size-reduction. Specifically, this invention establishes a post-chemical/biological/thermal pretreatment size-reduction approach and several key process conditions to low size-reduction energy consumption. The invention also establishes a procedure to characterize substrate size for conversion to monitor size reduction and achieve optimal size for biofuel production.

II. Sulfite Chemistry in Wood Pulping

Sulfite pulping has been used as a pulping process to produce chemical pulps for more than a century. It was the dominant pulping process in early part of the last century due to its high yield, low cost of cooking chemicals, and high brightness of the unbleached pulps. However, sulfite pulping has been gradually replaced by Kraft pulping since 1940's mainly because the performance of sulfite process is wood species-dependent and the pulp strength was distinctively weaker than that of Kraft pulp. Only a few sulfite pulp mills are in production today.

Sulfite pulping operates in a wide range of pH and temperature, which is well described in textbooks (Bryce, 1980). Acid sulfite pulping has a high excess of free sulfur dioxide with typical pulping liquor pH around 1.5. Bisulfite pulping operates in the pH range of 3-5. Alkaline sulfite pulping uses a combination of sulfite and hydroxide as pulping chemicals operating in a pH in range of 10-13.

The goal of pulping is to remove as much lignin as possible without the concurrent loss and degradation of hemicellulose and cellulose, leading to a pulp with high yield and strength. To achieve this goal, proper temperature control is very important in sulfite pulping. In order to avoid lignin condensation, acid sulfite pulping (pH ~1.5) often uses slowly increasing temperatures to a final pulping temperature of around 130° C., which is held for several hours or more. Maximum pulping temperature never exceeds 150° C. Bisulfite pulping (with pH 3-5) is not limited by heating rate but maximum pulping temperature is controlled in a range of 160-166° C. It is understood that a decrease in maximum pulping temperature can produce pulp with high hemicellulose content, less cellulose degradation, and high yield for both the acid sulfite and the bisulfite pulping processes (Hall and Stockman 1958; Yorston 1942). Over the years, alkaline sulfite pulping gradually dominated and displaced acid sulfite and bisulfite pulping for its rapid pulping rate and versatility in pulping various wood species.

Sulfite has also been used for pretreating wood chips for the production of chemi-thermo-mechanical pulps (CTMP), semi-chemical pulps (SCP), or neutral sulfite semichemical (NSSC) pulps prior to or during mechanical refining as described in numerous textbooks (Kurdin, 1980; Marteny, 1980). The sulfite pretreatment sulfonates lignin, which increases fiber swelling and water absorption, resulting in increased hydrogen bonding for papermaking. The main reaction of lignin in all sulfite pretreatment for CTMP or NSSC pulp is sulfonation.

Despite sulfite having long been used to produce chemical, chemi-thermo-mechanical, and NSSC pulps, no literature work has been reported on the application of sulfite to pretreat biomass for enzymatic saccharification. Direct application of existing sulfite processes to pretreat biomass may not yield satisfactory cellulose conversion efficiency because the performance measure of biomass pretreatment process for saccharification in biorefining is very different from that for pulping. For this reason, such application was never attempted and reported. To achieve high cellulose conversion efficiencies, an ideal pretreatment process should be capable of partially degrading cellulose and removing as much hemicellulose and/or lignin as possible, removing key barriers to cellulose access by enzymes. This is opposite to pulping where preserving cellulose strength and retaining hemicellulose are the keys to improve pulp strength and yield.

The present invention may be based on five fundamental understandings of sulfite pulping: (1) considerable degradation and removal of hemicellulose takes place as evidenced by the predominant xylose content in pulping spent liquor (Janson and Sjostrom, 1964), (2) the degree of polymerization of xylan (Pfister and Sjostrom, 1977; Meier, 1962; Sundman, 1950) and cellulose (Heuser, 1950; Thompson, 1966) are significantly reduced, (3) decreasing pulping temperature can reduce cellulose degradation and retain more hemicellulose in acid and bisulfite pulping (Hall and Stockman, 1958; Yorston, 1942; Bryce, 1980), (4) sulfonation of lignin increases the hydrophilicity of lignin, which will reduce the hydrophobic interference with enzymes, and (5) the degree of hemicellulose removal, cellulose degradation, and lignin sulfonationalion/condensation can be controlled through adjusting pulping conditions, such as temperature, pH, etc.

Because fundamental understanding on how the barriers posed by cell wall's physical and chemical (such as lignin and hemicellulose) structure affect cellulose bioconversion has been lacking (Mansfield et al., 1999; Laureano-Perez et al., 2005; Yang and Wyman, 2004), the following questions remained unanswered: (1) how lignin condensation, such as that occurs in sulfite and bisulfite pulping processes at low pH values and high temperatures, affects lignocellulose conversion; (2) how important is hemicellulose removal such as by sulfite and bisulfite processes to lignocellulose bioconversion; (3) whether or not preventing lignin condensation is more critical than hemicellulose removal and cellulose degradation to lignocellulose bioconversion. There is no scientific evidence in the literature indicating that sulfite can be effective in pretreating biomass to increase lignocellulose conversion through enzymatic saccharification.

There are several patents related to sulfite chemistry for biomass pulping, all of which are herein incorporated by reference in their entirety. U.S. Pat. No. 2,924,547 disclosed a neutral sulfite process for pulping bagasse and nonwoody biomass for fiber production. The pulping temperature was controlled at 175° C. and final pH of 6.2. U.S. Pat. No. 3,998,688 disclosed a two-step pretreatment process to produce chemical pulps. The first step can be a sulfite process with temperature of 10-60° C. U.S. Pat. No. 4,767,499 disclosed a sulfite pretreatment method for thermomechanical pulp production from spruce containing materials (spruce content at least 70%). The pretreatment temperature range is 110-130° C. Recently, U.S. Pat. No. 7,182,836 disclosed an alkaline sulfite process for delignification. The process temperature was controlled at 165-180° C. and pH varied from 7.5 to 13. All patents are for delignification to produce wood pulp. There is no disclosure about hemicellulose removal and cellulose conversion for biorefining in all these patents.

In accordance with certain aspects of the present invention, SPORL is focused on achieving (1) significant cellulose degradation, (2) complete hemicellulose removal/separation, (3) no significant delignification which avoids high chemical dosage and long reaction time, and (4) prevention of excessive lignin condensation while enhancing sufficient sulfonation of lignin through proper control to pretreatment pH, temperature, and sulfite dosage, which remove or reduce the negative impact of lignin on enzymes. The aforementioned aspects of SPORL differentiate itself from the sulfite pulping processes used to produce chemical, chemithermomechanical, semichemical, or NSSC pulps, where delignification and preserving cellulose and hemicellulose are the goals of all existing sulfite pulping processes in order to obtain strong pulp and high yield. Not only are the goals of SPORL different from the goals of all existing sulfite pulping processes, but also the process operating conditions, such as, pH, temperature, chemical dosage, etc., are different from those sulfite pulping processes.

III. SPORL Process

A. SPORL Process

One of the key features of SPORL is that it is very effective in directly pretreating chip or chop size biomass without further size reduction, as opposed to most existing methods which require significant size reduction prior to chemical pretreatment. As a result, SPORL takes advantage of the biomass structure alteration via the pretreatment, reducing subsequent biomass size reduction energy consumption. The inventors contemplate that increase of temperature higher than 180° C. in the SPORL process can reduce acid dosage without reducing cellulose conversion efficiency. Low acid dosage is favorable to reduce equipment corrosion.

Referring to FIG. 1, there is shown a specific example of an SPORL process designed in accordance with embodiments of the present invention, which can be carried out prior to significant size reduction. The pretreatment can be carried out by mixing wood chips with aqueous pretreatment liquor. It also can be carried out by steaming the wood chips preimpregnated with the pretreatment liquor described in the Summary of Invention. Biomass chips or chops may be directly subject sulfite pretreatment according to various embodiments of the present invention, followed by a mechanical size reduction step (e.g., milling, abrading, grinding, crushing, chopping, chipping or the like) and a filtration step to separate the solid substrate (mainly cellulose and lignin) fraction from the dissolved ingredients (mainly hemicellulose and a small amount of lignin as lignosulfonate). Then the substrate could be used in alternative embodiments of hydrolysis and fermentation steps to produce biofuel or biochemicals, such as separate hydrolysis and fermentation (SHF) or simultaneous saccharification and fermentation (SSF). The dissolved fraction of hemicellulose sugars can be collected with or without concentration for fermentation. The substrate and the dissolved fraction of hemicellulose sugars could also be used in alternative embodiments of chemical conversions to produce biofuels other than ethanol and biochemicals and formation of fermentation inhibitors.

Figure 2:
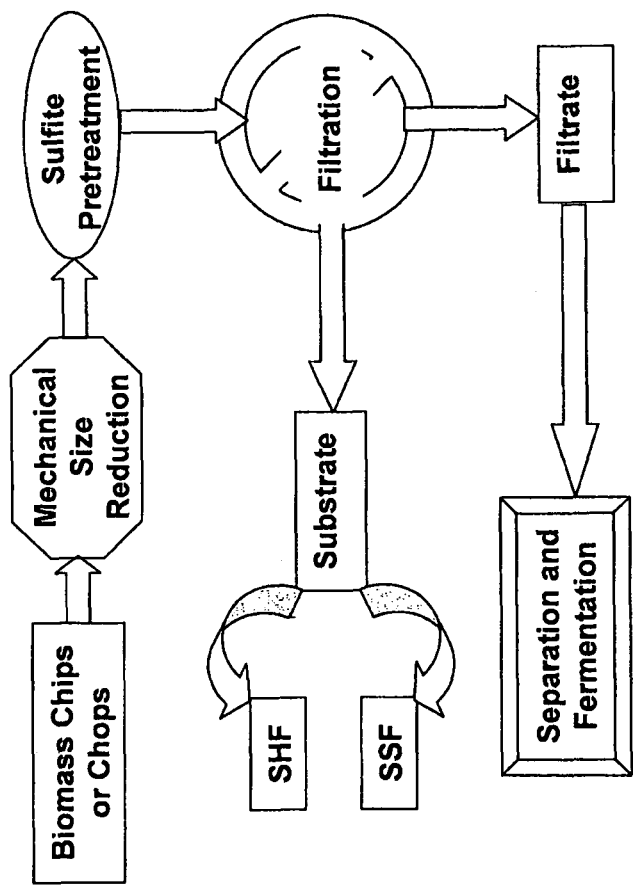
FIG. 2. Another exemplary embodiment of SPORL process flow.
Figure 3:
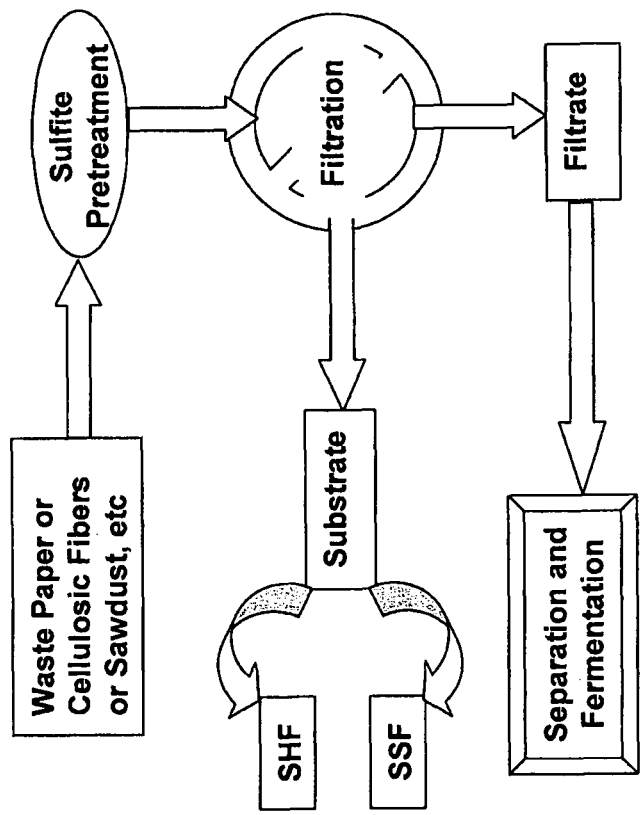
FIG. 3. Another exemplary embodiment of SPORL process flow.
Figure 4:
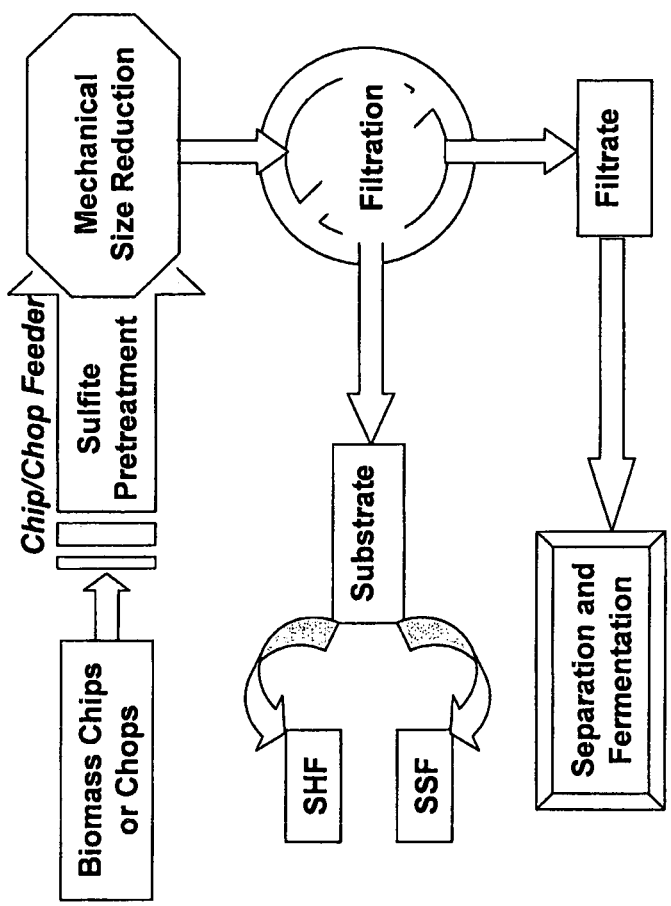
FIG. 4. Another exemplary embodiment of SPORL process flow.
Figure 5:
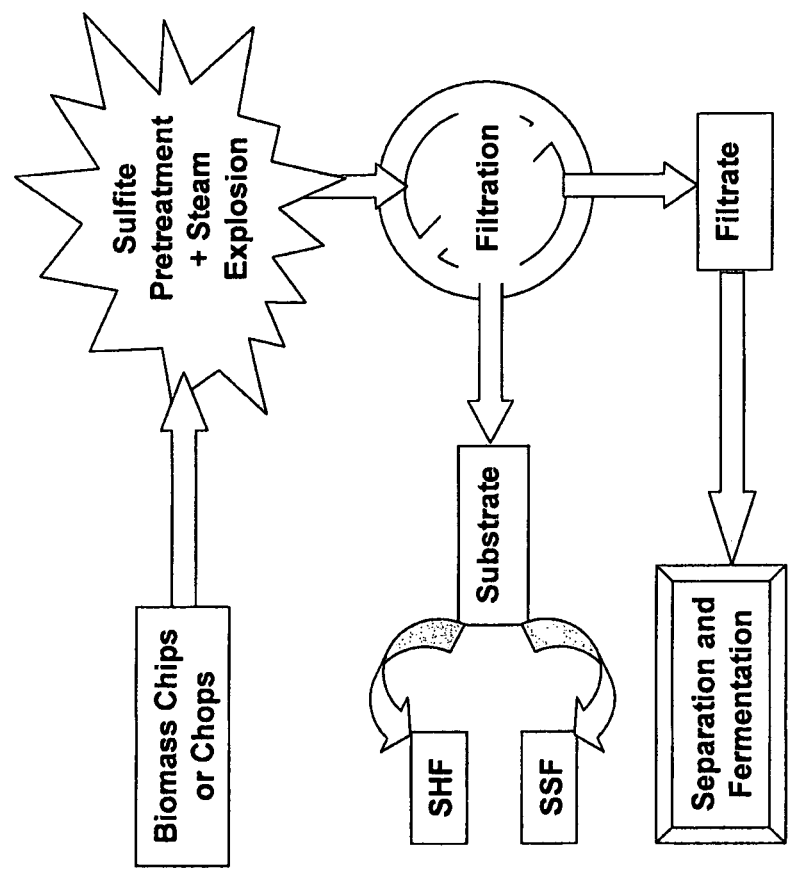
FIG. 5. Another exemplary embodiment of SPORL process flow.

Sometimes, it can be beneficial and economical when pretreatment is carried out using feedstock with higher levels of size reduction. The feedstock can be obtained from efficient size reduction technologies, such as during agriculture biomass harvesting, timber sawing, or other special processes, or from existing waste product, such as waste paper. SPORL can be applied to biomass that has received size reduction past the chip size level as shown in FIGS. 2-3. In modern chemithermomechanical pulping (CTMP), chemical pretreatment is carried out in a plug screw feeder during wood chip transport to disk refining. This approach can be adapted to carry out SPORL during feeding to a size reduction process (FIG. 4). Steam explosion has been used in several studies together with $SO_2$ and other chemicals as an effective pretreatment process for cellulose conversion (Mabee et al. 2006; Wingren et al., 2003; Excoffier et al. 1991; Heitz et al. 1991). This approach can also be adapted to conduct SPORL simply by mixing certain amount of sulfite or bisulfite with $SO_2$ or sulfuric acid or other chemicals to conduct steam explosion (FIG. 5).

B. Hydrolysis

The cellulose molecules are composed of long chains of glucan. In the hydrolysis process, these chains are broken down to free the sugar, before it is converted to chemicals or biofuel biologically (fermentation) or chemically. There are two major cellulose hydrolysis (saccharification) processes: a chemical reaction using acids, or an enzymatic reaction.

In the traditional methods of chemical hydrolysis developed in the 19th century and at the beginning of the 20th century, hydrolysis is performed by attacking the cellulose with an acid. Dilute acid may be used under high temperature and high pressure, or more concentrated acid can be used at lower temperatures and pressure. Decrystallized cellulose may react with acid in the presence of water to release individual sugar molecules (hydrolysis). The product (sugar) from this hydrolysis may be then neutralized and yeast fermentation is used to produce ethanol. As mentioned, a significant obstacle to the dilute acid process is that the hydrolysis is so harsh that toxic degradation products are produced that can interfere with fermentation.

Enzymatic hydrolysis used herein can break cellulose chains into glucose molecules by cellulase enzymes. This reaction naturally occurs at body temperature in the stomach of ruminants such as cows and sheep, where the enzymes are produced by bacteria. This process uses several enzymes at various stages of this conversion. Using a similar enzymatic system, cellulosic materials can be enzymatically hydrolyzed at a relatively mild condition (for example, 50° C. and pH 5), thus enabling effective cellulose breakdown without the formation of byproducts that would otherwise inhibit enzyme activity. By far, nearly all major pretreatment methods, including dilute acid pretreatment, require enzymatic hydrolysis step to achieve high sugar yield for ethanol fermentation.

C. Fermentation

There are essentially two different types of processes that can be used to convert cellulose (and hemicellulose) to ethanol. These are the separate hydrolysis and fermentation (SHF) and the simultaneous saccharification and fermentation (SSF). The latter process has been also extended to contain simultaneous saccharification and hemicellulose fermentation (SSHF), and is also referred as simultaneous saccharification and cofermentation (SSCF). Among various cellulose bioconversion schemes, the SSF seems to be the most promising approach to biochemically convert cellulose to ethanol. Industrial ethanol production is traditionally carried out by yeast, which is a well known robust organism. New strains (either yeasts or bacteria) have been engineered to efficiently utilize all the sugars derived from the lignocellulosic raw material. Utilization of all sugars, including the hemicellulose derived pentoses and all hexoses, is essential for economical production of ethanol.

The hydrolysis conditions used in a separate hydrolysis process (SHF) are determined by the optimum conditions of the enzymes (mostly fungal cellulases having a maximum activity at 50° C. and at a pH in the range from 4 to 5). The main advantage of a separate hydrolysis stage is that the hydrolysis is carried out at the optimum temperature of the enzymes, and the separate fermentation at the optimum of the yeast, about 30° C. The major disadvantage is that the sugars released in the hydrolysis severely inhibit the cellulase activity during hydrolysis. This can be at least partially overcome by increasing the β-glucosidase activity in the preparation used (by adding separate enzyme or by using an overproducing strain). The cellulase loadings usually range from 5 to 20 FPU/g of substrate (or cellulose), and β-glucosidase is supplemented. Usually the sugar concentrations produced are quite low due to the low amount of dry matter in the hydrolysis. Yields (from the sugars) are usually higher in more dilute systems, where end product inhibition is minimized. Long reaction times also make higher ethanol yield and concentration possible.

In the simultaneous saccharification and fermentation process (SSF), the saccharification of cellulose to glucose with cellulases and the subsequent fermentation of glucose (and pentoses) to ethanol takes place in the same reactors. According to present process schemes, all reactants (cellulose, enzymes and fermenting organism) have been added at the same time. One of the most important requirements of the SSF process is the compatibility of the saccharification and fermentation systems with respect to temperature (below 37° C.), pH and substrate concentration. The main advantages offered by SSF include enhanced rate of cellulose hydrolysis due to uptake (by yeast) of sugars inhibiting cellulase activity and decreased requirement of aseptic conditions. The disadvantages are the differences in optimal conditions for hydrolysis and fermentation. Using the whole material; both the solid cellulose and hemicellulose filtrate simultaneously for fermentation instead of only the filtrate has shown advantages, for example lactic acid formation is reduced (Stenberg et al., 2000).

D. Biological and Chemical Conversions

New biological technologies are being developed to convert hexsoses and pentoses to other biofuels, biochemicals and bioproducts. These technologies offer different biological pathways for biomass refining. Catalytic chemical conversions, such as aqueous phase reforming, provide potentially efficient pathways to convert aqueous sugar streams, such as hexose or pentose solutions into various biofuels and bio chemicals. With development of nanocatalysis, this pathway can offer unlimited opportunities for biomass refining using the present invention.

E. Steam Explosion

Steam explosion is a thermochemical pretreatment of lignocellulosic biomass for bioconversion. In a reactor, steam under high pressure penetrates the lignocellulosic structures by diffusion. The steam condenses under the high pressure thereby "wetting" the material. The moisture in the biomass hydrolyzes the acetyl groups of the hemicellulose fractions, forming organic acids such as acetic and uronic acids. Sometime, external acids (e.g., sulfur dioxide and sulfuric acid) are supplemented, in particular when woody biomass is pretreated. The acids, in turn catalyze the depolymerization of hemicellulose, releasing xylan and limited amounts of glucan. Under extreme conditions, the amorphous regions of cellulose may be hydrolyzed to some degree. Excessive conditions, i.e., high temperatures and pressures, however, can also promote the degradation of xylose to furfural and glucose to 5-hydroxymethyl furfural (HMF). Furfural inhibits microbial growth, therefore is undesirable in a fermentation feedstock. The "wet" biomass is "exploded" when the pressure within the reactor is released. Typically, the material is driven out of the reactor through a narrow opening by the induced force. Several phenomena occur at this point. First, the condensed moisture within the structure evaporates instantaneously due to the sudden decrease in pressure. The expansion of the water vapor exerts a shear force on the surrounding structure. If this shear force is high enough, the vapor will cause the mechanical breakdown of the lignocellulosic structures. The process description highlights the importance of optimizing the two governing factors: retention time, and temperature. The amount of time the biomass spends in the reactor helps to determine the extent of hemicellulose hydrolysis by the organic acids. Hydrolysis of hemicellulose greatly aids the downstream fermentation process. However, long retention times will also increase the production of degradation products. As mentioned before, especially in the preparation of a fermentation feedstock, degradation products must be minimized. Temperature governs the steam pressure within the reactor. Higher temperatures translate to higher pressures, therefore increasing the difference between reactor pressure and atmospheric pressure. The pressure difference is in turn proportional to the shear force of the evaporating moisture. The temperature and retention time may vary in the range of about 190-250° C. and 1-10 min, respectively, depending on the feedstocks.

IV. Cellulose Containing Material

In certain aspects of the present invention, cellulose-containing material may be used as substrate for the SPORL process for robust cellulose conversion. In the cellulose-containing material, the carbohydrate polymers (cellulose and hemicelluloses) may be tightly bound to the lignin, by hydrogen and covalent bonds.

Cellulose, which is a β-glucan built up of anhydro D-glucose units, is the main structural component of plant cell walls and normally constitutes about 35-60% by weight (% w/w) of lignocellulosic materials.

Hemicellulose is the term used to denote non-cellulosic polysaccharides associated with cellulose in plant tissues. Hemicellulose frequently constitutes about 20-35% w/w of lignocellulosic materials, and the majority of hemicelluloses consists of polymers based on pentose (five-carbon) sugar units, such as D-xylose and D-arabinose units, and hexose (six-carbon) sugar units, such as D-glucose, D-mannose and D-galactose units. Generally, hardwood hemicellulose contains more xylose and softwood hemicellulose more mannose.

Lignin, which is a complex, cross-linked polymer based on variously substituted hydroxyphenylpropane units, generally constitutes about 10-30% w/w of lignocellulosic materials. It is believed that lignin functions as a physical barrier to the direct bioconversion (e.g., by fermenting microorganisms) of cellulose and hemicellulose in lignocellulosic materials which have not been subjected to some kind of pre-treatment process (which may very suitably be a steam explosion process as described in relation to the present invention) to disrupt the structure of lignocellulose.

The cellulose-containing material may be wood, such as hard wood and soft wood, or biomass feedstock. Biomass refers to living and recently dead biological material that can be used as fuel or for industrial production. Most commonly, biomass refers to plant matter grown for use as biofuel, but it also includes plant or animal matter used for production of fibers, chemicals or heat. Biomass may also include biodegradable wastes that can be burnt as fuel. In certain embodiments, biomass may be grown crop fiber consisting primarily of cellulose, hemicellulose and lignin, and includes, without limitation, grass, switchgrass, straw, corn stover, cane residuals, general cereal wastes, wood chips and the like, that can be converted to ethanol (or other products) according to U.S. Pat. No. 4,461,648 and U.S. Pat. No. 5,916,780, or other known technology.

A. Hardwood

Hardwood comprises wood from broad-leaved (mostly deciduous, but not necessarily, in the case of tropical trees) or angiosperm trees. On average, hardwood is of higher density and hardness than softwood, but there is considerable variation in actual wood hardness in both groups, with a large amount of overlap; some hardwoods (e.g., balsa) are softer than most softwoods, while yew is an example of a hard softwood. Hardwoods may have broad leaves and enclosed nuts or seeds such as acorns. They may grow in subtropical regions like Africa and also in Europe and other regions such as Asia. The dominant feature separating hardwoods from softwoods is the presence of pores, or vessels. The list below includes non-limiting examples of hard wood in accordance with certain aspects of the present invention:

Afzelia (*Afzelia*)
Agba yun (*Synsepalum duloificum*)
Albizia (*Albizia*)
Alder (*Alnus*): Black alder (*Alnus glutinosa*), Red alder (*Alnus rubra*)
Applewood or wild apple (*Malus*)
Ash (*Fraxinus*): Black ash (*Fraxinus nigra*), Blue ash (*Fraxinus quadrangulata*), Common ash (*Fraxinus excelsior*), Green ash (*Fraxinus pennsylvanica lanceolata*), White ash (*Fraxinus americana*)
Aspen (*Populus*): American aspen (*Populus tremuloides*), Bigtooth aspen (*Populus grandidentata*), European aspen (*Populus tremula*)
Ayan (*Distemonanthus benthamianus*)
Balsa (*Ochroma pyramidale*)
Basswood (*Tilia americana*)
Beech (*Fagus*): European Beech (*Fagus sylvatica*), American Beech (*Fagus grandifolia*)
Birch (*Betula*): Gray birch (*Betula populifolia*), Paper birch (*Betula papyrifera*), Sweet birch (*Betula lenta*), Yellow birch (*B. alleghaniensis* syn *Betula lutea*), Silver birch (*Betula pendula*), White Birch (*Betula pubescens*)
Blackbean (*Castanospermum australe*)
Blackwood: Australian Blackwood also Tasmanian Blackwood (*Acacia melanoxylon*), African Blackwood or Mpingo (*Dalbergia melanoxylon*)
Bocote (*Cordia alliodora*)
Boxwood or Box (*Buxus sempervirens*)
Brazilwood (*Caesalpinia echinata*)
Bubinga (*Guibourtia*)
Buckeye (*Aesculus*): Common Horse-chestnut (*Aesculus hippocastanum*), Yellow Buckeye (*Aesculus flava*)
Butternut (*Juglans cinerea*)
Carapa (or Andiroba, Carap, Crappo, Crabwood and Santa Maria) (*Carapa guianensis*).
Catalpa (*Catalpa*)
Cherry (*Prunus*): Black cherry (*Prunus serotina*), Red cherry (*Prunus pennsylvanica*), Wild cherry (*Prunus avium*), Brazilian Cherry Chestnut (*Castanea dentata*): Cape Chestnut (*Calodendrum capense*)
Coachwood (*Ceratopetalum apetalum*)
Cocobolo (*Dalbergia retusa*)
Corkwood (*Leitneria floridana*)
Cottonwood, eastern (*Populus deltoides*)
Dogwood (*Cornus* spp.)
Ebony (*Diospyros*): Andaman marble-wood (India) (*Diospyros kurzii*), Ebène marbre (Mauritius, E. Africa) (*Diospyros melanida*), Gabon ebony, Black ebony, African ebony (*Diospyros crassiflora*)
Elm: American elm (*Ulmus americana*), English elm (*Ulmus procera*), Rock elm (*Ulmus thomasii*), Slippery elm (*Ulmus rubra*), Wych elm (*Ulmus glabra*)
Eucalyptus (*Eucalyptus*): Lyptus, Karri (W. Australia) (*Eucalyptus diversicolor*), Mahogany eucalyptus (New South Wales) (*Eucalyptus*), Ironbark (*Eucalyptus sideroxylon*), Jarrah or West Australian eucalyptus (*Eucalyptus marginata*), Tasmanian oak or Mountain ash, (*Eucalyptus regnans, Eucalyptus obliqua, Eucalyptus delegatensis*), River Red Gum, Blue Gum (*Eucalyptus saligna*)
Greenheart (Guyana) (*Chlorocardium rodiei*)
Grenadilla (Mpingo) (*Dalbergia melanoxylon*)
Gum: Blackgum (*Nyssa sylvatica*), Blue gum (*Eucalyptus globulus*), Redgum or Sweetgum (*Liquidambar styraciflua*), Tupelo gum (*Nyssa aquatica*)
Hickory (*Carya*): Mockemut hickory (*Carya alba*), Pignut hickory (*Carya glabra*), Shagbark hickory (*Carya ovata*), Shellbark hickory (*Carya laciniosa*)
Hornbeam (*Carpinus* species)
Hophornbeam, Eastern (*Ostrya virginiana*)
Ipê or Poui (*Tabebuia*)
Iroko (*Milicia excelsa*, syn. *Chlorophora excelsa*)
Ironwood refers to the wood of many tree species noted for the hardness of their wood. Trees commonly known as ironwoods include: *Carpinus caroliniana*—also known as American hornbeam, *Casuarina equisetifolia*—Common Ironwood from Australia, *Choricbangarpia subargentea, Copaifera* spp., *Eusideroxylon zwageri, Guajacum officinale* and *Guajacum sanctum*—Lignum vitae, *Hopea odorata, Krugiodendron ferreum*—Black Ironwood, *Lyonothamnus lyonii* (*L. floribundus*)—Catalina Ironwood, *Mesua ferrea*—also known as Rose Chestnut or Ceylon Ironwood, *Olea* spp.—various olive trees, *Olneya tesota*—Desert Ironwood, *Ostrya virginiana*—Hop hornbeam, *Parrotia persica*—Persian Ironwood, *Tabebuia serratifolia*—Yellow Lapacho
Jacarandá, Brazilian rosewood (*Dalbergia nigra*)
Jatobá (*Hymenaea courbaril*)
Lacewood from the Sycamore (N. Am.) or Plane (UK) trees (*Platanus* species)
Laurel, California (*Umbellularia californica*)
Limba (*Terminalia superba*)
Lignum vitae (*Guaiacum officinale* and *Guaiacum sanctum*)
Locust: Black locust or Yellow locust (*Robinia pseudacacia*), Honey locust (*Gleditsia triacanthos*)
Mahogany: Mahogany (African) (*Khaya* spp.), Mahogany (West Indies or Cuban) (*Swietenia mahagoni*), Mahogany (Honduras, Central and South America) (*Swietenia macrophylla*)
Maple (*Acer*): Sugar maple (*Acer saccharum*), Black maple (*Acer nigrum*), Manitoba maple (*Acer negundo*), Red maple (*Acer rubrum*), Silver maple (*Acer saccharinum*), Sycamore maple (*Acer pseudoplatanus*)
Meranti (*Shorea* spp.)
Mpingo (Grenadilla) (*Dalbergia melanoxylon*)
Oak (*Quercus*)
American White Oak includes wood from any of the following species of trees: Bur oak (*Quercus macrocarpa*), White oak (*Quercus alba*), Post oak (*Quercus stellata*), Swamp white oak (*Quercus bicolor*), Southern live oak (*Quercus virginiana*), Swamp chestnut oak (*Quercus michauxii*), Chestnut oak (*Quercus prinus* or *Q. Montana*), Chinkapin oak (*Quercus muhlenbergii*), Canyon live oak (*Quercus chrysolepis*), Overcup oak (*Quercus lyrata*)
English oak, also French and Slovenian oak barrels (*Quercus robur* or *Quercus petraea*)
Red oak includes wood from any of the following species of trees: Red oak (*Quercus rubra*), Black oak (*Quercus velutina*), Laurel oak (*Quercus laurifolia*), Southern red oak (*Quercus falcata*), Water oak (*Quercus nigra*), Willow oak (*Quercus phellos*), Nuttall's oak (*Quercus texana* or *Q. nuttallii*)
Obeche or Samba, Ayous, Arere, Wana, Abache (West Africa) (*Triplochiton scleroxylon*)
Okoumé or "Gaboon" (*Aucoumea klaineana*)
Oregon Myrtle or California Bay Laurel (*Umbellularia californica*)
Pear (*Pyrus communis*)
Pernambuco is another name for Brazilwood (*Caesalpinia echinata*)
Poplar (*Populus*): Balsam poplar (*Populus balsamifera*), Black poplar (*Populus nigra*), Hybrid poplar (*Populus canadensis*)
Ramin
Redcedar (*Toona ciliata*)
Rosewood (*Dalbergia* spp.)
Sal (*Shorea robusta*)
Sandalwood (*Santalum*)
Sassafras (*Sassafras albidum*)
Sassafras (Australia) (*Atherosperma moschatum*)
Satinwood (Ceylon) (*Chloroxylon swietenia*)
Silky Oak (*Grevillea robusta*)—Sold as Lacewood in North America
Silver Wattle (*Acacia dealbata*)
Snakewood
Sourwood (*Oxydendrum arboreum*)
Spanish-cedar (*Cedrela odorata*)
American sycamore (*Platanus occidentalis*)
Teak (*Tectona grandis*)
Walnut (*Juglans*): Black Walnut (*Juglans nigra*), Persian Walnut (*Juglans regia*)
Willow (*Salix*)
Black willow (*Salix nigra*)
Cricket-bat willow (*Salix alba* 'Coerulea')
White willow (*Salix alba*)
Yellow-poplar (*Liriodendron tulipifera*)

B. Soft Wood

Softwood is a generic term used in woodworking and the lumber industries for wood from conifers (needle-bearing trees from the order Pinales). Softwood-producing trees include pine, spruce, cedar, fir, larch, douglas-fir, hemlock, cypress, redwood and yew. Softwood is also known as Clarkwood, Madmanwood, or fuchwood. The list below includes non-limiting examples of soft wood in accordance with certain aspects of the present invention:

Araucaria
Hoop Pine (*Araucaria cunninghamii*)
Parana Pine (*Araucaria angustifolia*)
Pehuén or Chile Pine (*Araucaria araucana*)
Cedar (*Cedrus*)

Cypress (*Chamaecyparis, Cupressus, Taxodium*): Arizona Cypress (*Cupressus arizonica*), Bald Cypress or Southern cypress (*Taxodium distichum*), Hinoki Cypress (*Chamaecyparis obtusa*), Lawson's Cypress (*Chamaecyparis lawsoniana*), Mediterranean Cypress (*Cupressus sempervirens*)

Rocky Mountain Douglas-fir (*Pseudotsuga menziesii* var. *glauca*)

European Yew (*Taxus baccata*)

Fir (*Abies*): Balsam Fir (*Abies balsamea*), Silver Fir (*Abies alba*), Noble Fir (*Abies procera*), Pacific Silver Fir (*Abies amabilis*)

Hemlock (*Tsuga*): Eastern Hemlock (*Tsuga canadensis*), Mountain Hemlock (*Tsuga mertensiana*), Western Hemlock (*Tsuga heterophylla*)

Kauri (New Zealand) (*Agathis australis*)

Kaya (*Torreya nucifera*)

Larch (*Larix*): European Larch (*Larix decidua*), Japanese Larch (*Larix kaempferi*), Tamarack Larch or Tamarack (*Larix laricina*), Western Larch (*Larix occidentalis*)

Pine (*Pinus*): Corsican pine (*Pinus nigra*), Jack Pine (*Pinus banksiana*), Lodgepole Pine (*Pinus contorta* subsp *latifolia*), Monterey Pine (*Pinus radiata*), Ponderosa Pine (*Pinus ponderosa*), Red Pine (N. Am.) (*Pinus resinosa*), Scots Pine, Red pine (UK), Red deal (UK), Redwood (UK, obsolete) (*Pinus sylvestris*), White Pine (Yellow or Weymouth pine, Eastern White Pine (*Pinus strobus*), Western White Pine (*Pinus monlicola*), Sugar Pine (*Pinus lambertiana*)), Southern Yellow pine (Loblolly Pine (*Pinus taeda*), Longleaf Pine (*Pinus palustris*), Pitch Pine (*Pinus rigida*), Shortleaf Pine (*Pinus echinata*))

Redcedar: Eastern Redcedar, (*Juniperus virginiana*), Western redcedar (*Thuja plicata*)

Redwood (*Sequoia sempervirens*)

Rimu (New Zealand) (*Dacrydium cupressinum*)

Spruce (*Picea*): Norway Spruce (*Picea abies*), Black Spruce (*Picea mariana*), Red Spruce (*Picea rubens*), Sitka Spruce (*Picea sitchensis*), White Spruce (*Picea glauca*)

Sugi (*Cryptomeria japonica*)

Whitecedar: Northern Whitecedar (*Thuja occidentalis*), Southern Whitecedar (*Chamaecyparis thyoides*)

Yellow-cedar (Nootka Cypress *Callitropsis nootkatensis*, formerly *Chamaecyparis nootkatensis*)

C. Biomass Feedstock

Biomass feedstock comes in many different types, such as wood residues (including sawmill and paper mill discards), municipal paper waste, agricultural residues (including corn stover, straw, hull and sugarcane bagasse), and dedicated energy crops, which are mostly composed of fast growing tall, woody biomass.

Corn stover comprises leaves and stalks of maize (*Zea mays* ssp. *mays* L.) plants left in a field after harvest. It makes up about half of the yield of a crop and is similar to straw, the residue left in field after harvest of any cereal grain. It can be used as a fuel for bioenergy or as feedstock for bioproducts. Maize stover, together with other cellulosic biomass, provides about the potential 1.3 billion tons of raw materials per year that could produce future fuel in the next 50 years.

Useful sources of straw include in particular cereals (cereal grasses), i.e., gramineous plants which yield edible grain or seed. Straw from, for example, oat (*Avena* spp., such as *A. saliva*), barley (*Hordeum* spp., such as *H. vulgare*), wheat (*Triticum* spp., including *T. durum*), rye (*Secal cereale*), rice (*Oryza* spp.), millet (e.g., species of *Digitaria, Panicum, Paspalum, Pennisetum* or *Setana*), sorghum (*Sorghum* spp., including *S. bicolor* var. *durra* (also referred to as "durra") and milo), buckwheat (*Fagopyrum* spp., such as *F. esculentum*) and maize (also referred to as corn (*Zea mays*), including sweetcorn] is well suited for treatment according to the process of the invention.

As employed herein, the term "hull" generally denotes the outer covering, rind, shell, pod or husk of any fruit or seed, but the term as employed herein also embraces, for example, the outer covering of an ear of maize. Relevant hulls include hulls selected among the following: hulls from oat (*Avena* spp., such as *A. saliva*), barley (*Hordeum* spp., such as *H. vulgare*), wheat (*Triticum* spp., including *T. durum*), rye (*Secal cereale*), rice (*Oryza* spp.), millet (e.g., species of *Digiftaa, Panicum, Paspalum, Pennisetum* or *Setaria*), sorghum (*Sorghum* spp., including *S. bicolor* var. *durra* and milo), buckwheat (*Fagopyrum* spp., such as *F. esculentum*), maize (also known as corn (*Zea mays*), including sweetcorn), corn cob, rape-seed (from *Brassica* spp., such as *B. napus, B. napus* subsp. *rapifera* or *B. napus* subsp. *oleifera*), cotton-seed (from *Gossypium* spp., such as *G. heraceum*), almond (*Prunus dulcis*, including both sweet and bitter almond) and sunflower seed (*Helianthus* spp., such as *H. annuus*).

Hulls of cereals, including not only those mentioned among the above, but also hulls of cereals other than those mentioned among the above, are generally of interest in the context of the invention, and preferred hulls, such as oat hulls and barley hulls, belong to this category. In this connection it may be mentioned by way of example that oat hulls are often available in large quantities at low cost as a by-product of oat-processing procedures for the production of oatmeal, porridge oats, rolled oats and the like; thus, a total of around 75,000 tons of oat hulls is produced per year as a by-product of oat-processing in Denmark, Norway and Sweden together with northern Germany. Other types of hulls of relevance in relation to processes of the invention include, for example, palm shells, peanut shells, coconut shells, other types of nut shells, and coconut husk.

It should be noted that the native physical form, bulk and/or dimensions of cellulosic materials such as wood, straw, hay and the like will generally necessitate, or at least make it desirable, to carry out comminution of the material (e.g., by milling, abrading, grinding, crushing, chopping, chipping or the like) to some extent in order to obtain particles, pieces, fibers, strands, wafers, flakes or the like of material of sufficiently small size and/or sufficiently high surface area to mass ratio to enable degradation of the material to be performed satisfactorily. In the case of wood, material of suitable dimensions will often be available as a waste product in the form of sawdust, wood chips, wood flakes, twigs and the like from sawmills, forestry and other commercial sources.

In contrast, numerous types of hulls, e.g., cereal grain or seed hulls in general, including oat hulls as employed in the working examples reported herein, have in their native form sufficiently small dimensions and a sufficiently high surface area to mass ratio to enable them to be used directly, without prior comminution, as cellulosic materials in a process according to the present invention.

V. Size Reduction and Energy Consumption

The key impediments in cellulose bioconversion are the physical and chemical barriers posed by plant cell walls that limit hydrolytic enzymes access to the biomass macrostructure (cellulose) (Jeoh et al., 2007). The natural resistance to microbial and enzymatic deconstruction of lignocellulosic biomass is often called recalcitrance (Himmel et al., 2007). The technical approach to overcome recalcitrance has been pretreatment of biomass feedstock to remove the barriers and make cellulose more accessible to hydrolytic enzymes for conversion to glucose. Typically, both physical and chemical pretreatments have been used. Physical pretreatment refers to the reduction of physical size of biomass feedstock to increase enzyme-accessible surface areas (Lynd, 1996; Zhu et al., 2009a) and decrease the crystallinity of cellulose. Chemical pretreatment refers to the process of using chemicals to remove or modify key chemical components that surround and protect cellulose in biomass, mainly hemicellulose and lignin. However, the issue of physical size reduction has been completely overlooked in the cellulosic ethanol/chemical research community. The reason is likely in part because most cellulosic ethanol/chemical research has been focused on using agricultural residue that does not need a significant amount of mechanical energy to achieve satisfactory size reduction. However, size reduction is very energy intensive for certain feedstocks, such as wood, bamboo, giant reed, and bush crops.

A simple energy balance calculation using woody biomass to demonstrate the importance of size reduction for biomass refining may be conducted. It is assumed that ethanol yield from wood is about 300 liters/ton of oven-dried wood with current technology. Higher heating value of ethanol is about 24 MJ/liter, which gives total wood ethanol energy of 7.2 MJ/kg wood. Typical energy consumption to produce wood chips is about 50 Wh/kg. The energy consumption in the second step through disk milling can be anywhere from 150 to 700 Wh/kg (Schell and Harwood, 1994), depending on the fiberization process and the degree of milling. Assuming total size-reduction cost is 200 to 600 Wh/kg, which is equivalent to 0.72 to 2.16 MJ/kg, or 10 to 30% of the wood ethanol energy available. Therefore, significant reduction in size-reduction energy consumption is a key for economical cellulosic ethanol production from woody biomass.

Certain aspects of this invention relates to (1) a process to efficiently reduce the size of biomass feedstock with significantly reduced mechanical energy consumption and (2) a procedure to characterize the "size" or "specific surface" of size-reduced biomass substrate in liquid systems that can correlate with enzymatic or chemical cellulose saccharification and that can be used to optimize exposed surface area of the biomass substrate. Specifically, this invention contemplates conducting chemical or biological pretreatment of feedstock in large size, e.g., the form of chips or chops, to alter the biomass chemical and physical structure before conducting size reduction to fibers, fiber bundles, or powders. This inventive approach can lower the mechanical energy consumption during feedstock size-reduction to the level for efficient enzyme or chemical hydrolysis. More specifically, the invention relates to control mechanical size-reduction process conditions, such as disk plate gap, plate pattern, and liquid-to-solid ratio or solids-loading (consistency) in size-reduction of chemically or biologically pretreated biomass feedstock (in the form of chips or chops), to reduce size-reduction energy consumption without affecting the enzymatic hydrolysis glucose yield (EHGY) from the size-reduced substrate. U.S. Pat. No. 3,808,090, disclosed a low consistency disk milling process but was to improve mechanical pulp property such as color and strength. The invention was not about energy saving in size-reduction for hydrolytic cellulose conversion to sugars.

The term "low solids (consistency) milling" is different from "low consistency refining" (range from 0.1-10%) frequently used in mechanical wood pulping in which disk milling of wood chips are always carried out at about 50% moisture (close to the moisture in wood at harvesting) for the first pass (primary) of milling, and then further refining the pulp obtained from the first pass at "low consistency" during subsequent passes to reduce energy consumption. So, the term of "low consistency refining" is referred to the low consistency of the feed pulp in post primary refining. While, the term "low solids (consistency) milling" used in certain aspects of the present invention is referred to the low solids chips or chops in the primary milling. Only one pass (primary) milling needs to be carried out for biomass size-reduction using milling in most applications. This invention also specifically describes the use of wet imaging techniques, very similar to those commercially available for fiber characterization (length, fine content, coarseness, etc.) used in the pulp and paper industry. The novelty of certain aspects of the present invention lies in fiber external surface, model developed for determining the specific surface of a fiber.

A. Wood Chip Size Reduction and Characterization

There are two steps in wood fiber production. The first step deals with coarse size reduction, i.e., reducing the wood log to a chip size of around 10-50 mm in two dimensions and about 5-10 mm in the third dimension. The second step is to further reduce the wood chip to fibers and/or fiber bundles with lengths of about 2 mm. The energy consumption in the first step is lower than that in the second step. Therefore unless otherwise indicated, the term "size-reduction process" used in this invention is referred to the second step. The objective of the second step size reduction is to reduce the heat and mass transfer limitations, which will significantly improve the efficiency of pretreatment and hydrolysis reactions (Tillman et al., 1989; 1990).

Figure 6:
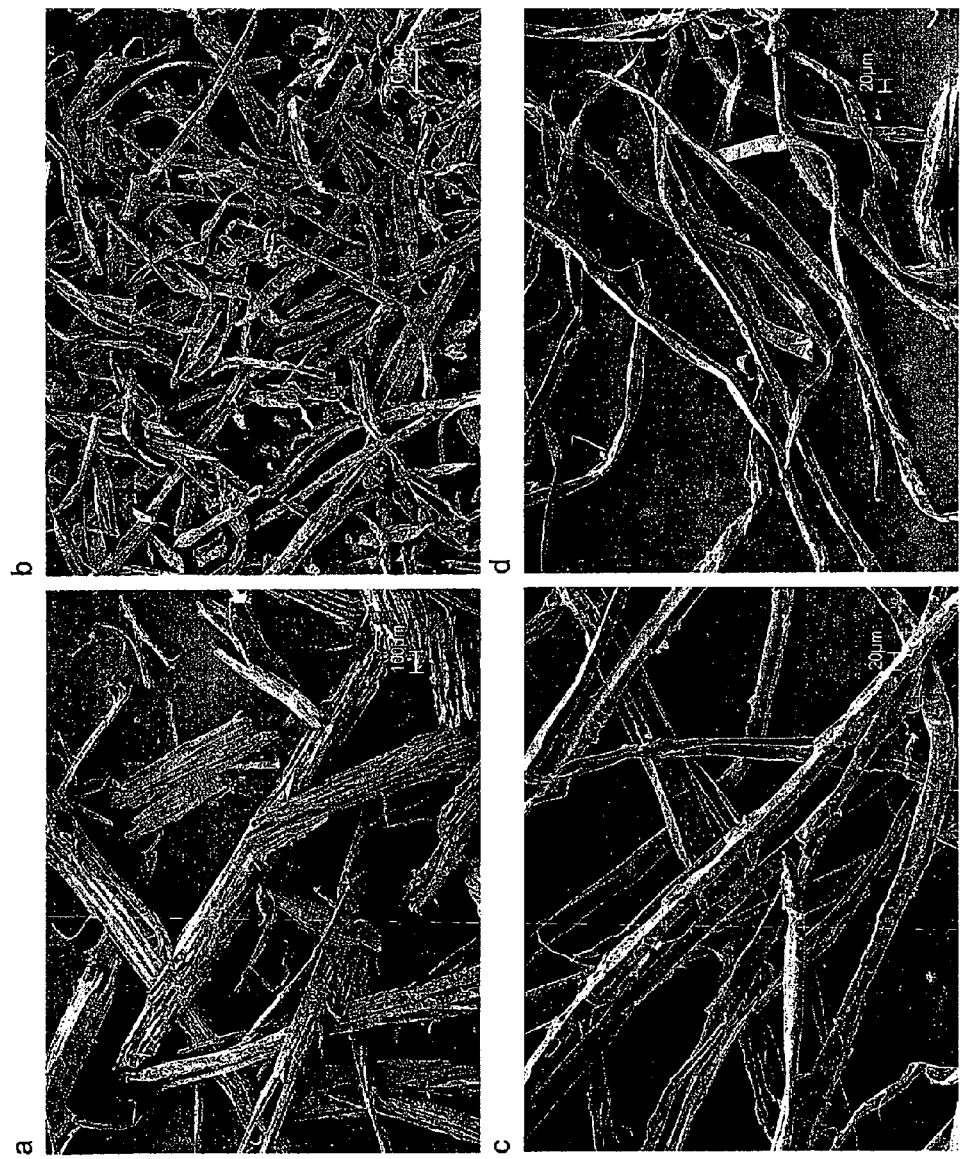
FIGS. 6A-D. Scanning electron microscope (SEM) images of different fractions of hammer-milled (FIG. 6A) HM-R80 and (FIG. 6B) HM-P80 and disk-milled (FIG. 6C) DM-I-R28 and (FIG. 6D) DM-I-R48 substrates.

Several well developed technologies are available for biomass size reduction, such as hammer milling, knife milling, shredding, and disk or attrition milling. Several studies reported biomass size reduction using these technologies (Holtzapple et al., 1989; Cadoche and Lopez, 1989; Schell and Harwood, 1994; Mani et al., 2004). Early work on size reduction of woody biomass included those producing wood flour for manufacturing wood composites (Reineke, 1961). The efficiency of a size-reduction process using commercial technologies has been evaluated in terms of energy consumption and the size of the final product, which was often characterized by the geometric mean diameter of the particles (Mani et al., 2004). This was probably because size measurements were often carried out by traditional sieve or screen methods (Dasari and Berson, 2007; Hoque et al., 2007; Cadoche and Lopez, 1989; Schell and Harwood, 1994; Mani et al., 2004). Because substrate surface area is most relevant to heat and mass transfer and enzyme accessibility, the hydrolysis efficiency combined with substrate specific surfaces should be used in evaluating the efficiency of size reduction. Holtzapple et al. (1989) used specific surface area to correlate energy consumption for comparing the efficiencies of several size-reduction processes. Their calculation of specific surfaces was based on the assumption that the substrate particles are spherical. Unfortunately, many biomass substrate particles are not spheres but shives or spindles with aspect ratios greater than 10 (FIG. 6). The substrates derived from disk milling processes typically have an aspect ratio of 50 to 100.

B. Effect of Biomass Substrate Size on the Efficiency of Enzymatic Hydrolysis

Limited studies have reported the effect of substrate size on cellulose to glucose conversion during enzymatic hydrolysis. Rivers and Emert (1987) concluded that particle size of substrates derived from ball milling had no effect on hydrolysis yield in the wet particle size range of 0.25-0.47 mm studied. Cullis et al. (2004) and Ballesteros et al. (2000) reported that initial wood chip size can affect cellulose saccharification even when the substrates were obtained after steam explosion of the chips. Chundawat et al. (2007) found that particle size affected enzymatic digestibility of ammonia fiber/freeze explosion-(AFEX-) pretreated corn stover. Mooney et al. (1999) indicated that hydrolysis rate is significantly affected by fiber size and fiber surface area. Dasari and Berson (2007) studied the effect of particle size measured by sieving on the glucose conversion using redoak sawdust collected from a commercial saw mill. They found that glucose conversion rate almost doubled when particle size was reduced from 590-850 to 33-75 µm. Sangseethong et al. (1998) found that substrate hydrolysis efficiency was not affected by the internal pore surface area but rather by the substrate size or external surface (calculated with spherical particle assumption) even though the internal pore surface contributed to over 90% of the total surface of their microcrystalline cellulose. They suggested that the enzyme-accessible internal pore surface depends on the pore depth dictated by the substrate size. As a result, they concluded that particle size is an important structural property of substrate that affects enzymatic saccharification.

Biomass substrates often have a very large and a wide range of aspect ratio (5 to 200). Substrate size measured using traditional sieving and screening methods is significantly affected by the substrate morphology such as aspect ratio. Unfortunately, the sieving method has almost been used exclusively in the biomass refining community for substrate-size characterization, which may limit scientific progress on determining effective size-reduction and chemical pretreatment processes for biomass refining. It is unclear how much internal pore surface contributes to total enzyme-accessible area and what the critical pore depth is from the work of Sangseethong et al. (1998). As a first step, this invention addresses the characterization of biomass substrate size and the external specific surface using wet image technique and various substrate fiber/particle models.

C. Factors Affect Energy Consumption during Size Reduction

Four factors affect energy consumption during size reduction: the fiberization mechanism, chemical or biological pretreatment prior to size reduction, milling process conditions, and the degree of size reduction. All these factors also affect enzymatic cellulose saccharification. Most of the existing literature on size reduction was carried out for pellet, fiber, and wood flour production. Few studies on biomass size reduction have taken an integrated approach to examining energy consumption, enzyme-accessible substrate surface, and chemical pretreatment efficiency in terms of enzymatic cellulose conversion.

Energy consumption in mechanical pulping of wood depends significantly on how the wood chips were fiberized, i.e., fiberization mechanism. Refiner mechanical pulps (RMP) are produced under atmospheric refining conditions with wood chips fractured through the lumen of wood tracheid. Thermomechanical pulps (TMP) are produced using low-pressure steam about 2.4 bar (~134° C.) to soften wood chips before disk refining. The wood chips are fractured in the S1 and S2 layer of cell wall (Salmen et al., 1999). Medium density fiberboard pulps (MDF) are produced under increased steam pressure of above 5 bar. In the MDF production process, wood chips are fractured in the lignin-rich middle lamella (ML). This is because the steam temperature reaches the glass transition temperature of lignin (Irvine, 1985). The energy consumption of different pulping processes varies significantly. Typical energy consumptions for producing RMP, TMP, and MDF are about 600, 450, 150 Wh/kg oven-dried wood, respectively. The energy consumption for chemical-thermomechanical pulp (CTMP) is just lower than that for TMP. The surface chemical compositions of these pulps are very different. RMP exposes mostly cellulose on fiber surface. MDF fibers are lignin-coated on their surface. This can be clearly seen from the color of these pulps with RMP being the most light and MDF being brown. The difference in surface chemical composition certainly affects cellulose enzymatic conversion to glucose, as revealed in previously (Zhu et al., 2009a). The significant variations in mechanical energy consumption of these different pulping processes may provide avenues for potential energy savings in biomass size reduction. However, attempts have not yet been taken to explore this potential.

The second factor affecting size-reduction energy consumption and enzymatic cellulose saccharification is chemical, thermal, or biological pretreatment. The pretreatment alters the chemical composition and physical structure of biomass by partly removing some cell-wall components such as hemicellulose and lignin. As a result, size reduction after chemical pretreatment consumes less energy. This energy saving may be insignificant for some agricultural biomass, such as corn stover or switch grass, but could be significant for biomass with strong physical integrity, such as wood, bamboo, and giant reed. However, no prior art suggested to take advantage of chemical pretreatments to reduce energy consumption in size reduction for biomass cellulose conversion, except those studies related to wood pulp production (Kenealy et al., 2007).

The third factor is related to the first factor discussed above: the wood chip fiberization process. But this factor is more concentrated on variation of milling conditions, such as variation of milling disk plate gap, plate pattern, wood solids-loading, and controlling milling temperature and pressures which do not alter fiberization mechanism as discussed in the first factor. It is well known from mechanical pulping that disk refining conditions such as those mentioned here can affect energy consumption in refining. However, the amount of energy savings achievable is very limited. In mechanical pulp production, fiber quality is critical to paper and fiber board properties, which limits opportunities to reduce milling energy through significant process condition variations, for example, Alami et al. (1995) reported only 7% energy savings by reducing disk refining consistency from 50% to 38% and no energy savings for low consistency (solids loading) below 35%. To maintain fiber quality, it prohibited further reduction in refining consistency to achieve more savings in refining energy. Fiber quality is often measured by fiber length, fiber strength, the contents of fine (very small broken fibers) and shieve (fiber bundles). For enzymatic cellulose hydrolysis application, fiber quality is not an issue, which allows us a lot of freedom to explore potential energy savings through milling process variations in much great ranges. This novelty of the present invention is that the energy saving strategies are different from those in traditional mechanical pulping through variations of refining process conditions.

To address the degree of size reduction, the fourth factor, proper characterization of biomass substrate is necessary. The geometric mean diameter of the substrate particles measured by traditional sieving and screen methods has been almost exclusively used for biomass substrate size characterization (Mani et al., 2004). This size measure is significantly affected by biomass substrate morphology such as particle aspect ratio (Zhu et al., 2009a). Most size-reduction processes produce fibrous substrate with wide ranges of particle (fiber) aspect ratio of 5 to 100. As a result, existing data on substrate size characterization has limited value.

D. Size Reduction Energy Saving Methods

Certain aspects of the invention explored the potential of three of the above four factors: (1) chemical/biological/thermal pretreatment, (2) milling process conditions, and (3) degree of size-reduction, to reduce energy consumption in size reduction for biomass bioconversion. Specifically, this invention proposes to conduct chemical/biological/thermal pretreatment before size reduction. More importantly, for example, this invention achieved significant energy consumption reduction by about a factor of 10 through controlling milling conditions without losing enzymatic saccharification efficiencies, specifically, using low solids (consistency) disk milling with relatively large gap. In certain embodiments, this invention also used wet press to concentrate the substrate from disk milling for subsequent high consistency hydrolysis or other conversion steps. To correctly measure the degree of size reduction, the present invention may also use a method for rapid and proper characterization of the size-reduced substrate specific surface using a wet imaging technique.

Figure 7:
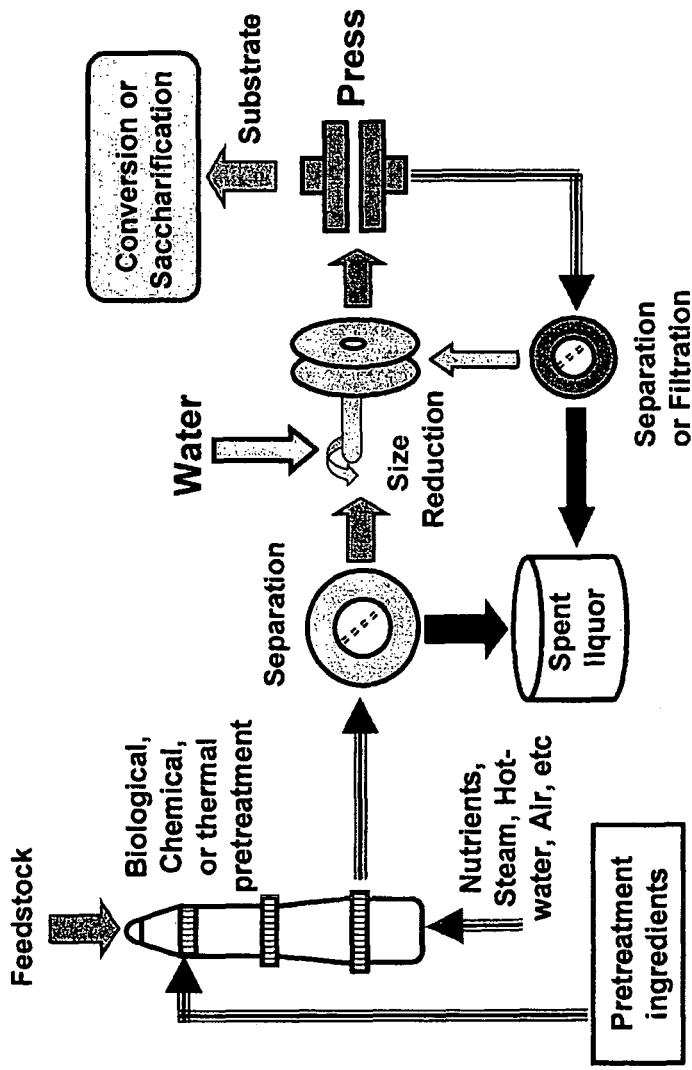
FIG. 7. Schematic process flow diagram used for reducing energy consumption in size-reduction through disk milling.
Figure 8:
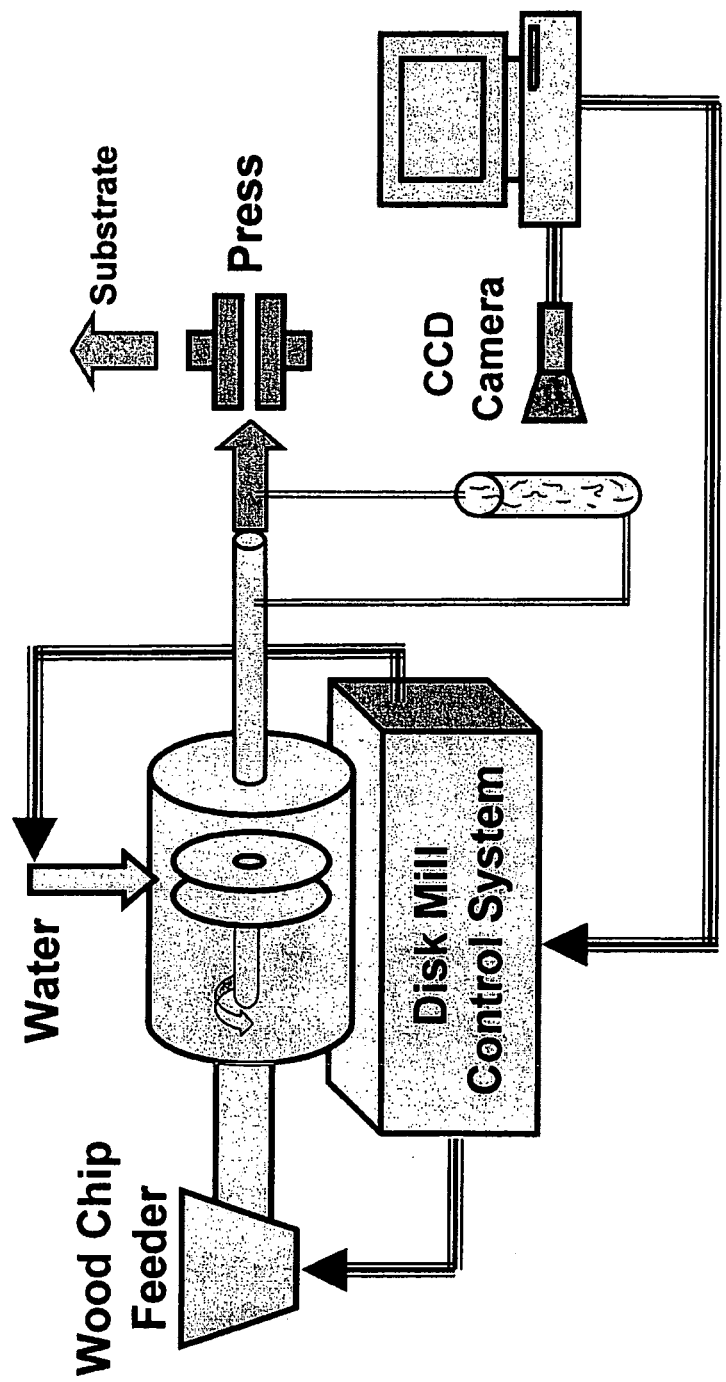
FIG. 8 Schematic process flow diagram for process control of size-reduction using disk milling based on in-situ data of energy consumption and substrate specific surface and size measured by the wet imaging technique describe din the present invention.

FIG. 7 shows a particular embodiment of process flow. Feedstock in the form of chips or chops was first fed into a pretreatment reactor. After a mild pretreatment, chemical, biological, or thermal, or the combination of any of these three types, the feedstock should remained in the chip or chop form though its chemical or physical structure may have changed. The solid of the pretreated feedstock is then separated using a simple screen device. The solid is then disk milled with water. Depends on the amount of water used in milling, the milled substrate can be directly wet pressed to remove water to concentrate to solids about 30% or higher. Filtration before wet pressing may be needed if a lot of water was added in milling. The dewatering process through filtration and pressing also serves as a washing step for the pretreated substrate to remove residual chemicals and dissolved components (hemicellulose and lignin) from pretreatment. The concentrated substrate of solids content about 30% can be directly used for subsequent hydrolysis or conversion steps with or without additional washing. Other milling process conditions, disk plate gap and temperature, etc., can be varied as necessary. FIG. 8 shows another particular embodiment of process flow that can achieve process optimization in size-reduction through disk milling to reduce energy consumption without significantly affecting size-reduction and therefore cellulose bioconversion efficiency. The substrate specific surface and size are characterized in-situ using the wet imaging technique described in this invention. The online measured size-reduction energy consumption (in terms of disk miller rotor torque or electric energy) data along with the in-situ substrate size/specific surface are used to optimize disk milling process conditions, such as disk plate gap, milling solids-loading, etc.

This post-chemical pretreatment size-reduction process flow design has several benefits: (1) it takes advantage of chemical pretreatment to alter feedstock structure to reduce energy consumption in the subsequent size-reduction (disk milling) process; (2) it avoids the difficulties and high-energy consumption for mixing high-consistency fiberized feedstock with chemicals in pretreatment when size-reduced biomass is used; (3) it can reduce thermal energy consumption in chemical pretreatment; and (4) it can potentially produce a concentrated hemicellulose sugar stream from chemical pretreatment step to reduce concentration cost. The rationale for (3) and (4) is that a low liquid to biomass ratio can be used in the chemical pretreatment of biomass with minimal size reduction (not fiberized, such as chips or chops). Liquid uptake of size-reduced (fiberized) feedstock is much higher than that of unreduced biomass (chips or chops) because of the porous and hydrophilic nature of biomass and therefore requires a higher liquid to biomass ratio.

VI. Examples

The following examples are included to further illustrate various aspects of the invention. It should be appreciated by those of skill in the art that the techniques disclosed in the examples that follow represent techniques and/or compositions discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods for SPORL Process

A. Materials

The following materials were used to demonstrate the effectiveness of SPORL. Fresh Spruce, Aspen, Maple, and Red Pine chips were from the Wisconsin Rapids mill of Stora Enso North America (now New Page Corporation, OH). The purities of the wood chips were not provided. However, the chemical composition of the two wood chip samples are very close to those of pure spruce and red pine, respectively, obtained in the inventors' laboratory previously (Zhu et al., 2007). The chips were frozen at a temperature of about $-16°$ C. until used. Fresh clone Eucalyptus wood chips were supplied by the University of Florida (Gainesville, Fla.). Fresh cornstover was obtained from the Arlington research farm of the University of Wisconsin, Madison. All the biomass was kept frozen at temperature about $-16°$ C. before use. The waste paper was commercial newsprint paper. The wood chips were screened to remove all particles greater than 38 mm and less than 6 mm in length. This screening is not necessary for producing substrates for enzymatic hydrolysis research. However, it helped to maintain a constant chip feeding rate in disk milling. The thickness of the accepted chips ranged from 2 to 6 mm. The source corn stover was hammer milled to an approximate size of 5×20 mm.

Commercial enzymes were used to demonstrate certain aspects of the present invention. In particular, Celluclast 1.5 L (cellulase), Novozym 188 (β-glucosidase), and polyethylene glycol (PEG) were used as received from Sigma-Aldrich (St. Louis, Mo., USA).

Sodium, magnesium, and ammonia bisulfite, sulfuric and hydrochloric acids were used as received from Sigma-Aldrich (St. Louis, Mo., USA). Other sulfite, such as calcium, potassium sulfite, etc., can certainly be used. However, magnesium bisulfite may be preferred for easy chemical recovery using existing commercial chemical recovery processes practiced in the pulp and paper industry. Bisulfite is preferred because it can provide the reagents sulfite, bisulfite, and $SO_2$ in the pretreatment solution by adjusting pH of the solution.

B. SPORL Chemical Solution Preparation

There are several ways to prepare the sulfite chemical solution for SPORL applications. Calcium, sodium, magnesium, ammonia, potassium and other counter-ion bisulfite chemistries have been practiced in the pulp and paper industry (Ingruber, 1985). All these bisulfites can be applied to aspects of the present invention. Magnesium bisulfite has the advantage for easing chemical recovery (Bryce, 1980). Calcium bisulfite has the advantage of low cost. Sodium bisulfite has the advantage of excellent solubility over a wide pH range. The industry practice for producing bisulfite liquor is described in detail elsewhere (Bryce, 1980). Generally, sulfur is oxidized by burning in either a rotary or spray burner to produce sulfur dioxide. The sulfur dioxide and water is then fed through limestone (for producing calcium bisulfite) at the bottom of a large tower.

To demonstrate SPORL, the industry practice of producing bisulfite was not used in the inventors' experiments. Instead bisulfite and sulfite with various counter-ions, sulfuric acid, or hydrochloric acid were purchased commercially. Mixing acid, sulfite and bisulfite produced the pretreatment liquor to demonstrate certain aspects of the present invention.

C. Sulfite Pretreatment

Figure 9:
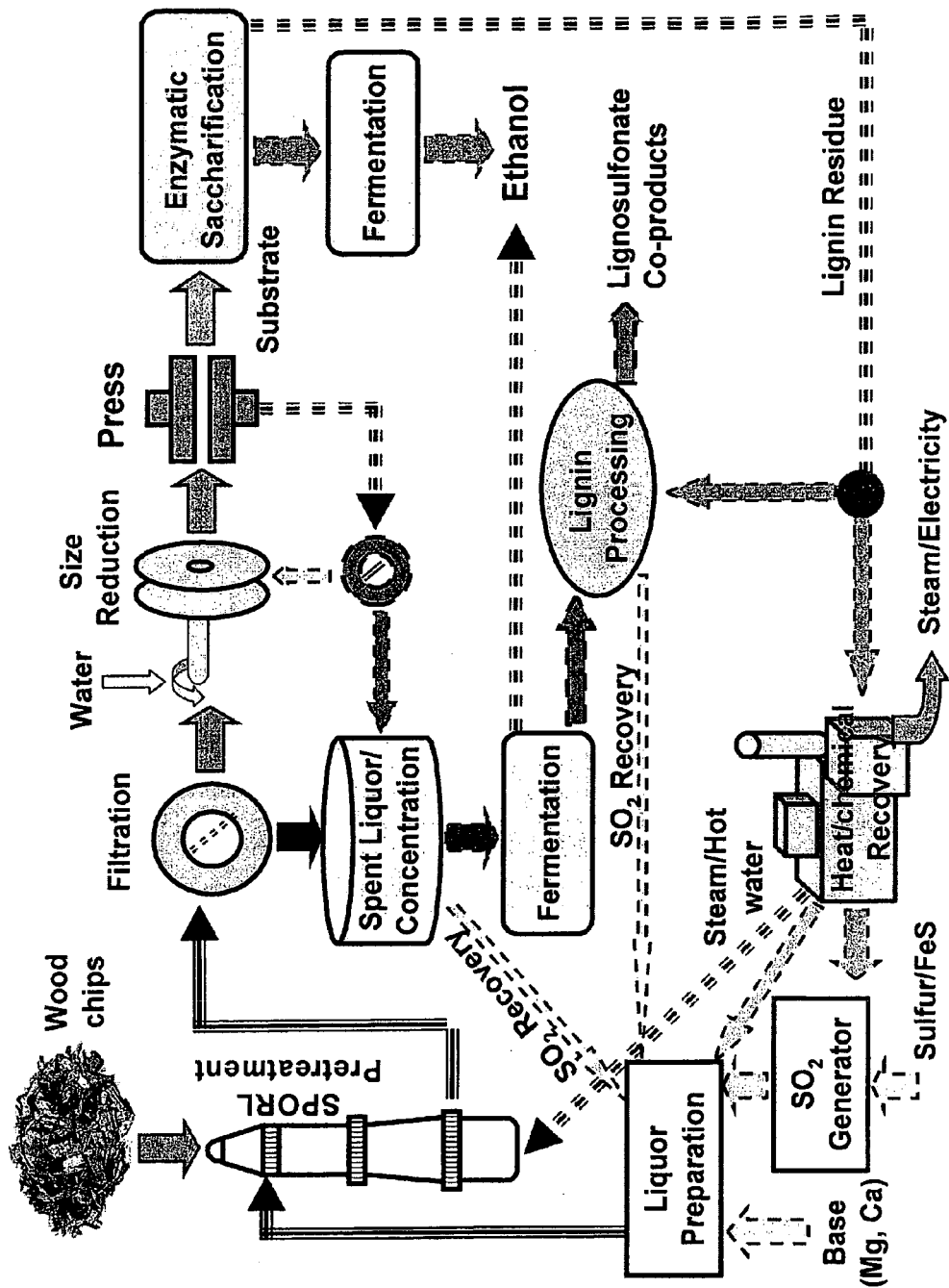
FIG. 9. Schematic process flow diagram of an exemplary embodiment of the SPORL

The SPORL experiments were conducted according to the process flow diagram shown in FIG. 9. To demonstrate the SPORL concept, wood chips, waste paper, and corn stover were pretreated in an aqueous sulfite solution followed by mechanical size reduction using disk refining. The sub-processes connected with dashed lines in FIG. 9 were not carried out in the examples presented here. The pretreatment liquor can be prepared and recovered using existing industrial practices as described elsewhere (Bryce, 1980). The pH of the solution can be easily controlled by the amount of $SO_2$ absorbed. $SO_2$ can be substituted by other acids, such as sulfuric acid, hydrochloric acid, oxalic acid, and acetic acid (such as the acetic acid released from acetyl groups during pretreatment of hardwood or agricultural residues).

When pretreatment is carried out in a separate process, traditional pulping digesters can be used. In the examples discussed below two traditional pulping digesters were used for pretreatment to demonstrate exemplary embodiments of the present invention. The two lab-scale digesters were with batch capacity of oven-dry wood chip of 130 and 2000 g, respectively. The first used 1-liter sealed stainless steel cylinders in an autoclave-type arrangement using steam heat. In the case of the 130-g batch runs, the wood chips and pretreatment solutions were placed in the sealed stainless steel 1-L pressure vessels (manufactured in-house). These 1-L vessels were mounted inside of the larger pressure vessel and heated externally via steam while rotating at the speed of 2 rpm. The second was a 23 liter stainless steel digester using steam heat via an outside jacket. In the case of the 2000-g batch runs, the wood chips and pretreatment solution were placed into the 23-L stainless steel, steam-jacketed rotating pressure vessel (unknown manufacturer). The contents were heated via the external steam jacket and rotated at a speed of 2 rpm to provide the mixing. About 130 and 2000 g of oven-dry chips or chops were used in the two digesters, respectively.

Wood chips, corn stover and/or waste paper were directly subjected to pretreatment using sodium, magnesium, and/or ammonia bisulfite with or without sulfuric acid prior to subsequent size reduction described below. The pretreatment liquor was made of sulfite or bisulfite mixed with either acid or sodium hydroxide for pH adjustment. The pretreatment liquor to biomass solid (oven-dry) ratio was 5 (v/w). The bisulfite charge on oven-dry (od) biomass solid varied from 0-12% (w/w) and sulfuric acid charge on od wood varied from 0 to 7.36% (w/w), which resulted in the initial pH of the pretreatment solution varying from about 1.7 to 4.5. Sodium sulfite instead of sodium bisulfite was used in experiments simulating neutral and alkaline pretreatment for mechanical and semichemical pulping. Sodium sulfite charge on od wood was 10.9% (w/w) with acid charges of 0.92% and 0% (w/w), corresponding to initial pH values of 7.6 and 10.2, respectively.

The chips or chops were first impregnated with the pretreatment liquor at temperature 90° C. The impregnation time varied from 0-3 hours. Immediately after impregnation, the temperature was raised to 180° C. and maintained for 30 minutes. The steam heating capacity of the two laboratory digesters employed limited the temperature of the SPORL experiments to 180° C. All pretreatments were carried out at 180° C. for 30 min in the examples. At the end of the pretreatment, the solid was collected and directly transferred to size reduction without washing. Solid loss was determined from the measured wet weight and moisture content of the collected solid.

D. Mechanical Size Reduction

Disk milling (DM) was used for mechanical size reduction of the pretreated feedstock to demonstrate aspects of the present invention in the examples discussed below. Hammer milling (HM) and other size reduction technologies can also be used with SPORL. Specifically, a laboratory 8-inch and 12-inch disk refiner (Andritz Sprout-Bauer Pressurized Refiner, Springfield, Ohio) were used. The collected solid from pretreatment was directly fed into the disk refiner. The mechanical refining can be carried out at different milling conditions, including steam pressure, temperature, feeding rate, disk gaps, etc. For example, steam pressure 0-200 psig and disk gap 0.0001-1 inches. It should be pointed out that size reduction can be carried out prior to chemical pretreatment (FIG. 2). It should also be pointed out that chemical pretreatment can be performed immediately before size reduction through the plug screw feeder of a disk milling following the current commercial practice for producing chemical-thermomechanical pulps (CTMP, FIG. 4), such as neutral sulfite semi-chemical pulp (NSSC). The biomass collected from size reduction was washed with water to obtain the substrate for enzymatic hydrolysis.

The pretreated biomass collected from the 1-L digester were refined using an 8-in. disk refiner. For the experiments conducted using the 23-L digester, the pretreated wood chips were fed into the 12-in. disk refiner for size reduction. Mechanical disk milling was carried out under atmospheric conditions with disk gap of 0.25 mm (0.01 inches). The electrical energy consumption for size reduction was recorded. The materials collected from size reduction were filtered on a Buchner funnel to separate solid (substrate) and liquid. The solids material from filtration was stored for characterization and enzymatic hydrolysis.

E. Enzymatic Hydrolysis

Enzymatic hydrolysis can be conducted using commercial enzymes with normal dosage. In the demonstration of certain aspects of the present invention, enzymatic hydrolysis of the substrates derived from size reduced pretreated biomass chips or chops were carried out at 2% of substrate (w/v) in 50-mL sodium acetate buffer using a shaker/incubator (Thermo Fisher Scientific, Model 4450, Waltham, Mass.) at 200 rpm. The pH and temperature were adjusted to 4.8 and 50° C., respectively. A mixture of Celluclast 1.5 L with an activity loading of approximately 15 FPU/g substrate and Novozyme 188 with an activity loading of approximately 22.5 CBU/g substrate (equivalent to about 20 FPU and 30 CBU/g cellulose) was used for enzymatic hydrolysis. An excess of Novozym 188 was used to prevent cellobiose accumulation (Emmel et al., 2003). Hydrolysates were sampled periodically for glucose analysis. Each data point was averaged from two replicates. For clarity, error bars calculated based on the relative difference of duplicate experiments are not shown in time-dependent cellulose conversion plots.

F. Analytical Methods

Cellulase activity of Celluclast 1.5 L was determined by the filter paper method (Wood and Bhat, 1988). Whatmann I filter paper was used as a standard substrate. One unit (FPU) of enzyme activity is defined as the amount of reducing sugars equivalent to glucose in mM/min by 1 ml of the initial enzymatic solution. Cellobiase of Novozym 188 was determined using cellobiose as substrate recommended by IUPAC Biotechnology Commission. One unit (CBU) of activity is defined as the enzyme amount, which converts 1 mol of cellobiose to 2 mol of glucose in 1 min (Wood and Bhat, 1988).

The chemical contents (e.g., carbohydrate compositions) of the original and pretreated biomass were measured by the Analytical and Microscopy Laboratory (USDA Forest Products Laboratory) using an improved high performance anion exchange chromatography with pulsed amperometric detection (HPAEC-PAD) method (Davis, 1998).

The solid materials were milled using a Wiley mill (Thomas Scientific, Swedesboro, N.J.) before acid hydrolysis (acid-insoluble lignin procedure). The supernatant of the acid hydrolysate was directly used for ion chromatographic (IC) analysis. The measurement relative standard deviations (RSD) were reported based on internal regular quality assurance (QA) and quality control (QC). The monomeric sugar concentrations in the pretreatment spent liquor (hydrolysate) were also measured by the same HPAEC-PAD technique. The liquor was first centrifuged to remove solid particles. The supernatant was injected into IC column after dilution. The average of triplicate measurements was used to determine the hemicellulose sugar recovery from the pretreatment.

Hydroxymethylfurfural (HMF) and furfural in the pretreatment spent liquor (hydrolysate) were measured by HPLC (HP 1090 Series II, Hewlett-Packard, Now Agilent Technologies, Palo Alto, Calif.) with UV detection at 280 nm using external standards. A reverse phase column (C18, Grace Vydac, Deerfield, Ill.) was used for separation. Results were obtained from the average of duplicate measurements. The standard deviations of selected samples reported were calculated from four sets of duplicate measurements.

The hydrolytic reaction was followed by measuring the carbohydrates in the hydrolysate. For example, the enzymatic hydrolytic reactions of pretreated substrates were monitored by measuring the time-dependent glucose concentrations in the hydrolysates. For fast analysis, glucose in the enzymatic hydrolysates was measured using a commercial glucose analyzer (YSI 2700S, YSI Inc., Yellow Springs, Ohio). The instrument precision is about 2% based on manufacturer specifications. The average of duplicate runs was used in reporting. The final hydrolysate were also measured by HPAEC-PAD.

In certain aspects of the invention cellulose conversion refers to enzymatic hydrolysis of cellulose to glucose in a substrate, whether chemically pretreated or not. The glucose yield from enzymatic hydrolysis, EHGY, is obtained from the glucose concentration in the enzymatic hydrolysate. Each glucan unit produces one glucose molecule after gaining one water molecule, therefore the ratio of molecular weight between one glucan unit and glucose of 0.9 ($C_6H_{10}O_5/C_6H_{12}O_6$) is used in the calculation of enzymatic cellulose conversion of substrate (ECCS), used interchangeably with cellulose conversion in this invention:

Enzymatic Cellulose Conversion of Substrate(ECCS)
(%)=90×EHGY(weight)/[(od substrate weight)×
(substrate glucan content)]

Example 2

Effect of Sulfuric Acid Charge (pH) on Cellulose Conversion of Spruce through Enzymatic Hydrolysis The chemical compositions of spruce wood and substrates from six SPORL experiments at 180° C. for 30 min are listed in Table 1. The first four samples were obtained with sodium bisulfite charge of 9% on od wood at different sulfuric acid charges (pH values). The last two samples were prepared using sodium sulfite at charge of 10.9% on od wood at higher pH values, simulating neutral and alkaline sulfite pretreatments for producing mechanical and semi-chemical pulps. The results indicate that hemicellulose, namely xylan and mannan, can be completely removed with sulfuric acid charge on wood 3.68% or greater (initial pH approximately 2.2). The near complete separation of hemicellulose from cellulose is favorable not only to enzymatic hydrolysis of cellulose but also to fermentation to ethanol due to lack of efficient technologies to co-ferment xylose and glucose. For the run with acid charge of 3.68% (initial pH approximately 2.2), most of the separated hemicellulose sugars can be recovered as monomeric sugars, as will be discussed later. Furthermore, approximately 12% glucan was dissolved in pretreatment liquor by acidic hydrolysis through pretreatment with about 20% delignification. The data indicate that cellulose loss through pretreatment is only about 10% with near complete removal of hemicellulose at an acid charge of 3.68% (initial pH around 2.2). Glucan dissolution or loss increased to 30% as acid charge increased to 7.36% (initial pH less than 2). The two pretreatments at higher pH values (using sodium sulfite) produced very low glucan and hemicellulose losses (dissolution), with solid yield about 90%, suggesting no significant carbohydrate hydrolysis (Table 1). However, the low degrees of degradation of cellulose and hemicellulose were found to be not favorable to enzymatic hydrolysis.

Table 2 lists the enzymatic cellulose conversion of the substrates (ECCS) derived from sulfite pretreatment with different sulfuric acid charges on oven-dry (od) wood (different pH). ECCS in percent is defined according to the equation in the preceding paragraph:

The results indicate that about 85% cellulose conversion to glucose was achieved at an acid charge of 3.68% (initial pH around 2) in about 48 hours. When the surfactant PEG was added in hydrolysis, with PEG concentration in solution of about 10%, ECCS over 90% was achieved in 12 hours and was increased to about 95% in 48 hours.

With only 19 Wh/kg od untreated wood electric energy input, the pretreated wood chips using SPORL method of the present invention can be easily pulverized with a mean fiber length around 0.3 mm for the wood chips pretreated at acid charge of 3.68% (initial pH around 2). So, the present pretreatment process meets the two 90/90 targets, i.e., 90% cellulose conversion and less than 90 Wh/kg od biomass energy consumption in size reduction. This is very significant to processes like those in the particular embodiments shown in FIGS. 1 and 4.

Disk refining and hammer milling are mature and commercially proven technologies. Disk refining has been in commercial production for several decades, with numerous sites having capacities of 1000 ton/day. With certain embodiments of this invention, processes using mechanical size reduction (FIGS. 1 and 4) are more economical than the current state of the art process of steam explosion, which is not a mature technology, of which a scale-up to 1000 ton/day for commercial production has yet to be proven, and which is very energy intensive due to the consumption of large amount of high quality steam.

tion. The hydrophobic condensed lignin might have a greater negative impact on enzymes through hydrophobic interference than hydrophilic lignosulfonate. The high lignin

TABLE 1

Weights of wood components and % loss after sulfite pretreatment at different sulfuric acid charge on oven-dry (od) wood

| Acid Charge on od wood (%) | K. Lig g (% loss) | ASL g (% loss) | Arab g (% loss) | Galac g (% loss) | Rham g (% loss) | Glucan g (% loss) | Xylan g (% loss) | Mannan g (% loss) | Sum (g) | Total (g) |
|---|---|---|---|---|---|---|---|---|---|---|
| Untreated sample | 27.6 | 0.71 | 1.35 | 2.65 | 0.11 | 43.16 | 5.72 | 11.46 | 92.76 | 100 |
| 7.36 | 26.38 | 0.64 | 0 | 0 | 0 | 30.46 | 0.11 | 0.10 | 57.68 | 58.4 |
| pH = 1.72 | (4.41) | (10.47) | (100) | (100) | (100) | (29.42) | (98.11) | (99.16) | | |
| 3.68 | 21.94 | 0.56 | 0 | 0 | 0 | 38.01 | 0.4 | 0.2 | 61.11 | 61.81 |
| pH = 2.16 | (20.51) | (21.13) | (100) | (100) | (100) | (11.93) | (93.01) | (98.25) | | |
| 1.84 | 19.16 | 0.79 | 0 | 0 | 0 | 35.58 | 2.08 | 1.05 | 58.66 | 60.00 |
| pH = 2.44 | (30.58) | | (100) | (100) | (100) | (17.56) | (63.64) | (90.84) | | |
| 0 | 18.88 | 0.65 | 0 | 0.07 | 0 | 41.96 | 2.61 | 2.09 | 66.27 | 68.0 |
| pH = 4.42 | (31.68) | (8.33) | (100) | (97.2) | (100) | (2.97) | (54.34) | (81.75) | | |
| 0.92 | 22.60 | 1.71 | 0.47 | 1.40 | 0 | 41.73 | 4.85 | 10.68 | 83.44 | 90.40 |
| pH = 7.61 | (18.12) | | (65.19) | (47.17) | (100) | (3.31) | (15.21) | (6.81) | | |
| 0 | 21.90 | 2.20 | 0.63 | 1.30 | 0 | 42.50 | 5.36 | 10.42 | 84.31 | 89.50 |
| pH = 10.24 | (20.65) | | (53.33) | (50.94) | (100) | (1.53) | (6.29) | (9.08) | | |
| RSTD (%) | 0.80 | 5.80 | 1.60 | 2.90 | 15.90 | 1.00 | 1.40 | 1.40 | — | — |

Key:
K. Lig—Klason lignin;
ASL—acid soluble lignin;
Arab—arabinan;
Galac—galactan;
Rham—rhamnan.

Figure 10:
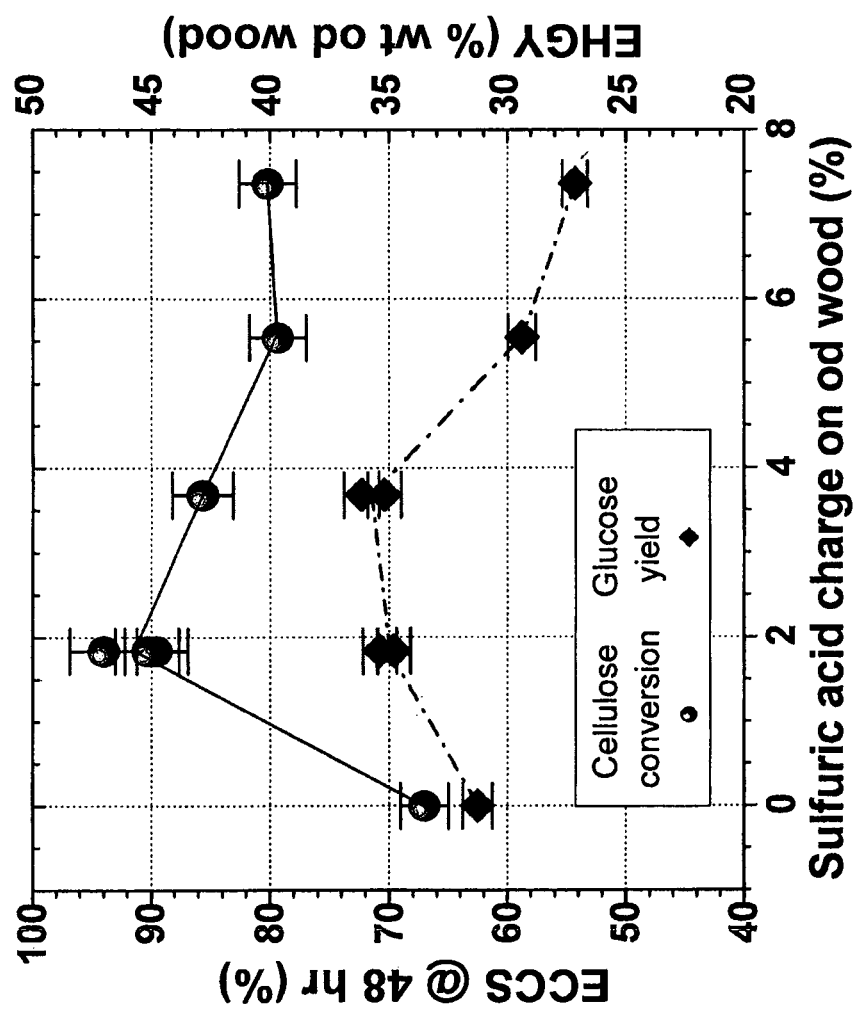
FIG. 10. Effect of sulfuric acid charge on cellulose conversion and glucose yield through 48 h enzymatic hydrolysis of spruce. Pretreatment conditions: 180° C. for 30 min with sodium bisulfite charge of 9% on od (oven-dry) wood.

The effect of sulfuric acid charge (pH) on od wood on enzymatic conversion of cellulose and glucose yield after 48 h enzymatic hydrolysis is shown in FIG. 10. At a given sodium bisulfite charge of 9% on od wood, the optimal acid charge was about 2.5%, at which both enzymatic cellulose conversion and EHGY were maximized. The maximum enzymatic conversion of cellulose and EHGY were about 90% and 37% wt od wood, respectively, which translates to an overall glucose yield of 78% from the enzymatic hydrolysis alone (excluding dissolved glucose during pretreatment) based on spruce wood cellulose content of 43.16% (Table 1). The two high-pH pretreatments resulted in very low cellulose conversion of less than 30% and EHGY of less than 15% wt od wood, implying that neutral and alkaline sulfite pretreatments are not effective for biomass conversion through enzymatic saccharification because the barriers of hemicellulose are not removed.

Examining the data presented in Table 1 and Table 2, Klason lignin (acid-insoluble lignin) removal was only 4.4% at sulfuric acid charge 7.36% (pH around 1.72, c.f. Table 1), indicating significant lignin condensation might have occurred. This resulted in an ECCS of 80% after 48 hours of hydrolysis (FIG. 10), lower than that achieved at sulfuric acid charge 3.68% (pH 2.16) and 1.84% (pH 2.42), respectively. Lignin removal was greater than 15% for these two low acid charge runs (Table 1). Furthermore, the EHGY at acid charge of 7.36% was only 27% wt od wood, lower than the 35% wt od wood obtained from the two runs with low acid charges of 3.68 and 1.84%.

One explanation is that high dosage of acid at high temperature promoted lignin condensation instead of sulfonation. The hydrophobic condensed lignin might have a greater removal achieved at lower acid charges is likely attributable to enhanced lignin sulfonation. Another reason is that more lignin was removed at lower acid charges by depolymerization and sulfonation. It can be concluded that pretreatment temperature of 180° C. is probably too high for this acid charge (pH) to achieve satisfactory lignin removal and cellulose conversion for spruce wood.

However, further reduction of acid charge to 0% in pretreatment did not produce additional improvement in enzymatic digestibility of substrate. Enzymatic cellulose conversion and EHGY were only about 69% and 31% wt od wood, respectively. This was because of limited hemicellulose removal at 0% acid charge. For example, Table 1 and Table 2 also show that lignin removal was over 30% at acid charge 0 (pH=4.4), higher than the 22% achieved at acid charge 3.68% (pH=2.16), but xylan removal was less than 55% and mannan removal was less than 82% (compared with 93% and 98% at 3.68% acid charge), which resulted in a low cellulose conversion efficiency of only about 67% after 48 hours of hydrolysis. This indicates that hemicellulose removal is as critical lignin sulfonation and removal to achieve satisfactory cellulose conversion. A temperature higher than 180° C. is probably needed to achieve satisfactory hemicellulose removal and cellulose degradation for acid charge 0% (pH around 4.4). Limited pre-hydrolysis of cellulose at 0% acid was another reason for reduced enzymatic digestibility (resulting in lower glucose yield).

This analysis indicates that there can be several optimal operating ranges for SPORL to achieve satisfactory cellulose conversion. The keys to achieve satisfactory cellulose conversion in accordance with certain aspects of the present invention are degrading cellulose and hemicellulose, removing hemicellulose, preventing excessive condensation of lignin, and promoting the sulfonation of lignin.

TABLE 2

Time-dependence of enzymatic cellulose conversion of the substrate (ECCS) and sulfite pretreatment at different sulfuric acid charge on oven-dry (od) wood

| Enzymatic Hydrolysis Time (hour) | Acid charge On od wood (%) | | | |
|---|---|---|---|---|
| | Acid = 0 pH = 4.42 | Acid = 3.68% pH = 2.16 | Acid = 7.36% pH = 1.72 | pH = 2.16 + PEG |
| | Enzymatic cellulose conversion of substrate (%) | | | |
| 1 | 18.71 | 33.08 | 30.20 | 42.45 |
| 3 | 30.19 | 55.47 | 48.87 | 69.30 |
| 6 | 38.65 | 66.89 | 60.00 | 82.70 |
| 12 | 48.54 | 76.48 | 69.28 | 89.65 |
| 24 | 57.84 | 81.96 | 77.34 | 94.04 |
| 48 | 67.06 | 85.62 | 80.19 | 94.41 |
| 72 | 69.40 | 87.09 | 81.66 | 95.14 |

Example 3

Effect of Bisulfite Charge on Cellulose Conversion of Spruce

Figure 11:
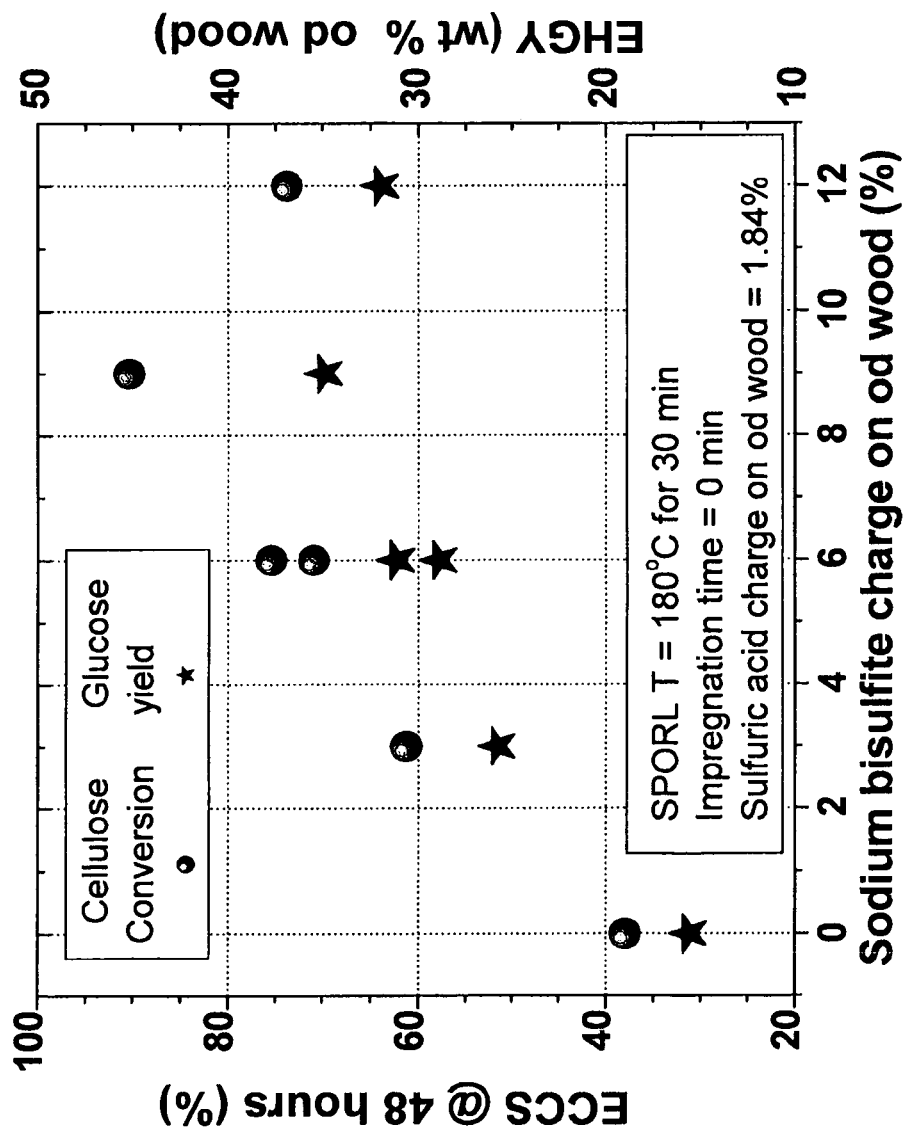
FIG. 11. Effects of sodium bisulfite charge on od (oven-dry) wood on cellulose conversion of spruce.

The effect of bisulfite charge on enzymatic digestibility of the SPORL substrates is shown in FIG. 11. Table 3 lists the effect of sodium bisulfite charge on wood chemical component removal. At the pretreatment temperature 180° C. and sulfuric acid charge of 1.84%, there was an optimal bisulfite charge around 9% at which xylan removal is the highest (above 90%). At this bisulfite charge, ECCS was over 90% (Table 4) and EHGY wt % untreated wood was about 35 g (FIG. 11) after 48 hours enzymatic hydrolysis. Table 4 and FIG. 11 show that bisulfite charge of 9% is also optimal for enzymatic cellulose conversion. Further analysis indicates that xylan removal seems to correlate to cellulose conversion. However, when the bisulfite charge is reduced to zero (sulfuric acid only), the treatment becomes the traditional dilute acid process, but high xylan removal does not translate to high cellulose conversion; this condition actually gives the lowest cellulose conversion and glucose yield of all experiments at less than 40% and 15.5% wt od wood, respectively, indicating that the enzymatic digestibility of a SPORL substrate is much better than that of a dilute acid-pretreated substrate. Further observations of the data suggest that partial lignin removal might also be important. With a bisulfite charge of zero (sulfuric acid only), no lignin was removed, which might have caused low cellulose conversion.

The addition of bisulfite dissolved a small portion of lignin. The sulfonation by sulfite makes lignin more hydrophilic, which could reduce the hydrophobic interactions with enzymes. The partial delignification and sulfonation of lignin may contribute to the significantly improved digestibility of the SPORL substrate over a dilute acid pretreated one. Further increasing bisulfite charge to over 9%, however, resulted in decreased enzymatic cellulose conversion (FIG. 11). This is because the increase in bisulfite application increased the pH of the pretreatment liquor at a given acid charge, which depressed the dissolution of hemicellulose (Table 3), and may also depressed the depolymerization of cellulose, and even the rate of lignin sulfonation. It should be pointed out that a bisulfite charge of 9% used in the SPORL pretreatment is much lower than that for traditional sulfite chemical pulping (typically 20%). This is another difference of SPORL from traditional sulfite chemical pulping.

TABLE 3

Weight of wood components and % loss after sulfite pretreatment at different bisulfite charge on wood

| Bisulfite Charge on wood (%) | K. Lig g (% loss) | ASL g (% loss) | Arab g (% loss) | Galac g (% loss) | Rham g (% loss) | Glucan g (% loss) | Xylan g (% loss) | Mannan g (% loss) | Sum (g) | Total (g) |
|---|---|---|---|---|---|---|---|---|---|---|
| Untreated sample | 27.6 | 0.71 | 1.35 | 2.65 | 0.11 | 43.16 | 5.72 | 11.46 | 92.76 | 100 |
| 12 | 18.61 (32.59) | 0.00 | 0.00 | 0.01 | 0.00 | 38.94 (9.86) | 2.55 (55.32) | 0.11 (88.56) | 59.97 | 63.20 |
| 9 | 24.63 (10.77) | 3.17 | 0.00 | 0.00 | 0.00 | 34.75 (19.57) | 0.45 (92.16) | 0.11 (83.26) | 62.88 | 61.70 |
| 6 | 23.67 (14.26) | 3.46 | 0.00 | 0.01 | 0.00 | 37.12 (14.08) | 0.95 (83.26) | 0.36 (96.87) | 65.11 | 63.70 |
| 6 | 25.67 (6.99) | 0.00 | 0.00 | 0.00 | 0.00 | 36.67 (15.12) | 1.21 (78.82) | 0.46 (95.96) | 63.42 | 65.90 |
| 3 | 19.96 (27.66) | 0.00 | 0.00 | 0.01 | 0.00 | 37.83 (12.43) | 1.91 (66.52) | 0.82 (92.84) | 59.44 | 62.50 |
| 0 | 30.07 (0) | 0.46 | 0.00 | 0.01 | 0.00 | 36.91 (14.57) | 0.49 (91.42) | 0.16 (98.57) | 67.84 | 69.50 |

Key:
K. Lig—Klason lignin;
ASL—acid soluble lignin;
Arab—arabinan;
Galac—galactan;
Rham—rhamnan.

TABLE 4

Time-dependence of enzymatic cellulose conversion of substrate from SPORL using different bisulfite charge on spruce wood

| Enzymatic Hydrolysis Time (hour) | Bisulfite charge on od wood (%) | | | | | |
|---|---|---|---|---|---|---|
| | 12 | 9 | 6 | 6 | 3 | 0 |
| | Enzymatic cellulose conversion of substrate (%) | | | | | |
| 1 | 28.05 | 35.65 | 29.72 | 28.65 | 20.68 | 14.75 |
| 3 | 43.69 | 52.67 | 43.77 | 43.06 | 32.36 | 22.03 |

TABLE 4-continued

Time-dependence of enzymatic cellulose conversion of substrate from SPORL using different bisulfite charge on spruce wood

| Enzymatic Hydrolysis Time (hour) | Bisulfite charge on od wood (%) | | | | | |
|---|---|---|---|---|---|---|
| | 12 | 9 | 6 | 6 | 3 | 0 |
| | Enzymatic cellullose conversion of substrate (%) | | | | | |
| 6 | 52.01 | 63.22 | 50.56 | 49.78 | 40.24 | 26.53 |
| 12 | 61.51 | 72.50 | 58.82 | 59.33 | 47.53 | 32.03 |
| 24 | 66.11 | 79.77 | 69.47 | 66.04 | 57.05 | 34.92 |
| 48 | 73.78 | 90.32 | 75.41 | 70.90 | 61.21 | 37.12 |
| 72 | 77.44 | 91.92 | 77.19 | 72.52 | 60.84 | 37.97 |

Example 4

Effect of Impregnation Time on Cellulose Conversion of Spruce

Biomass impregnation allows the pretreatment chemicals to uniformly penetrate into the biomass, such as wood chips, prior to reactions at the final pretreatment temperature. Impregnation is very important to acid sulfite and bisulfite pulping to get a uniform delignification or pulp quality. It is also important for dilute acid and steam explosion (if supplemental chemical is required) pretreatments for biorefining. Typical impregnation is conducted by soaking the wood chips in the pretreatment solution below the pretreatment or pulping temperature for a period of time from several minutes to several hours. In acid sulfite pulping, 3-6 hours are required to impregnate the wood chips. Such a long impregnation time wastes productivity and energy, but is necessary in sulfite and bisulfite pulping. In kraft pulping, impregnation is conducted by vacuuming the digester filled with wood chips first to remove the air pockets in the wood pores, leading to improved penetration of the pulping chemicals.

Figure 12:
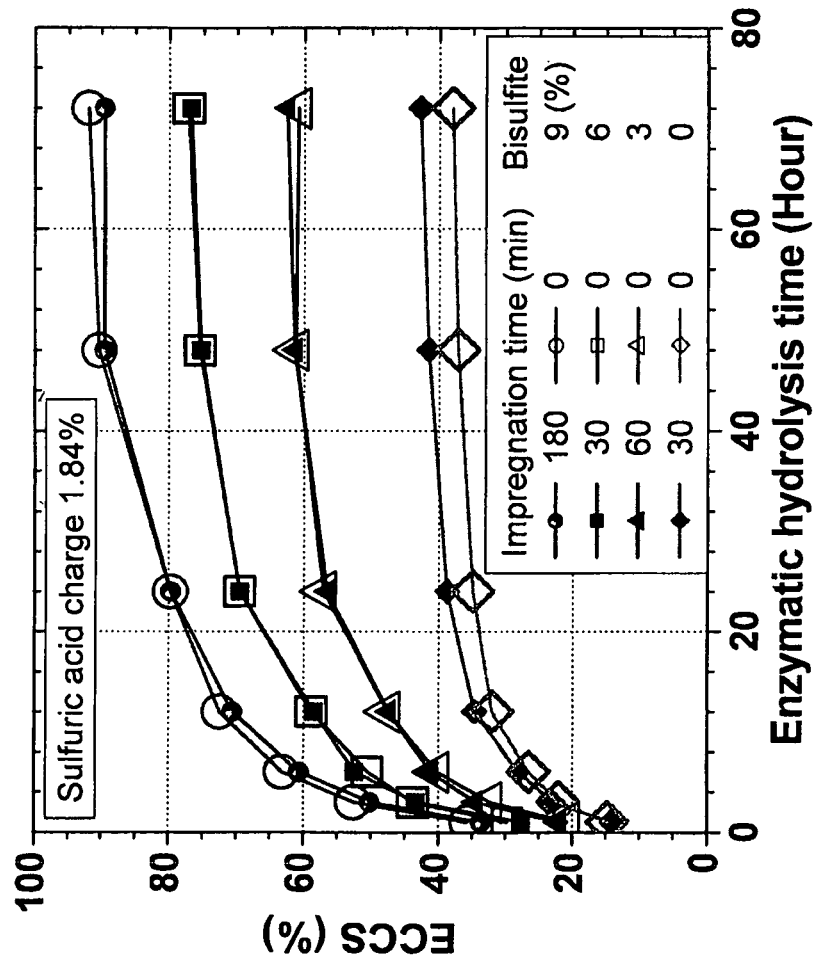
FIG. 12. Effects of wood chip impregnation time on cellulose conversion of spruce.

Spruce wood chips were soaked with the pretreatment solution at a temperature of 90° C., with the impregnation time varied from 0 to 180 minutes. After the predetermined impregnation time, the digester temperature was raised to the pretreatment temperature of 180° C. FIG. 12 shows the effect of impregnation time on ECCS obtained under various impregnation times. The results indicate that impregnation time has no effect on the substrate digestibility for the conditions tested: acid charge 1.84% and bisulfite charge of 9%, 6%, and 3%. However, when the bisulfite charge is reduced to 0 (acid only) at the same sulfuric acid charge of 1.84%, then the process became dilute acid pretreatment, impregnation has some effect in substrate digestibility and cellulose conversion, e.g., impregnation increased cellulose conversion (ECCS) by 5% after 48 hours of enzymatic hydrolysis.

Further examination of the chemical composition of the substrates indicates that impregnation time has no effects on the removal of major components from the wood chips during pretreatment. However, in the case of dilute acid pretreatment without sulfite addition, 30 min of impregnation removed over 11% more glucan than 0 min of impregnation (Table 5). This difference of 11% was obtained without replicated experiments, but it is significantly higher than the glucan measurement uncertainty of about 3% based on the seven SPORL experiments with sodium bisulfite charge of 3%, 6%, and 9% (Table 5). The standard deviations of enzymatic cellulose conversion and glucose yield shown in Table 5 were used as experimental uncertainties (error bars) shown in FIGS. 10-11.

TABLE 5

Effect of wood chip impregnation time on glucan yield, enzymatic hydrolysis conversion of cellulose and glucose yield after 48 h at 180° C. at four different bilsulfite charges and sulfuric acid charge of 1.84% on od (oven-dry) wood

| Bisulfite charge on od wood (%) | Impregnation time (min) | Enzymatic cellulose conversion at 48 h (%)[a] | Glucan yield from pre-treatment per 100 g od wood | Enzymatic glucose yield (% wt od wood) |
|---|---|---|---|---|
| 0 | 30 | 41.52 | 33.1 | 15.27 |
| | 0 | 37.12 | 36.9 | 15.22 |
| | Mean/STD | 39.32/3.11 | 35.00/2.69 | 15.24/0.04 |
| 3 | 60 | 61.21 | 38.4 | 26.12 |
| | 0 | 60.84 | 37.8 | 25.55 |
| | Mean/STD | 61.03/0.26 | 38.10/0.42 | 25.83/0.40 |
| 6 | 30 | 75.27 | 36.1 | 30.19 |
| | 0 | 75.41 | 37.4 | 31.34 |
| | Mean/STD | 75.34/0.1 | 36.75/0.9 | 30.77/0.8 |
| 9 | 180 | 89.54 | 35.6 | 35.42 |
| | 60 | 90.32 | 34.7 | 34.82 |
| | 0 | 94.02 | 33.3 | 34.79 |
| | Mean/STD | 91.29/2.39 | 34.53/1.16 | 35.01/0.35 |

[a]Based on cellulose content in pretreated substrate (glucan yield).

These results indicate that impregnation is not necessary for the SPORL, which will simplify the process and improve productivity. The results indicate that SPORL in accordance with aspects of the present invention is different from sulfite pulping (acid sulfite and bisulfite) in which wood chip impregnation is critically important to avoid cellulose and hemicellulose degradation, and lignin condensation for satisfactory lignin removal. The results also indicate that SPORL is very different from acid pretreatment in terms of enhancing digestibility and altering the wood structure to achieve cellulose conversion. With the same hemicellulose (e.g., xylan) removal, the same amount of acid, and the same temperature as SPORL, the acid pretreatment was very inefficient for cellulose conversion; i.e., ECCS is less than 40% after 48 hours of enzymatic hydrolysis. In contrast, with just a 3% sodium bisulfite charge on wood, SPORL increased cellulose conversion (ECCS) to 60% after 48 hours of enzymatic hydrolysis; cellulose conversion was even greater with increased bisulfite charge (FIG. 12).

Example 5

Pretreatment of Spruce Using Magnesium and Ammonium Bisulfite

To demonstrate that sulfite and bisulfite are the key reagents of SPORL for achieving robust conversion of cellulose through enzymatic saccharification, magnesium, ammonium, and sodium bisulfite were used to pretreat spruce wood at temperature of 180° C. Sulfuric acid charge on wood was 3.68% for all the experiments listed in Table 6. Near complete enzymatic cellulose conversion of the substrate pretreated with 8% magnesium bisulfite was achieved. ECCS reached 90% less than 24 hours hydrolysis. The EHGY in wt % untreated spruce was found to be 40 under this condition, equivalent to overall process enzymatic cellulose conversion (PECC, the EHGY over the theoretical yield from the untreated wood, taking cellulose loss in the pretreatment into account) of 83%. The low enzymatic cellulose conversion of substrates from ammonia bisulfite is probably due to low pH. It was found that the pH values of the pretreatment spent liquors were around 1.6 lower than the pH values on spent liquors using magnesium or sodium bisulfite despite the pH of the pretreatment solutions were all around 2.0. Further examining the data revealed less xylan was completely removed in those ammonia pretreatments.

TABLE 6

Time-dependence of enzymatic cellulose conversion of spruce substrate (ECCS) from SPORL under different bisulfite counter-ion and charge

| Enzymatic Hydrolysis Time (hour) | Bisulfite base and charge (%) | | | | | |
|---|---|---|---|---|---|---|
| | Ammonia bisulfite (%) | | | Magnesium bisulfite (%) | | Sodium bisulfite (%) |
| | 6 | 8 | 10 | 4 | 8 | 6 |
| 1 | 25.9 | 30.0 | 32.8 | 27.1 | 32.8 | 33.9 |
| 3 | 43.4 | 49.5 | 51.1 | 47.2 | 57.5 | 56.9 |
| 6 | 54.85 | 58.1 | 62.6 | 60.2 | 73.6 | 68.6 |
| 12 | 64.5 | 67.8 | 72.0 | 69.2 | 86.7 | 78.4 |
| 24 | 72.9 | 76.9 | 77.0 | 77.1 | 93.8 | 84.0 |
| 48 | 74.6 | 77.9 | 80.1 | 82.4 | 100.1 | 87.8 |
| 72 | 72.3 | 74.7 | 75.5 | 79.3 | 94.6 | 89.3 |

The results in Table 6 clearly show that similar ECCS were obtained after 48 hours hydrolysis under proper bisulfite charges and pH to those achieved using sodium bisulfite. The results suggest similar effectiveness of various counter-ions of bisulfite.

Example 6

Pretreatment of Spruce Using Hydrochloric Acid

Figure 13:
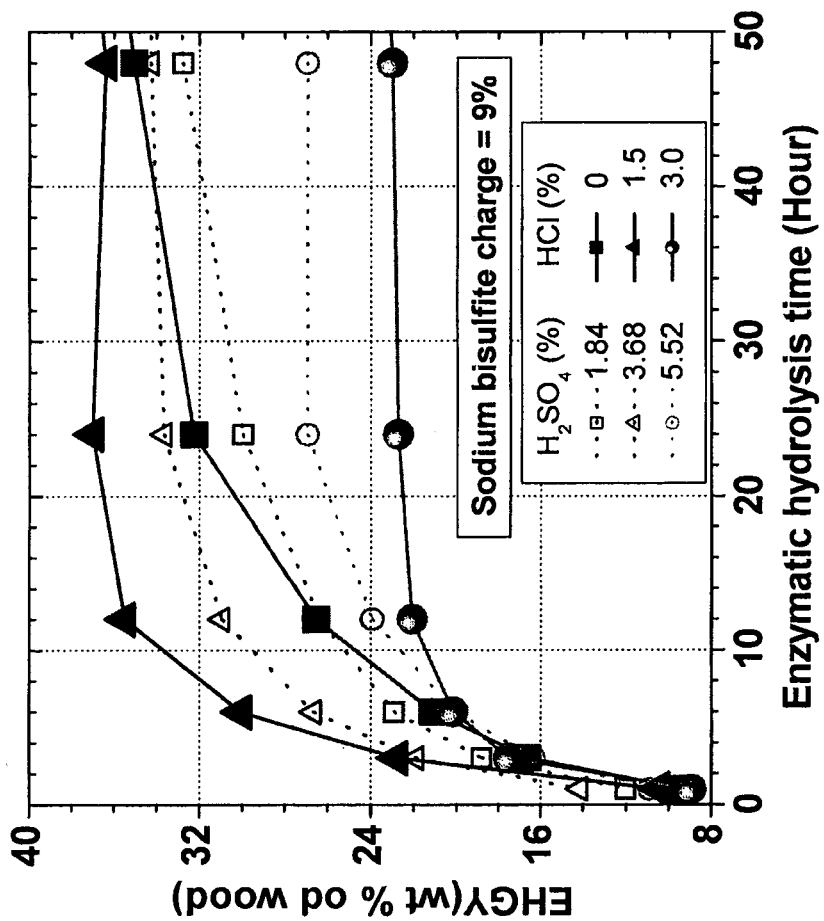
FIG. 13. Comparisons of enzymatic hydrolysis glucose yield (EHGY) wt % untreated wood between using sulfuric acid and hydrochloric acid.

Sulfuric acid is mainly for pH adjustment in SPORL. It can be substituted by other acids. In this example, the inventors used hydrochloric acid to conduct SPORL for spruce. FIG. 13 shows EHGY under hydrochloric acid charge on wood of 0, 1.5, and 3.0%, respectively. Pretreatments were carried out using sodium bisulfite charge on wood of 9% at temperature 180° C. for 30 min. The results indicate that EHGY of 36 wt % untreated wood was obtained at hydrochloric acid charge of 1.5%, which is very similar to that achieved when sulfuric acid was used (FIG. 11), i.e., ECCS of over 90%. For comparison purpose, FIG. 13 also plotted the EHGY using different sulfuric acid charges, with same bisulfite charge of 9% and under the same temperature of 180° C. The results in FIG. 13 clearly show that hydrochloric acid works just equally well or better than sulfuric acid for pH adjustment in SPORL.

Figure 14:
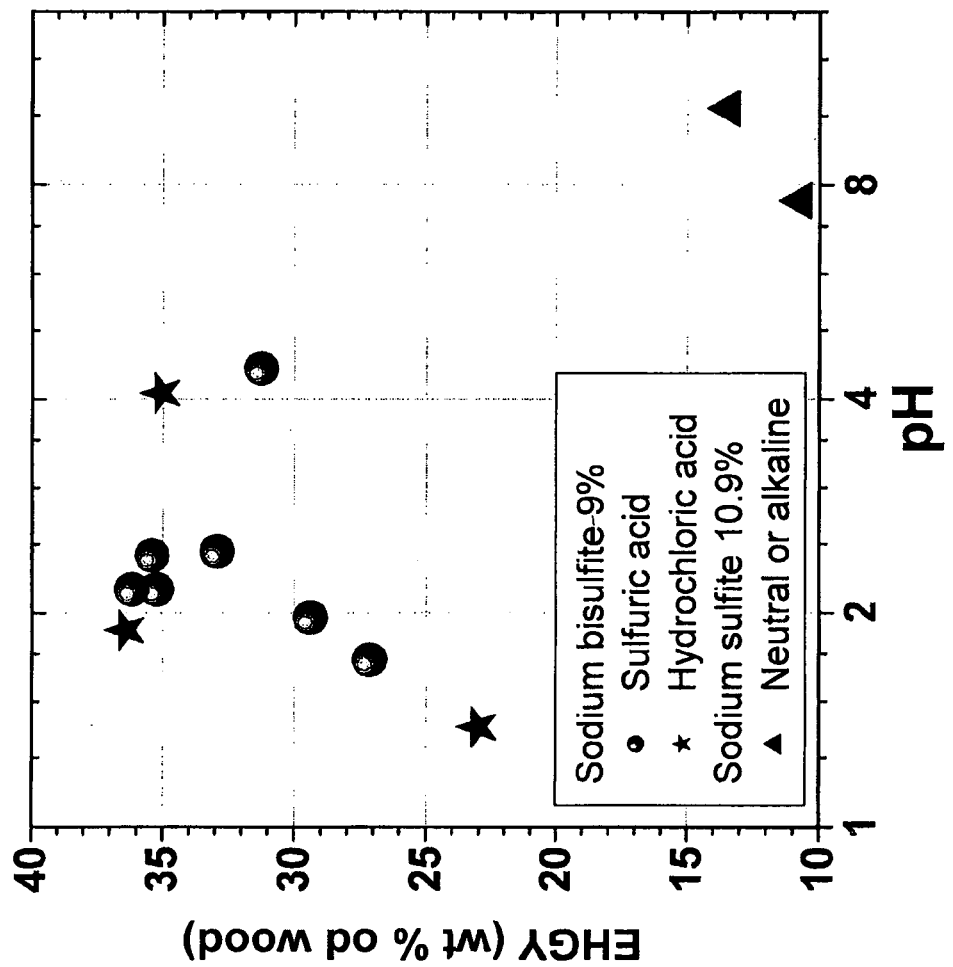
FIG. 14. Effects of pH on enzymatic hydrolysis glucose yield (EHGY) wt % of untreated wood after 48 hours hydrolysis using sulfuric and hydrochloric acid.

FIG. 14 shows the effects of pH on EHGY after 48 hours enzymatic hydrolysis using SPORL with different acids or base at temperature 180° C. The results show a general trend of EHGY first increases then decreases as pH is increased independent of the acid used, i.e., for a given pretreatment temperature, there is an optimal pH at which EHGY is maximized. It is contemplated that the optimal pH will vary with pretreatment conditions, especially, temperature and duration time.

Example 7

Application of SPORL to Other Softwood Species

Figure 15:
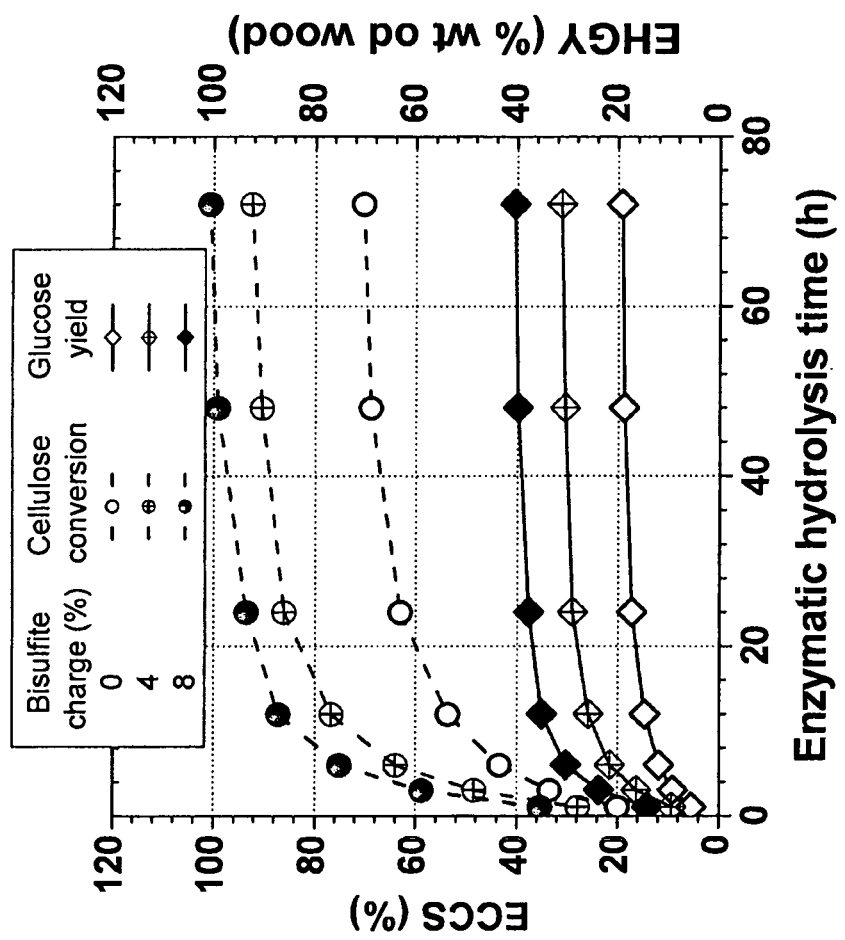
FIG. 15. Effect of magnesium bisulfite charge on time-dependent cellulose conversion and enzymatic hydrolysis glucose yield (EHGY) of red pine. Pretreatment conditions: 180° C. for 30 min with at sulfuric acid charge of 3.68% on od (oven-dry) wood.

It is known that spruce is an ideal softwood species for sulfite and bisulfite pulping in terms of producing strong pulp for papermaking. However, sulfite and bisulfite pulping generally does not work well for pines. Similarly, most pretreatment processes of lignocellulose for producing ethanol do not work well with softwood species. For example, the $SO_2$-catalyzed steam explosion process performed poorly when applied to some softwood species such as Douglas-fir (Pan et al., 2005). To demonstrate the robustness and versatility of SPORL for biorefining, the inventors applied the process to red pine, one of the dominant pine species in the northern regions of North America. The inventors demonstrated that bisulfite with different counter-ions can be used in the SPORL as in sulfite pulping (sodium, magnesium, ammonium were found to be effective on red pine in this invention). Magnesium, ammonium, and sodium bisulfite were used to pretreat red pine at a temperature of 180° C. for 30 minutes. Table 7 and FIG. 15 shows the time-dependent enzymatic cellulose conversion of the substrate. The sulfuric acid charge on wood was 3.68% for all the experiments listed in Table 7 except for the last experiment using sodium bisulfite. The data clearly show that the ECCS can easily reach 90% with 24 hours under the optimal conditions, such as magnesium bisulfite charge of 8% and acid charge 3.68%. Near 100% cellulose conversion was achieved after 48 h enzymatic hydrolysis with enzyme loadings of 14.6 FPU and 22.5 CBU per gram of substrate obtained from bisulfite charge of 8%, resulting in EHGY of 40% wt od red pine which gives an overall process enzymatic cellulose conversion of 85.7% based on untreated wood of glucan content of 42%. These results suggest the effectiveness of the SPORL for bioconversion of red pine. The low conversion of the sodium bisulfite pretreatment is due to the low acid charge of 1.2%. The ammonia pretreatments also produced low cellulose conversion due to the low pH (below 2.0 measured at the beginning of the experiment at room temperature).

TABLE 7

Time-dependence of enzymatic cellulose conversion of red pine substrate from SPORL using different bisulfite counter-ions and charge

| Enzymatic Hydrolysis Time (hour) | Bisulfite charge on od wood (%) | | | | | | |
|---|---|---|---|---|---|---|---|
| | Ammonia bisulfite (%) | | | Magnesium bisulfite (%) | | | Sodium bisulfite (%) 9 Acid = 1.2% |
| | 6 | 8 | 10 | 0 | 4 | 8 | |
| 1 | 26.3 | 33.3 | 43.3 | 20.0 | 27.8 | 35.4 | 29.6 |
| 3 | 46.5 | 53.5 | 69.8 | 33.4 | 48.4 | 58.8 | 46.7 |
| 6 | 58.4 | 65.2 | 80.2 | 43.4 | 64.0 | 75.1 | 56.3 |
| 12 | 67.2 | 73.8 | 84.0 | 53.7 | 76.7 | 87.2 | 67.6 |
| 24 | 74.7 | 78.9 | 84.8 | 63.1 | 86.1 | 93.6 | 77.1 |
| 48 | 77.4 | 79.6 | 84.0 | 68.9 | 90.5 | 99.1 | 81.7 |

The results discussed above suggest similar effectiveness of various counter-ions of bisulfite for conversion of cellulose from Red Pine. It is contemplated that the present sulfite process in accordance with certain aspects of the invention should be equally effective for other pine species, such as Southern Pine, Lodgepole Pine, and Jack Pine.

Example 8

Application of SPORL to Hardwood Species

Figure 16:
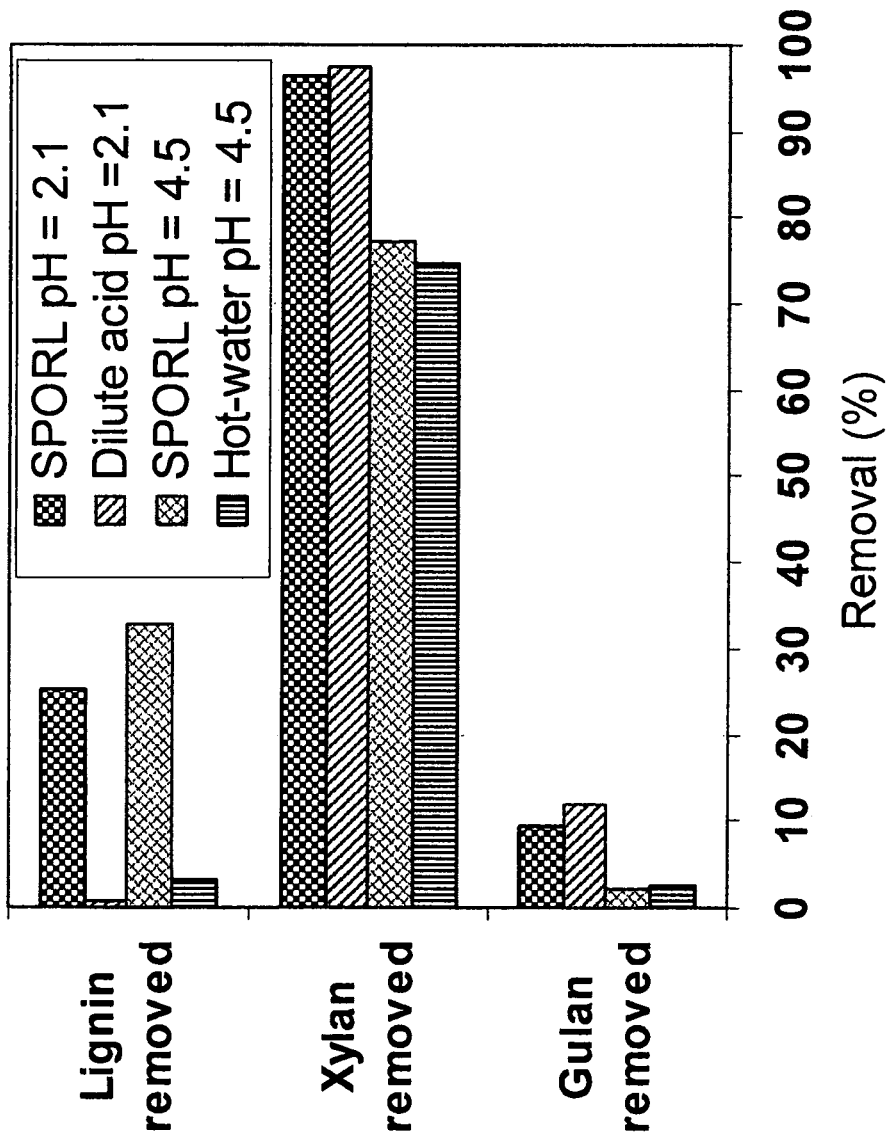
FIG. 16. Comparisons of glucan retention, xylan removal and lignin removal between bisulfite, acid and water pretreatment on hardwood.
Figure 17:
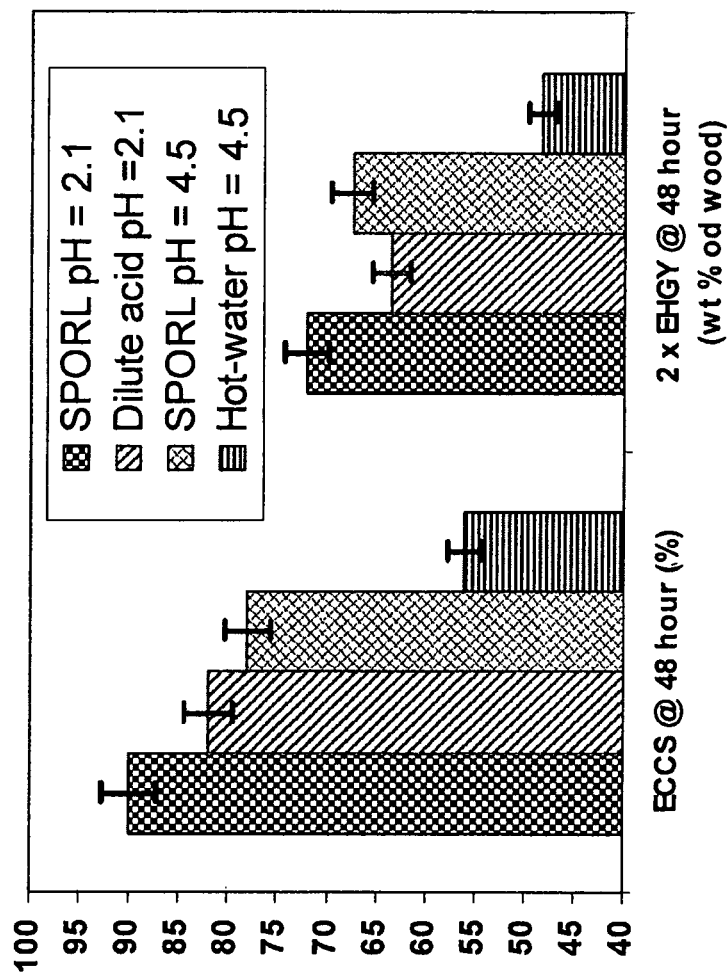
FIG. 17. Comparisons of cellulose conversion and glucose yields between bisulfite, acid and water pretreatments on hardwood.

The inventors applied SPORL to pretreat a short rotation, fast growing Eucalyptus (hardwood). SPORL conditions were acid charge on wood 1.84%, sodium bisulfite charge on wood 6%, temperature 180° C. for 30 min. FIG. 16 shows the comparisons of glucan retention, xylan removal, and lignin removal between bisulfite, acid and water pretreatments. The results indicate that about 90% of the glucan was retained with acid processes (SPORL bisulfite with acid) and almost all of the glucan was retained (>97%) without acid (water and SPORL bisulfite only). Over 95% of the xylan was removed with the pretreatments using acid while only about 75% was removed for pretreatments that did not contain acid. About 25-30% of the Klason lignin was removed with the use of bisulfite (SPORL) and none without. FIG. 17 shows the comparisons of ECCS and EHGY. The results indicate while acid only pretreatment can achieve a good ECCS of 82%, the EHGY was lower compared to that from SPORL with (initial pH=2.1) or without acid (initial pH=4.5). This is because of the combination of the higher glucan removal of 13% and lower ECCS of 82% of the acid only pretreatment compared to the 9% and 90% for SPORL with acid (pH=2.1), respectively. Sulfite only pretreatment (SPORL pH=4.5) without the addition of acid also yielded more glucose than the acid only process due to higher amount of glucan retained (>97%) in pretreatment than that for the acid only process (87%) even though the ECCS of the acid only process was 82% higher than the 78% for the bisulfite only process (SPORL). Water pretreatment resulted in very low ECCS of 56% and low EHGY. The results in FIGS. 16 and 17 indicate SPORL is very effective for pretreating short rotation, fast growing Eucalyptus. Acetic acid derived from acetyl groups of hardwood hemicellulose may replace, at lease partially, the sulfuric acid used in SPORL.

Aspen and poplar (hardwoods) are ideal feedstock for biorefining due to relatively high cellulose content and low barriers for enzymatic digestion. These species have been widely studied using steam explosion (De Bari et al., 2007) and organosolv pretreatments (Pan et al., 2006). The inventors also found that SPORL significantly increased the digestibility of aspen. Table 8 lists the major wood chemical component removal through four SPORL experiments using different acid charge (or pH) and sodium bisulfite charge of 4% on od wood at 180° C. Xylan is the major hemicellulose (16.7%) in the aspen sample. Other hemicellulose components are approximately 2% in total in the untreated wood and therefore are not reported. The results indicate that xylan can be completely removed with an acid charge greater than 1% on od wood. At acid charge zero, or pH about 4.5 (i.e., using bisulfite only), xylan removal was about 80%. Lignin removal increased with the decrease in acid charge or increase in pH. About 30% of the lignin was removed at pH around 2.0, or acid charge between 1.8% and 2.8%, on od wood, whereas over 40% of the lignin was removed at zero acid charge, or pH about 4.5. Glucan loss decreases with the decrease of acid charge. Glucan loss was less than 4% at zero acid charge, or pH 4.5.

TABLE 8

Weights of major wood (aspen) components and percentage loss after SPORL at different sulfuric acid charges at 180° C. and sodium bisulfite charge on od untreated wood of 4%

| Acid Charge On wood (%) | Klason. Lignin g (% loss) | Glucan g (% loss) | Xylan g (% loss) | Mannan g (% loss) | Sum (g) | Total Solid yield (g) |
|---|---|---|---|---|---|---|
| Untreated sample | 23.0 | 45.9 | 16.7 | 1.2 | 86.8 | 100 |
| 2.76 pH = 1.9 | 16.8 (27.0) | 37.7 (17.9) | 0.3 (98.2) | N/A | 54.8 | 58.2 |
| 1.84 pH = 2.0 | 16.1 (29.8) | 39.7 (13.6) | 0.7 (95.8) | N/A | 56.5 | 60.7 |
| 0.92 pH = 2.3 | 13.8 (40.0) | 41.1 (10.5) | 1.5 (91.3) | N/A | 56.4 | 60.2 |
| 0 pH = 4.5 | 13.0 (43.5) | 44.2 (3.8) | 2.9 (82.7) | N/A | 60.1 | 64.7 |

Figure 18:
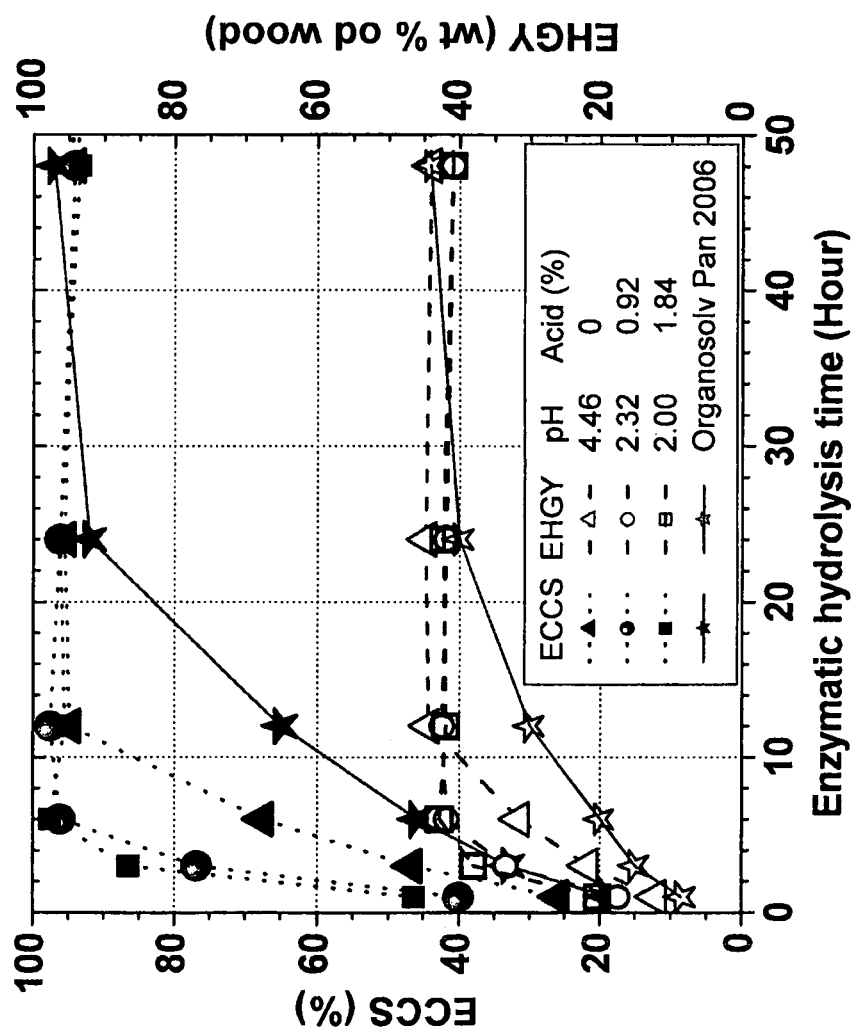
FIG. 18. Comparisons of time-dependent enzymatic cellulose conversion of substrate (ECCS) and enzymatic hydrolysis glucose yield (EHGY) between SPORL and organosolv pretreatments of Aspen.

FIG. 18 shows the time-dependent ECCS and EHGY wt % of untreated aspen using SPORL process in comparison to those reported by Pan et al. (2006) using Organosolv pretreatment. The digestibility of the substrates from SPORL is better than that from organosolv with only 4% sodium bisulfite charge on Aspen pretreated at the same temperature of 180° C. but with short pretreatment time than that of the Organosolv. The enzyme dosage used in SPORL was similar to that used by Pan et al. (2006), about 20 FPU/g cellulose. In SPORL process, over 90% ECCS can be achieved within 4-8 hours of enzymatic hydrolysis, and EHGY over 44 wt % wood were obtained in about 10 hours of hydrolysis, which is equivalent to overall cellulose conversion based on wood of 82%. The improved digestibility of the substrate can help to reduce enzyme application. It can also improve the efficiency of fermentation using the simultaneous saccharification and fermentation (SSF) process, the currently preferred process by the biorefining industry. Therefore the present process can also improve the economics for biorefining hardwood.

Figure 19:
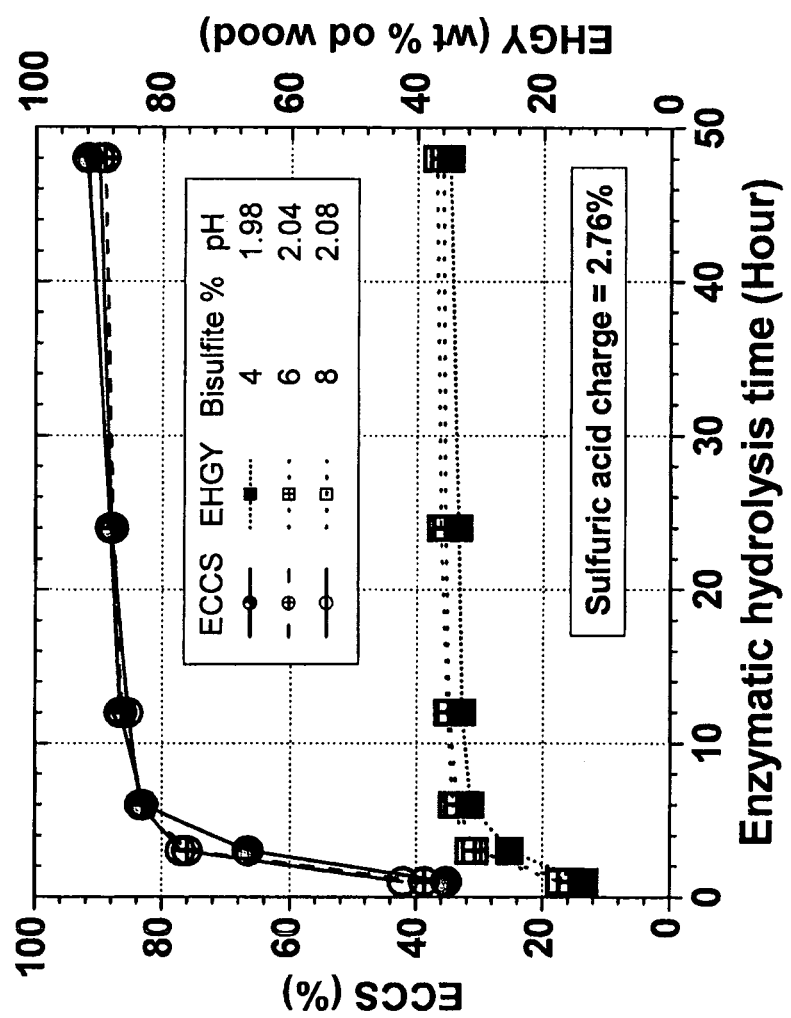
FIG. 19. Time-dependent enzymatic cellulose conversion of substrate (ECCS) and enzymatic hydrolysis glucose yield (EHGY) from Maple with SPORL.

Excellent enzymatic cellulose conversion of substrate and EHGY were also obtained from Maple with SPORL as shown in FIG. 19.

Example 9

Application to Agricultural Biomass

SPORL also significantly improved the digestibility of corn stover. Table 9 shows that satisfactory cellulose conversion can be achieved within 6-12 hours of enzymatic hydrolysis using a normal enzyme dosage 15 FPU/g substrate of Celluclast 1.5 L and 22.5 CBU of Novozyme 188. The initial pH value of the pretreatment liquor of these pretreatments was about 1.9. Conversion efficiency may be further improved by adjusting to a higher pH of around 2.2 based on the results from spruce and red pine. Similar conversion was achieved at 24 hours using dilute acid pretreatment. With the improved digestibility, the inventors reduced enzyme dosage by one-half to 7.5 FPU/g of od substrate Celluclast 1.5 L and 11.2 CBU/g of od substrate of Novozyme 188. Equivalent cellulose conversion to that of the acid only pretreatment was achieved within 24 hours.

TABLE 9

Time-dependence of enzymatic cellulose conversion of corn stover substrate from SPORL under different bisulfite and enzyme dosage

| | Acid charge on od wood (%) | | | |
|---|---|---|---|---|
| Enzymatic Hydrolysis Time (hour) | Acid only = 3.68% | Acid = 3.68% Bisulfite 3% | Acid = 3.68% Bisulfite 6% | Acid = 3.68 Bisulfite 3% Half enzyme dosage |
| 1 | 36.7 | 38.2 | 37.2 | 24.5 |
| 3 | 63.0 | 70.5 | 71.2 | 51.1 |
| 6 | 73.3 | 82.0 | 81.7 | 64.9 |
| 12 | 81.4 | 87.2 | 83.8 | 76.9 |
| 24 | 85.1 | 90.1 | 86.6 | 85.0 |
| 48 | 87.4 | 90.1 | 88.7 | 88.6 |
| 72 | 88.1 | 93.8 | 90.1 | 90.8 |

Example 10

Application to Steam Explosion Pretreatment

Acid (such as using $SO_2$ or sulfuric acid)—catalyzed steam explosion pretreatment has been applied to both softwood and hardwood (Galbe and Zacchi, 2002, De Bari et al., 2007). SPORL can be easily implemented to steam explosion simply by adding either bisulfite when sulfuric acid is used or hydroxide when $SO_2$ is used. Based on the results presented above, the inventors contemplate that SPORL with steam explosion will produce excellent digestibility for woody/non-woody biomass.

Example 11

Application to Waste Paper

Figure 20:
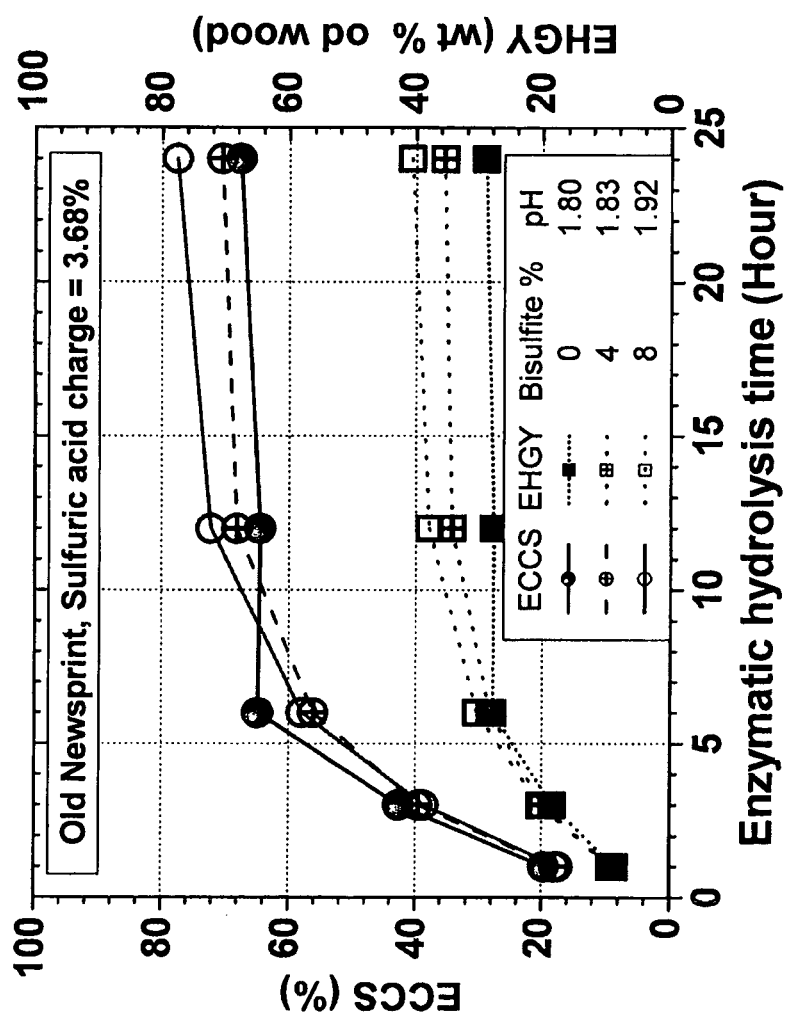
FIG. 20. Time-dependent enzymatic cellulose conversion of substrate (ECCS) and enzymatic hydrolysis glucose yield (EHGY) from Old Newsprint Papers (ONP) with SPORL.

SPORL was applied to waste paper (printed newsprint from Madison Newspaper). It improved the digestibility of waste paper compared to the traditional acid pretreatment as shown in FIG. 20. The cellulose conversion did not achieve 90%, which is probably due to the low pH (pH below 1.92) applied in SPORL. Based on the data for spruce and red pine, optimal conversion may be achieved at pH around 2.2 for pretreatment temperature of 180° C. However, FIG. 20 did show that cellulose conversion increased when sodium bisulfite was increased from 0 to 8%. Acid only pretreatment was not able to achieve the cellulose conversion as those with bisulfite. ECCS of the acid only pretreatment was 10% lower than achieved under SPORL with bisulfite charge 8%. EHGY was about 40 wt % of untreated newspaper.

Example 12

Evaluation of the Production of Fermentation Inhibitory Species during SPORL Pretreatment Under acid pretreatment conditions at high temperature, hydroxymethyl furfural (HMF) will be produced from hexosans and furfural will be produced from pentosans (Larsson et al., 1999). Both HMF and furfural are species that inhibit the normal fermentation process. The total amounts of HMF and furfural formation were determined by multiplying the HPLC-measured HMF and furfural concentrations in the pretreatment spent liquor and the liquor volume (including the moisture in the original wood chips). The HMF and furfural formations from 1 g of original od wood chips were reported in Table 10. HMF and furfural decreased with increasing bisulfite. An explanation is that at the same acid charge (1.8%), more bisulfite resulted in a higher pH, which depressed the decomposition of the sugars to HMF and furfural. The variation in pH of the pretreatment liquor resulted in the difference in the combined severity factors (Chum et al., 1990) when the pretreatment temperature and duration time were the same for all the runs listed. The amounts of HMF and furfural formation were only 7 and 3 mg/g of untreated od wood, respectively, at bisulfite and acid charges of 9% and 1.84% (combined severity factor of about 1.4) when glucose yield was maximized (FIGS. 10-11). The productions of HMF and furfural are significantly lower than those found using dilute acid pretreatments. The amounts of HMF and furfural formation were about 50 and 25 mg/g untreated od wood during acid catalyzed steam pretreatment of spruce, respectively, when glucose yields were maximized at a combined severity factor between 3.0 and 3.4 (Larsson et al., 1999).

Figure 21:
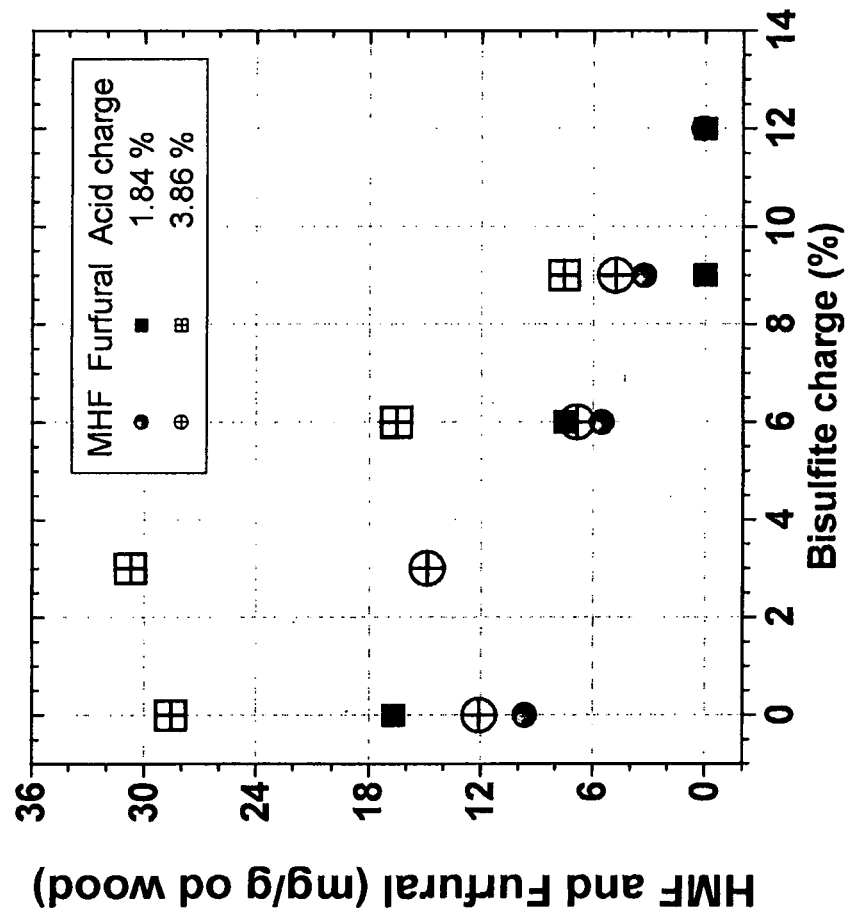
FIG. 21. Effect of bisulfite dosage on the production of HMF and Furfural during pretreatment of spruce at a temperature of 180° C.

The data from spruce in Table 10 were plotted in FIG. 21 to show the effect of sodium bisulfite charge on the production of HMF and furfural during the pretreatment of spruce. At a temperature of 180° C., more bisulfite resulted in less HMF and furfural. It should be noted that acid pretreatments are usually conducted at temperatures higher than 180° C., therefore the production of HMF and furfural will likely be higher than that shown in FIG. 21. Even at a temperature of 180° C., a clean-up process will be needed to remove HMF and furfural before fermentation based on the number reported in FIG. 21 for the acid only process. However, at a bisulfite charge of 9%, the amount of HMF and furfural is low enough that a separation process is not required prior to fermentation. The lower production of HMF and furfural is another advantage of the present invention, which is favorable to the fermentation of cellulose and hemicellulose sugars in the pretreatment spent liquor.

Figure 22:
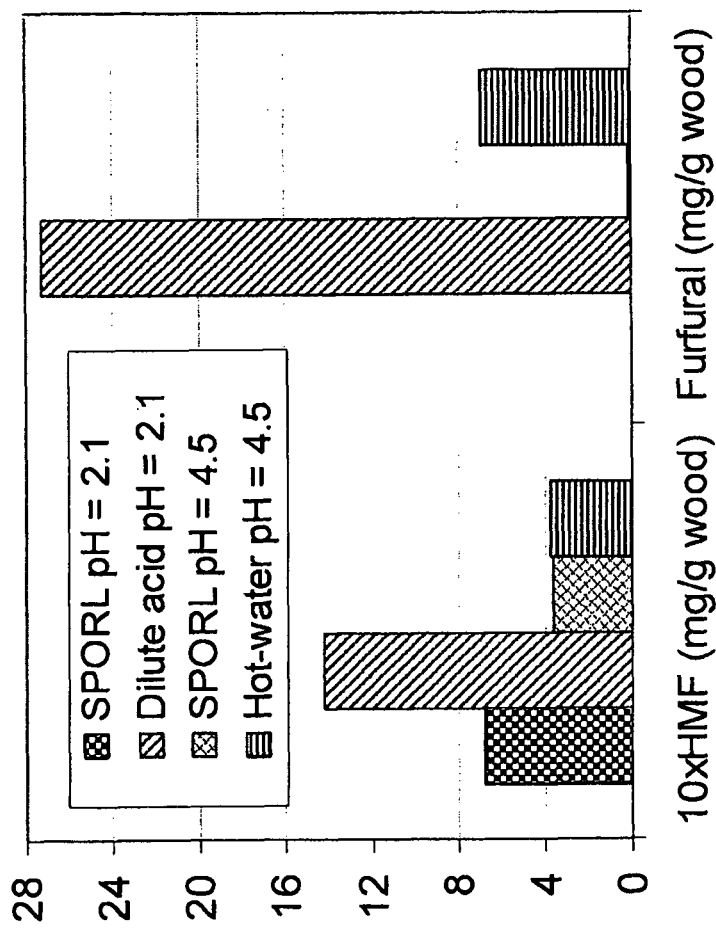
FIG. 22. Comparisons of the production of HMF and furfural among SPORL, dilute acid and hot-water pretreatment of short rotation Aspen at 180° C.
Figure 23:
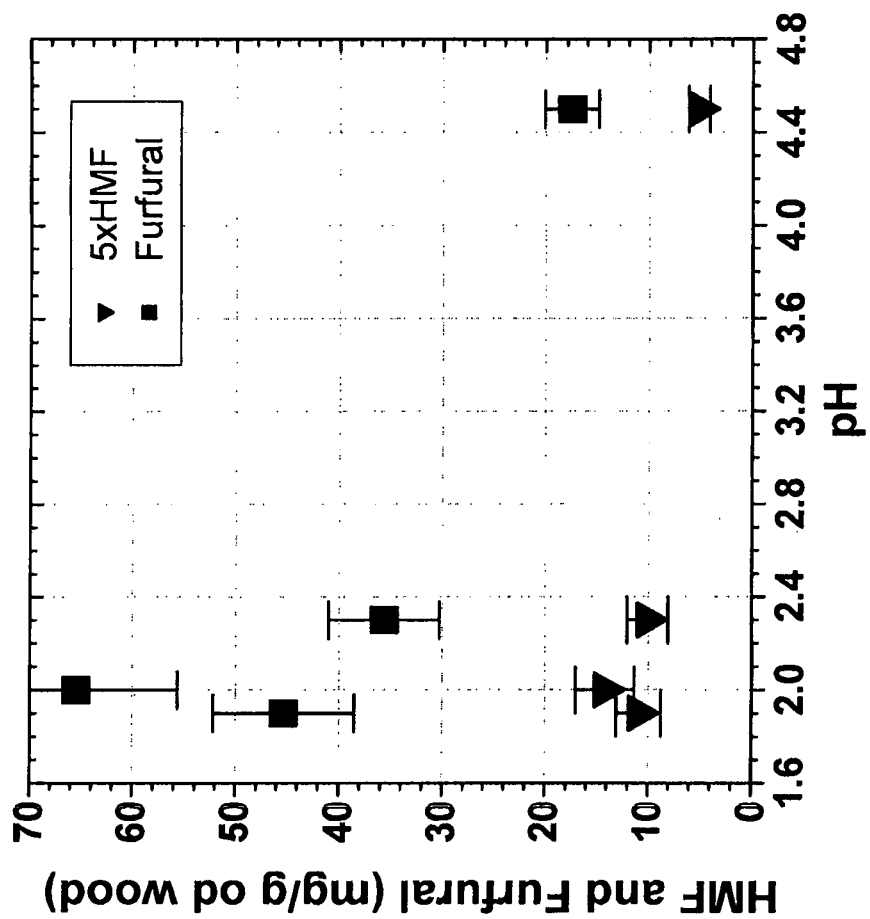
FIG. 23. Effect of pH on the production of HMF and furfural from SPORL pretreatment of Eucalyptus at 180° C.

Similar results on reduction of HMF and Furfural were obtained from SPORL of Eucalyptus and Aspen. FIG. 22 compares the production of HMF and furfural during SPORL, dilute acid, and hot water pretreatments of eucalyptus. HMF productions are very low for all four pretreatments carried out due to the limited amount of hexosans available in the pretreatment liquor. Furfural production is almost zero for the two SPORL pretreatments (the number are too low to be seen from FIG. 22), while both dilute acid and hot water pretreatments produced a fair amount of furfural even at the same pH value as their respective SPORL pretreatment. FIG. 23 shows the effect of pH (acid addition from 2.76% to 0 on wood) on the production of HMF and furfural in SPORL pretreatment of aspen at 180° C. with sodium bisulfite charge of 4% on wood. Because xylan is the dominate hemicellulose of hardwoods, HMF production should be low due to limited amount of hexosans. Similar to what occurs in dilute acid pretreatment, furfural production decreases significantly as pH increases in SPORL. Furfural production is less than 20 mg/g of od wood at pH 4.5, suggesting that SPORL pretreatment without acid addition not only avoided the problem of equipment corrosion and eliminated the need for neutralization for enzymatic hydrolysis, but also produced a favorable stream for fermentation.

TABLE 10

Effect of sodium bisulfite charge on the formation of HMF and furfural during the SPORL at T = 180° C. for t = 30 min

| Sulfuric acid charge on od wood (%) | Bisulfite charge on od wood (%) | Initial liquor pH | Combined severity factor$^a$ | HMF (mg/g od wood) | Furfural (mg/g od wood) |
|---|---|---|---|---|---|
| Spruce | | | | | |
| 1.84 | 0 | 2.09 | 1.74 | 9.64 | 16.68 |
|  | 6 | 2.25 | 1.58 | 5.55 | 7.51 |
|  | 9 | 2.42 | 1.41 | 3.27 ± 1.2 | 6.5 ± 3.0 |
|  | 12 | 2.54 | 1.29 | 0.08 | 0 |
| 3.68 | 0 | 1.90 | 1.93 | 12.1 | 28.55 |
|  | 3 | 1.95 | 1.88 | 14.89 ± 3.5 | 30.73 ± 7.7 |

TABLE 10-continued

Effect of sodium bisulfite charge on the formation of HMF and furfural during the SPORL at T = 180° C. for t = 30 min

| Sulfuric acid charge on od wood (%) | Bisulfite charge on od wood (%) | Initial liquor pH | Combined severity factor[a] | HMF (mg/g od wood) | Furfural (mg/g od wood) |
|---|---|---|---|---|---|
| | 6 | 2.04 | 1.79 | 6.86 | 16.55 |
| | 9 | 2.16 | 1.67 | 4.81 | 7.55 |
| | | | Red pine | | |
| 3.68 | 6 | 2.06 | 1.77 | 5.21 | 7.33 |
| | 9 | 2.21 | 1.62 | 3.43 | 1.7 |
| | 12 | 2.27 | 1.56 | 2.46 | 2.9 |

[a] Combined severity factor $= \log\left[t \cdot \exp\left(\frac{T-100}{14.75}\right)\right] - \mathrm{pH}$ (Chum et al., 1990).

Example 13

Monomer Sugar Recovery from Spent Pretreatment Liquor (Hydrolysate)

Figure 24:
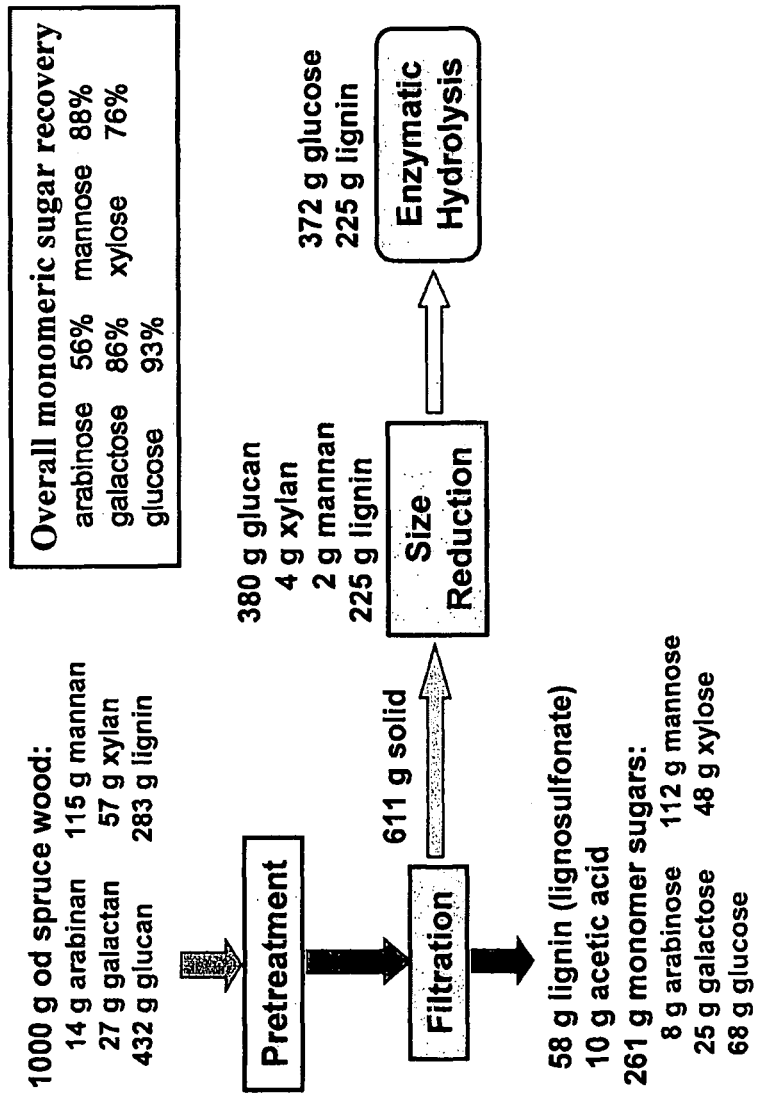
FIG. 24. Preliminary mass balance of the SPORL process at 180° C. for 30 min with sodium bisulfite and sulfuric acid charge of 9% and 3.68%, respectively, on od (oven-dry) spruce.

Preliminary mass balance of the SPORL process at 180° C. with sodium bisulfite and sulfuric acid charges on od wood of 9% and 3.68%, respectively, is shown in FIG. 24. For 1 kg of untreated spruce wood, total yield of monomeric sugars in the pretreatment spent hydrolysate was 261 g, which includes 8, 25, 48, and 112 g, respectively, of monomeric arabinose, galactose, xylose, and mannose and an additional 68 g of glucose mainly from the dissolved glucan by acidic hydrolysis and glucose residues in hemicelluloses during the SPORL pretreatment. These results correspond to overall sugar recovery (including 372 g glucose from enzymatic hydrolysis) of the major saccharides (arabinose, galactose, xylose, mannose, and glucose) of about 54%, 86%, 76%, 88%, and 93%, respectively, based on original untreated spruce wood. The lignosulfonate content is estimated from the balance of lignin in the substrate.

Example 14

Energy Consumption in Size Reduction

The pretreatment experiments using a 23-L digester with 2000-g wood chip capacity allowed us to conduct disk refining on the 12-in. disk refiner, which can record electric energy consumption used for size reduction. The results are summarized in Table 11. The specific mechanical refining energies have been evaluated in numerous mechanical pulping studies in the past decade and were found to be very close to those in pilot- and commercial-scale mechanical pulping. The measurement error with duplicates was within 2%. Therefore, the refining energy consumption disclosed in this invention can be applied to future commercial production. With electric energy input of only 19 Wh/kg od untreated spruce wood, the pretreated wood chips with sulfuric acid and bisulfite charges of 3.68% (pH 2.16) and 9%, respectively, can be easily pulverized with a mean fiber length around 0.3 mm. The refining energy consumption of 19 Wh/kg was significantly lower than those of typical mechanical, thermomechanical, chemo-mechanical, and semichemical pulping (Kurdin, 1980; Marteny, 1980), indicating that the SPORL pretreatment is substantially effective at softening the wood chips and saving energy in size reduction. The softening of wood chips is owing to dissolution of hemicellulose, partial delignification, and lignin sulfonation. Using the data in Table 11 and glucose yield in FIG. 11, the calculated EHGY on unit electric energy consumption using the methodology described previously (Zhu et al., 2009a) was 19.6 g glucose/Wh.

TABLE 11

Effect of chemical pretreatment on mechanical size reduction

| | |
|---|---|
| Sulfuric acid charge on od wood (%) | 3.68 |
| | (pH 2.16) |
| Sodium bisulfite charge on od wood (%) | 9 |
| Electric energy used in mechanical refining (Wh/kg od chips) | 19 |
| Arithmetic mean length (mm) | 0.320 |
| Arithmetic mean width (mm) | 0.0306 |
| EHGY (% wt od spruce wood) | 37.2 |
| EHGY (g/Wh) | 19.1 |

Example 15

Analysis of Biomass Substrate Specific Surface

Depending on the size-reduction process, the morphology of a biomass substrate can be very different (FIG. 6). In certain aspects of the present invention, the particle form is referred to as a biomass substrate with an aspect ratio close to unity; therefore, a sphere approximation of the substrate can be made. In contrast, the fiber form is referred to as a substrate with very large aspect ratios similar to fibers; therefore, the substrate can be approximated as either a cylinder or a ribbon. The rationale for the cylinder assumption is supported by the scanning electron microscope (SEM) images of substrates from disk and hammer millings (FIG. 6).

For the particle substrate, the physical dimension is often represented by its mean diameter. The particle size distribution of a given substrate can be measured by a variety of techniques. The traditional techniques are the sieve and screen methods. Modern techniques include imaging analysis. Imaging techniques measure projection dimensions of a particle. Once the particle size distribution is obtained, there are several statistical ways to calculate the mean particle size. Particles are assumed to be spherical. The arithmetic mean $D_{10}$, Sauter mean $D_{32}$, and volume (mass) mean $D_{30}$ diameters can be calculated (Lefebvre, 1989; Sowa, 1992). Neglecting particle surface roughness, the external volumetric specific surface, $S_p^V$, can be estimated according to the equation $$S_p^V = \frac{A_p}{V_p} = 6 \cdot \frac{\sum_i n_i d_i^2}{\sum_i n_i d_i^3} = \frac{6}{D_{32}} \quad (1)$$

where $A_p$, $V_p$ are the total surface area and volume of the particles, respectively, and $n_i$ is the number of particles in size bin i with representative diameter $d_i$. D32 is also called Sauter mean diameter (SMD).

By measuring the oven dry weight of the sample, $m_p$, before analysis, the specific surface, $S_P$, of the sample can be determined using the following expression when each fiber (particle) in the sample is accounted for and measured:

$$S_p = \frac{A_p}{m_p} = \frac{\pi \sum_i n_i d_i^2}{m_p} \quad (2)$$

Most existing size-reduction technologies or processes produce fibrous substrates with very large aspect ratios in a range of about 5-200. Neglecting surface roughness and assuming cylindrical shape, the volumetric specific surface of fibers, $S_f^V$, can be estimated according to the equation $$S_f^V = \frac{A_f}{V_f} = \frac{2\sum_i n_i(d_i^2 + 2 \cdot d_i \cdot L_i)}{\sum_i n_i d_i^2 \cdot L_i} = \frac{4\sum_i n_i d_i (L_i + d_i/2)}{\sum_i n_i L_i \cdot d_i^2} \quad (3)$$

For most fibers with aspect ratios greater than 5, Eq. (3) can be approximated to $$S_f^V \approx 4 \cdot \frac{\sum_i n_i L_i \cdot d_i}{\sum_i n_i L_i \cdot d_i^2} = \frac{4}{D_{L21}} \quad (4)$$

where $A_f$, $V_f$ are the total surface area and volume of the fibers, respectively. $n_i$ is the number of fibers in fiber group i. $L_i$ and $d_i$ are the representative length and diameter of fiber group i, respectively. Assuming the sample can be characterized by K diameter bins and J length bins, then the total fiber groups I=K×J. One can always use two summations with different subscripts, k and j, to differentiate diameter bins from length bins in Eqs. (3) and (4). $D_{L21}$ is a fiber length weighted-surface-length mean fiber diameter or "width." The difference in volumetric specific surface between Eqs. (3) and (4) is very small, varying from 1% to 5% for the samples used in this invention, when calculated using the data measured by the wet imaging method.

Similarly, the specific surface of the sample, $S_f$, can be determined by measuring the oven dry weight of the sample, $m_f$, before analysis when each fiber (particle) in the sample is accounted for and measured:

$$S_f = \frac{A_f}{m_f} = \frac{\pi}{2} \frac{\sum_i n_i(d_i^2 + 2 \cdot d_i \cdot L_i)}{m_f} \approx \pi \frac{\sum_i n_i \cdot d_i \cdot L_i}{m_f} \quad (5)$$

It should be pointed out that the volumetric specific surface of prolate spheroid-shape fibers with large aspect ratio is very close to the results from Eqs. (4) and (5) based on mathematical analysis.

Fibers have lumens; however, a hollow cylindrical fiber with a very thin wall thickness is a more realistic assumption. If the wall thickness is ignored, then the specific surface is simply two times the specific surface of a cylinder (Eqs. (3) and (5)). Due to the difficulties in determining the internal structural surface of the lumens with existing technology, the inventors simply neglect the lumen surface in the examples. This simplification can be reasonable for substrates in single fiber form such as those disk-milled (FIGS. 6C-D) and very finely hammer-milled (FIG. 6B), because some parts of a lumen are often collapsed during the size-reduction process, making the lumen surface not easily accessible to enzymes. Furthermore, the pore depth effect suggested by Sangseethong et al. (1998) and Levenspiel (1972) can limit enzyme accessibility into the internal surfaces of pores or lumens. However, for substrates mainly consisting of fiber bundles, such as some hammer-milled samples (FIG. 6A), it is not appropriate to neglect the internal lumen surfaces in determining specific surface because the lumens may not collapse in processing. Unfortunately, it is very difficult to find a simple technique to determine lumen internal surfaces of fiber bundles that can be easily implemented for rapid and routine lab analysis using existing technology.

According to Eqs. (3)-(5), at least two parameters are used to characterize fiber-form substrate. If only one parameter has to be used, Eqs. (1) and (4) clearly indicate that SMD or D32 should be used to measure the size-reduction efficiency of equipment or processes (such as sawing) that produces spherically shaped particles with aspect ratios close to unity. The length-weighted mean surface-length diameter or width, $D_{L21}$, should be used to measure the size-reduction efficiency of equipment or processes, such as disk or hammer milling, that produce cylindrically shaped fibers with large aspect ratios (>5). Besides the unaccounted lumen internal structural surface, the geometric shape of the cross section of fibers also affects the accuracy of the cylinder specific surface model (Eqs. (3)-(5)). For a given imaging measured projection diameter, the deviation in specific surface from a cylinder is about 40% for fibers with a diamond cross section. The error increases to about 450% for a ribbon fiber with a thickness of 1/10 of the measured projection diameter. Fortunately, most fibers produced from disk refining are not all ribbon like (FIGS. 6C-D).

Figure 25:
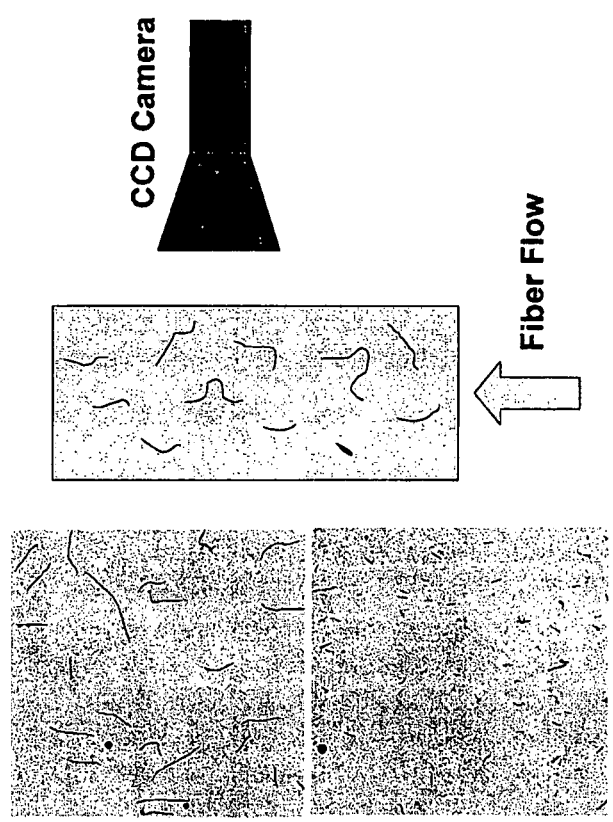
FIG. 25. Schematic diagram of a wet imaging system.
Figure 26:
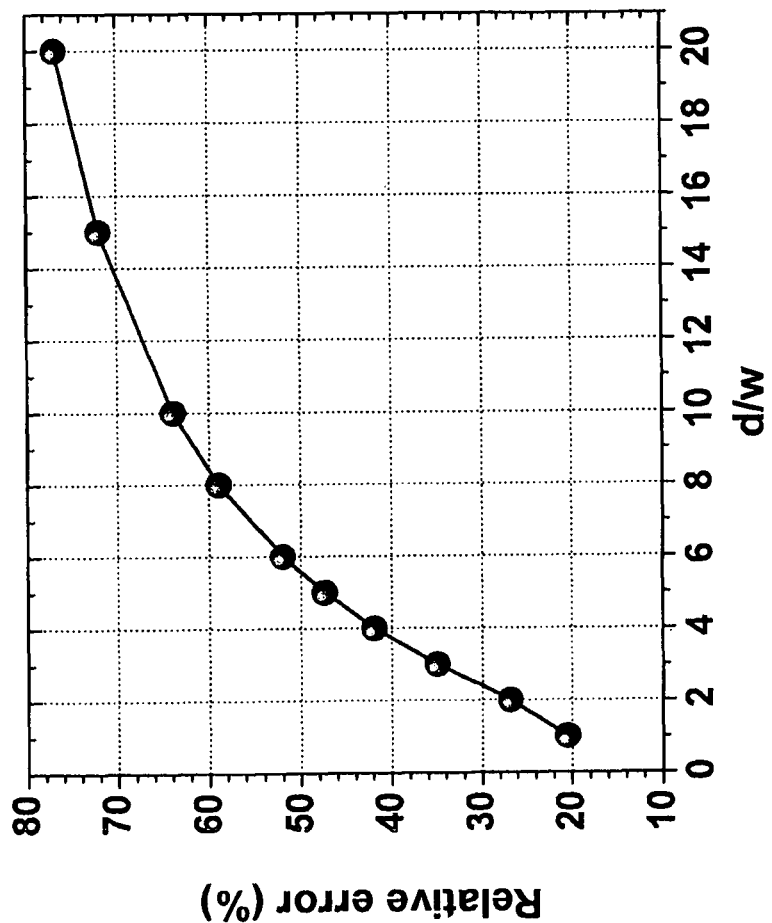
FIG. 26. Predicted measurement errors of ribbon-shaped fibers using the wet imaging technique described in the present invention.

The present inventors further contemplates to use wet imaging techniques, such as those already in the market place, to measure the two dimensions of a fiber for using Eqs. listed in Table 12 and 13. FIG. 25 shows one embodiment of such a system. In wet imaging, fibers are suspended and flowing in a channel. Fibers can freely spin, therefore, the probability of imaging the different orientations of a non-cylindrical fibers, e.g., the dimensions in width and thickness of a ribbon fiber, are the same. So, the error in mean specific surface calculated using the cylinder model can be significantly reduced on average, when tens of thousands fibers were measured. To quantify the advantage of wet imaging technique, the present inventors calculated the reduced measurement errors in substrate specific surface assuming equal probability in imaging orientations due to free spinning of substrate fibers. FIG. 26 shows the predicted measurement errors in specific surface of ribbon fibers (with rectangular cross sectional area) of different width (d) over thickness (w) ratio using the cylinder model.

Figure 27:
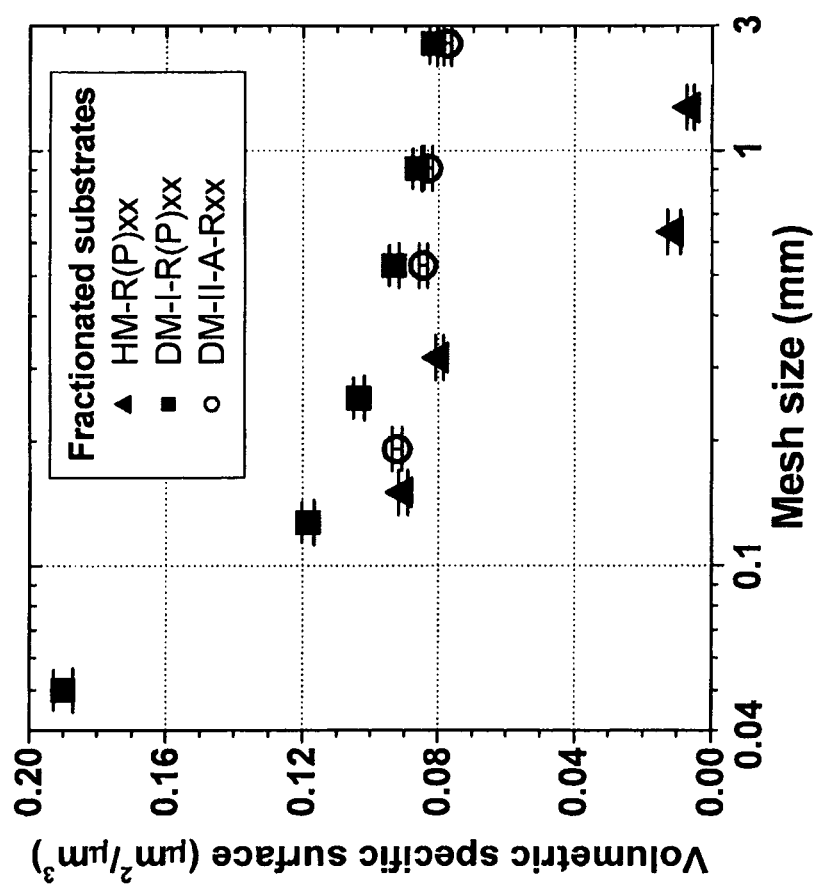
FIG. 27. Correlations of mesh size with substrate specific surface for disk- and hammer-milled substrates.

The inventors used a pulp sample from disk milling at 2.4 bar and 134° C. (DM-I) and a second sample from hammer milling with very different morphology (FIGS. 6A-D) to illustrate the various cross sectional differences, shapes, and areas of wood fibers. The images shown are fractionated substrates as described below. Table 14 and 15 show the mean values of the various measures of the fractions, including specific surface, derived from these two pulp samples. The data in the two tables indicate that mesh size of each fraction is very different from wet imaging measured mean length and width. Although the mesh size correlates to the mean length, mean width, and even mean specific surface, the correlations for the disk-milled fractions differ significantly from those for the hammer-milled fractions (FIG. 27). In other words, the correlation between mesh size and other size measures of substrates including specific surface depends on the substrates morphology and how the substrates were produced. The disk milling process breaks wood chips mainly into fibers, even for the mesh size 28 and 48 samples (FIGS. 6C-D). Hammer milling fiberizes only a small fraction of wood chips in the examples. For example, the particles in HM-R80 sample are essentially fiber bundles (FIG. 6A). Only the HM-P80 sample was fiberized (FIG. 6B). Further examining the distribution of various measures of the pulp fractions using MorFi indicates that the fractionated substrates have narrow ranges of length, diameter, and width. Similar results were obtained for the hammer-milled substrates fractionated by dry sieving.

TABLE 12

Equations to calculate the average (volumetric) specific surface of a substrate using fiber models of different cross section. The measured width (diameter), $d_i$ is the image projection dimension.

| Fiber with Cross section | Circle | ELT-I | ELT-II | Square | Diamond |
|---|---|---|---|---|---|
| Imaging Projection | ○ | △ | ▽ | □ | ◇ |
| $S_f^V$ | $4\sum_i \dfrac{n_i d_i(L_i + d_i/2)}{\sum_i n_i L_i \cdot d_i^2}$ $\approx 4 \cdot \dfrac{\sum_i n_i \cdot d_i \cdot L_i}{\sum_i n_i L_i \cdot d_i^2}$ $= \dfrac{4}{D_{L21}}$ | $6\sum_i \dfrac{n_i d_i(L_i + d_i/3)}{\sum_i n_i L_i \cdot d_i^2}$ $\approx 6 \cdot \dfrac{\sum_i n_i \cdot d_i \cdot L_i}{\sum_i n_i L_i \cdot d_i^2}$ $= \dfrac{6}{D_{L21}}$ | $4\sqrt{3}\sum_i \dfrac{n_i d_i(L_i + d_i/2/\sqrt{3})}{\sum_i n_i L_i \cdot d_i^2}$ $\approx 4\sqrt{3} \cdot \dfrac{\sum_i n_i \cdot d_i \cdot L_i}{\sum_i n_i L_i \cdot d_i^2}$ $= \dfrac{4\sqrt{3}}{D_{L21}}$ | $4\sum_i \dfrac{n_i d_i(L_i + d_i/2)}{\sum_i n_i L_i \cdot d_i^2}$ $\approx 4 \cdot \dfrac{\sum_i n_i \cdot d_i \cdot L_i}{\sum_i n_i L_i \cdot d_i^2}$ $= \dfrac{4}{D_{L21}}$ | $4\sqrt{2}\sum_i \dfrac{n_i d_i(L_i + d_i/2/\sqrt{2})}{\sum_i n_i L_i \cdot d_i^2}$ $\approx 4\sqrt{2} \cdot \dfrac{\sum_i n_i \cdot d_i \cdot L_i}{\sum_i n_i L_i \cdot d_i^2}$ $= \dfrac{4\sqrt{2}}{D_{L21}}$ |
| $S_f$ | $\dfrac{\pi}{2} \sum_i \dfrac{n_i(d_i^2 + 2 \cdot d_i \cdot L_i)}{m_f}$ $\approx \pi \dfrac{\sum_i n_i \cdot d_i \cdot L_i}{m_f}$ $D_{L21} = \dfrac{\sum_i n_i L_i \cdot d_i^2}{\sum_i n_i L_i \cdot d_i}$ | $2\sqrt{3}\sum_i \dfrac{n_i d_i(L_i + d_i/3)}{m_f}$ $\approx 2\sqrt{3} \dfrac{\sum_i n_i \cdot d_i \cdot L_i}{m_f}$ $D_{L21} = \dfrac{\sum_i n_i L_i \cdot d_i^2}{\sum_i n_i L_i \cdot d_i}$ | $3\sum_i \dfrac{n_i d_i(L_i + d_i/2/\sqrt{3})}{m_f}$ $\approx 3 \dfrac{\sum_i n_i \cdot d_i \cdot L_i}{m_f}$ $D_{L21} = \dfrac{\sum_i n_i L_i \cdot d_i^2}{\sum_i n_i L_i \cdot d_i}$ | $4\sum_i \dfrac{n_i d_i(L_i + d_i/2)}{m_f}$ $\approx 4 \dfrac{\sum_i n_i \cdot d_i \cdot L_i}{m_f}$ $D_{L21} = \dfrac{\sum_i n_i L_i \cdot d_i^2}{\sum_i n_i L_i \cdot d_i}$ | $2\sqrt{2}\sum_i \dfrac{n_i d_i(L_i + d_i/2/\sqrt{2})}{m_f}$ $\approx 2\sqrt{2} \dfrac{\sum_i n_i \cdot d_i \cdot L_i}{m_f}$ $D_{L21} = \dfrac{\sum_i n_i L_i \cdot d_i^2}{\sum_i n_i L_i \cdot d_i}$ |
| Characteristic Size | | | | | |
| Relative difference in $S_f^V$ to Circle | | 50% | 73% | 0 | 41% |
| Relative difference in $S_f$ to Circle | | 10.3% | −4.5% | 27% | −10% |

TABLE 13

Equations to calculate the average (volumetric) specific surface of a substrate using columns of different cross sections of rectangles or ellipses with different ratios of width to thickness or major to minor axis, x = d/w

| Fiber with Cross section | Rectangle d/w = x | Ellipse d/w = x |
|---|---|---|
| Imaging Projection → | ▯ | ⬭ |
| $S_f^v$ | $\dfrac{2\sum_i n_i d_i[(x+1)L_i + d_i]}{\sum_i n_i L_i \cdot d_i^2}$ | $\dfrac{2\sum_i n_i d_i\{[3(x+1) - \sqrt{(3x+1)(x+3)}]L_i + d_i\}}{\sum_i n_i L_i \cdot d_i^2}$ |
|  | $\approx 2(x+1) \cdot \dfrac{\sum_i n_i L_i \cdot d_i}{\sum_i n_i L_i \cdot d_i^2}$ | $\approx 2[3(x+1) - \sqrt{(3x+1)(x+3)}]\dfrac{\sum_i n_i d_i L_i}{\sum_i n_i L_i \cdot d_i^2}$ |
|  | $= \dfrac{2(x+1)}{D_{L2l}}$ | $= \dfrac{2[3(x+1) - \sqrt{(3x+1)(x+3)}]}{D_{L2l}}$ |
| $S_f$ | $\dfrac{2\sum_i n_i d_i[(x+1)L_i + d_i]/x}{m_f}$ | $\dfrac{\pi}{2}\dfrac{\sum_i n_i d_i\{[3(x+1) - \sqrt{(3x+1)(x+3)}]L_i + d_i\}/x}{m_f}$ |
|  | $\approx 2\left(1 + \dfrac{1}{x}\right)\dfrac{\sum_i n_i \cdot d_i \cdot L_i}{m_f}$ | $\approx \dfrac{\pi}{2x}[3(x+1) - \sqrt{(3x+1)(x+3)}]\dfrac{\sum_i n_i d_i L_i}{m_f}$ |
| Characteristic size | $D_{L2l} = \dfrac{\sum_i n_i L_i \cdot d_i^2}{\sum_i n_i L_i \cdot d_i}$ | $D_{L2l} = \dfrac{\sum_i n_i L_i \cdot d_i^2}{\sum_i n_i L_i \cdot d_i}$ |
| Relative difference in $S_f^V$ to Circle | (x − 1)/2 * 100% | x = 0.4, 2.5, 0.1, 10<br>−26.7%; 83.1%; −35.4%; 546.3% |
| Relative difference in $S_f$ to Circle | x = 0.4, 2.5,<br>122.8%, −10.9%<br>x = 0.1, 10<br>600% −30% | x = 0.4, 2.5, 0.1, 10<br>83.1%, −26.7%; 546.3%;<br>−35.4%; |

TABLE 14

Different measures of mean size for a set of fractionated disk-milled substrates

| Fractions | Mesh size | Arithmetic mean length (mm) | Arithmetic mean diameter (width, μm) | Mean aspect ratio | Mean volumetric specific surface (1/μm) |
|---|---|---|---|---|---|
| DM-I-R14 | >1.814 (mm) | 1.939 | 44 | 44.1 | 0.0817 |
| DM-I-R28 | 0.907-1.588 | 1.817 | 42.4 | 42.9 | 0.0864 |
| DM-I-R48 | 0.529-0.907 | 1.286 | 40.3 | 31.9 | 0.0931 |
| DM-I-R100 | 0.254-0.529 | 0.723 | 36.3 | 19.9 | 0.1035 |
| DM-I-R200 | 0.127-0.254 | 0.403 | 30.7 | 13.1 | 0.1184 |
| DM-I-P200 | <0.127 | 0.269 | 24.2 | 11.1 | 0.19 |

TABLE 15

Different measures of mean size for a set of fractionated hammer-milled substrates

| Fractions | Mesh size | Arithmetic mean length (mm) | Arithmetic mean diameter (width, μm) | Mean aspect ratio | Mean volumetric specific surface (1/μm) |
|---|---|---|---|---|---|
| HM-R20 | >1.27 (mm) | 2.664 | 230.7 | 11.6 | 0.00612 |
| HM-R40 | 0.635-1.27 | 1.920 | 201.5 | 9.5 | 0.01092 |
| HM-R80 | 0.318-0.635 | 0.531 | 41.1 | 12.9 | 0.07972 |
| HM-P80 | <0.318 | 0.424 | 36.6 | 11.6 | 0.09044 |

Example 16

Material and Methods for Using Specific Surface to Evaluate Pretreatment Efficiency The major dependent variables are glucose yield and energy consumption in size reduction. The major independent variables are milling process, pretreatment process, and fiber fractionation. Table 16 lists the experimental design and all the substrates produced through this design. The milling processes are labeled as HM or DM. The chemical pretreatment processes are labeled as A, B, C (discussed later in the text). The fractionated substrates are represented by Rxx (retained) or Pxx (pass) with xx being the mesh size.

A. Materials

Fresh spruce chips were the same as described in Example 1. The same enzymes of Celluclast 1.5 L (cellulase) and Novozym 188 (β-glucosidase) as described in Example 1 were used.

B. Mechanical Size Reduction

Mechanical size reduction was conducted using a laboratory 28-cm hammer mill (Montgomery-Ward ModelWB9A, 5 HP, 3600 rpm) and a 12-inch disk refiner (Andritz Sprout-Bauer Pressurized Refiner, Andritz Sprout, Muncy, Pa.) at the US Forest Service, Forest Products Laboratory, Madison, Wis. Three types of disk milling were conducted, DM-I, DM-II, and DM-III. The electric energy consumption in disk milling was recorded. The standard deviation was less than

TABLE 16

List of experimental conditions and the substrates produced

| Milling Process | Milling Conditions T, P, disk plate gap (mm) | Milling energy (Wh/kg) | Chemical Pretreatment | Fractionation | Substrates |
|---|---|---|---|---|---|
| Hammer Milling | Atmospheric | | No | Yes | HM-R20, HM-R40, HM-R80, HM-P80, |
| Disk Milling-I | 134° C., 2.4 bar 0.25, chip pre-steamed | 460 | No | No | DM-I |
| | | | | Yes | DM-I-R14, DM-I-R28, DM-I-R48, DM-I-R100, DM-I-R100, DM-I-R200, DM-I-P200 |
| Disk Milling-II | 166° C., 7.2 bar 0.06 | 151 | No | No | DM-II |
| | | | | Yes | DM-II-R14, DM-II-R28, DM-II-R48, DM-II-R100 + R200 |
| | | 106 | A on wood chips then milling | No | DM-II-A |
| | | | A on pulp after milling of chips | Yes | DM-II-A-R14, DM-II-A-R28, DM-II-A-R48 DM-II-A-R100, DM-II-A-R200 |
| Disk Milling-III1 | 25° C., 1 bar, 1.02 | 124 | B on wood chips then milling | No | DM-III1-B |
| Disk Milling-III2 | 25° C., 1 bar, 0.76 | 170 | B on wood chips then milling | No | DM-III2-B |
| Disk Milling-III3 | 25° C., 1 bar, 1.02 | 362 | B on wood chips then milling | No | DM-III3-B |
| Disk Milling-III | 25° C., 1 bar, 0.76 | 19 | C on wood chips then milling | No | DM-III-C |

5% based on duplicate experiments. Detailed description of the size-reduction experiments and the DM-I, DM-II, and DM-III milling processes can be found below.

For hammer milling, spruce wood chips of moisture of about 40% were directly hammer-milled in three successive steps with decreasing screen hole size. The chips were initially processed using a semi-circular screen with 12.7 mm diameter holes (~48% open area). The accepts or undersize particles were then processed with screen hole sizes of 4.8 mm (~37% open area) and 0.8 mm (~18% open area), respectively. The material was allowed to process until the output visually ceased. For disk milling, the single disk refiner operated at 3048 rpm and used D2B-505 plate patterns. In the case of chip milling at 2.4 bar steam pressure (denoted disk milling-I, DM-I), the chips were pre-saturated in a separate 400 L digester in a large 45 oven dry kg batch. The digester was loaded with wood chips and was heated (purged) with steam until the temperature of the digester reached 100° C. Then the digester was vacuumed to about 64 cmHg for over 10 min. Next, about 300 L of water at 78° C. was pulled into the digester to completely cover the chips. This water was held in the digester for 1 min and drained off. The digester was emptied, and the chips were ready for milling. The chip moisture content was increased from 40.2% to 61.3%. During milling, the 5.35 kg (od) saturated chips were allowed to preheat for 3 min at 2.4 bar steam pressure in the feed tube before processing. The disk plate gap was set at 0.254 mm. The chips were processed at about 1 kg (od)/min. The pulp was collected at the time interval of 1-5 min after the feed was started. This is the same time interval over which the electrical energy consumption was calculated. The pulp exited the refiner at 49.0% moisture. For the chips disk-milled at 7.2 bar (disk milling-II, DM-II), no presaturation treatment was applied. The chips were allowed to preheat in the feed tube for 5 min at 7.2 bar prior to feeding to the refiner. The plate gap was set at 0.06 mm. The feed rate was about 1.1 kg (od)/min. Wood chips pretreated by the sulfite process (B and C) were milled under atmospheric conditions (disk milling-III, DM-III) with different disk gaps. Table 16 lists the disk milling experiments along with chip and milling conditions.

The electrical energy consumption of the disk refiner was collected with a digital load monitor system (Ohio Semitronics, Inc., Hilliard, Ohio, model DLM-33-480-1PR). The system displays a resettable energy consumption at the refiner and also records at 1 Hz, via RS-422, to a PC running OSI DLM software, version 1.4 (a Labview executable). The system utilizes two CTX-100-IL current transformer inputs and three voltage inputs. The manufacturer's stated accuracy is ±0.5% for volts, amps, and watts and ±1% for watt hours. The energy consumption (watt hours) was re-set at the local display at the beginning of each run and recorded at the end of each run. This was compared to spreadsheet-calculated energy consumption as a check. This energy consumption was arrived at by integration of the recorded power over the processing period. By spreadsheet calculation of energy consumption, it is possible to collect a sample midway through a run with an associated energy consumption over the corresponding time interval. This removes the startup and ending variability of the runs from the measurements of both fiber quality and energy consumption. Note that this starting/ending effect is small. However, it does take some time to fill the plate gap with material at the start and the feed rate does decrease slightly as the feed chamber empties. Further, small quantities of chips remain in the feed chamber, complicating the energy/mass calculation. Using either energy consumption method, the refiner operating idle energy is collected prior to a run and subtracted from the run time energy over the time period of the run. Finally, the energy consumed is divided by the mass (od) of the fiber collected to give Wh/kg. The refiner electrical energy consumption system was calibrated by the Ohio Semitronics. No obvious drifting or data inconsistency were observed since calibration. This indirect energy determination measured the energy consumption for all the milling processes listed in Table 16.

C. Biomass Fractionation

For hammer milling, the resultant samples was fractionated using three screens of different mesh size into the four fractions R20, R40, R80, and P80. The sieves were from Fischer Scientific Co. (US Standard Sieve series, ASTM specifications). The screen no. 20, 40, and 80 are Tyler equivalent of 20, 35, and 80 mesh. A Ro-Tap sieve shaker (W.S. Tyler Co. Cleveland, Ohio) was used in the process. The device produces about 345 horizontal oscillations/min with a displacement of about 32 mm and generates about 53 hammer raps/min on top of the sieve nest. About 50 g od was used for each batch and the shaker was operated for 15 min. For disk-milled samples, the pulp was fractionated using a Bauer-McNett (TMI, Amityville, N.Y.) wet classifier into six fractions of R14, R28, R48, R100, R200, P200 (R stands for retained on the screen, P for passing the screen). The process follows TAPPI T-233 cm-82 method. The numbers 14, 28, 48, 100, 200 represent the Tyler mesh of the screen used. The R14 fraction was further fractionated using a Pulmac shive analyzer (model MS-B2XLQ, Pulmac Instruments International, Montpelier, Vt.) to separate the fiber bundles (R14Rj) with a screen of slot width 0.1 mm.

D. Chemical Pretreatment

Part of the disk-milled pulp derived at a steam pressure of 7.218 bar (DM-II) was further chemically pretreated (A) using a solution of 7% sodium hydroxide and 12% urea under freezing conditions (−18° C.) for 24 h (Zhao et al., 2008). The liquid to wood ratio was 6:1. The same pretreatment (A) was also applied to wood chips directly prior to producing the unfractionated DM-II-A substrate by disk milling. A process (SPORL) using sulfite to overcome recalcitrance of lignocellulose disclosed in the present invention was applied directly to spruce wood chips. The sodium sulfite and sulfuric acid charges on oven dry wood were 9% and 3.68%, respectively. The liquid to wood chip ratio was 5:1. The pretreatments were conducted at temperature 180° C. (B) and 170° C. (C) for 30 min in rotating autoclave type pulping digesters. The pretreated wood chips were then disk-milled under atmospheric conditions (DM-III). The three pretreatments are used to demonstrate the application of the present external specific surface methodology to realistic hydrolysis scenarios.

E. Fiber Fractionation

Enzymes generally attack the finest particles of a substrate first. The large particles can remain intact even after many hours of hydrolysis. Fiber flocculation occurred when hydrolyzing long-fraction samples, which further affects the enzymatic digestion of the long fraction due to poor mixing. As a result, the measured cellulose conversion is more representative of the fine particles within the substrate, rather than the whole sample. This obscures the actual size effect on cellulose conversion. Therefore, using samples with relatively uniform size (length or width) is desirable to demonstrate the size effect on cellulose conversion. Unfortunately, in disk milling, one cannot avoid producing samples with a dispersed mass distribution over a wide range of fiber length. In addition, these samples have a relatively constant amount of fines of about 15-25% by mass even though the mean (or bulk) lengths of the samples are significantly different. This occurs independent of the operating conditions, such as disk gap and torque. Fines are commonly referred to fiber lengths <0.02 mm in the pulp and paper industry. To address this problem, the inventors fractionated disk-milled samples as described above to reduce the effect of sample size non-uniformity on cellulose conversion. The fractionation provides substrate samples with very different mean sizes even though produced from the same size-reduction process; therefore, the effect of substrate size on hydrolysis yield can be clearly isolated and the proposed external specific surface methodology can be demonstrated. The drawback of this approach is that the inventors were not able to obtain the individual size-reduction energy consumption for these fractionated samples.

F. Two Dimensional Measurements of Substrate using Wet Imaging

The two dimensional characterization of the substrate length and diameter or "width" for most fiber fractions was conducted using a MorFi LB-01 Fiber Analyzer (Techpap, France). The characterization was courteously provided by Integrated Paper Service (IPS, Appleton, Wis.) and Techpap (Norcross, Ga.). The basic principle of the system utilizes optical microscopy and a CCD camera to image fibers in a laminar water flow. The spatial resolution of the image system is 3 μm, sufficient to resolve most fibers in typical samples with a diameter around 20 μm or greater (FIGS. 6A-D). The low sensitivity to very small particles will produce biases to small specific surface. However, the mass fraction of the very small particles (<3 μm) is low in most samples, which alleviates the biases. The MorFi analyzer simultaneously measures the length and diameter of each fiber in a water suspension and flowing in a channel. The oven dry weights of the samples to be analyzed were first determined and used for specific surface calculations. Samples from hammer milling (dry) were first soaked in water under ambient conditions for several hours. During testing, the typical fiber mass concentration of the pulp fed to the system was about 0.3-0.5%. The operator observes the images acquired to determine the optimal fiber mass concentration that avoids too many (causing fiber overlapping) or too few (slowing analysis) fibers. The temperature of the flow channel was controlled at 30° C. (the allowed range is ±5° C. of ambient temperature to avoid fogging of the flow cell glass). Tens of thousands of fibers were measured for each sample to obtain good representation. The system software corrects for fibers cut by the image frame. The MorFi Analyzer has been widely used in the pulp and paper industry for fiber analysis. Guy et al. (2005) compared various wet imaging techniques for measurements of various commercial wood pulps. They found that the relative standard deviations (RSD) in measuring mean length and diameter of a softwood mechanical pulp using a MorFi analyzer were 1.6% and 0.5%, respectively. Assuming that variations in the measured length and width are three times of these respective standard deviations, the inventors estimated the measurement standard deviation in mean volumetric specific surface to be 1.5%.

The hammer-milled fractions, i.e., the HM-R20 and HM-R40, contain many very wide particles that can block the flow cell of the MorFi Analyzer. The substrate length and diameter measurements for these fractions were therefore carried out in-house using traditional optical microscopy. The images were processed by the UTHSCSA ImageTool software (free download at ddsdx.uthscsa.edu/dig/itdesc.html). The software provides the area and perimeter of each individual object in the image. With the assumption that the image objects are rectangular, the width or diameter of the hammer-milled substrate can be found. Triplicate measurements of the R40 sample indicated that the measurement standard deviation in specific surface was 17.4%. The large standard deviation is mainly due to the limited fibers (~150 vs several thousands in MorFi) imaged with the semi-manual data transferring and processing. All measurements were conducted using wet substrate to simulate enzymatic hydrolysis conditions. The comparability between the MorFi and the in-house microscopy measurements was verified by comparing the measured specific surfaces of the HM-R80 sample from both techniques. The difference was found to be about 15%, within the standard deviation of the in-house microscopy technique.

G. Enzymatic Hydrolysis

Enzymatic hydrolysis of the pretreated substrates was carried out according to that described in Example 1.

H. Analytical Methods

Cellulase activity was determined as described in Example 1.

The chemical contents of the different fractions of spruce feedstock and substrates were measured as described in Example 1.

Example 17

Cellulose to Glucose Conversion and Biomass Substrate Specific Surface

Figure 28:
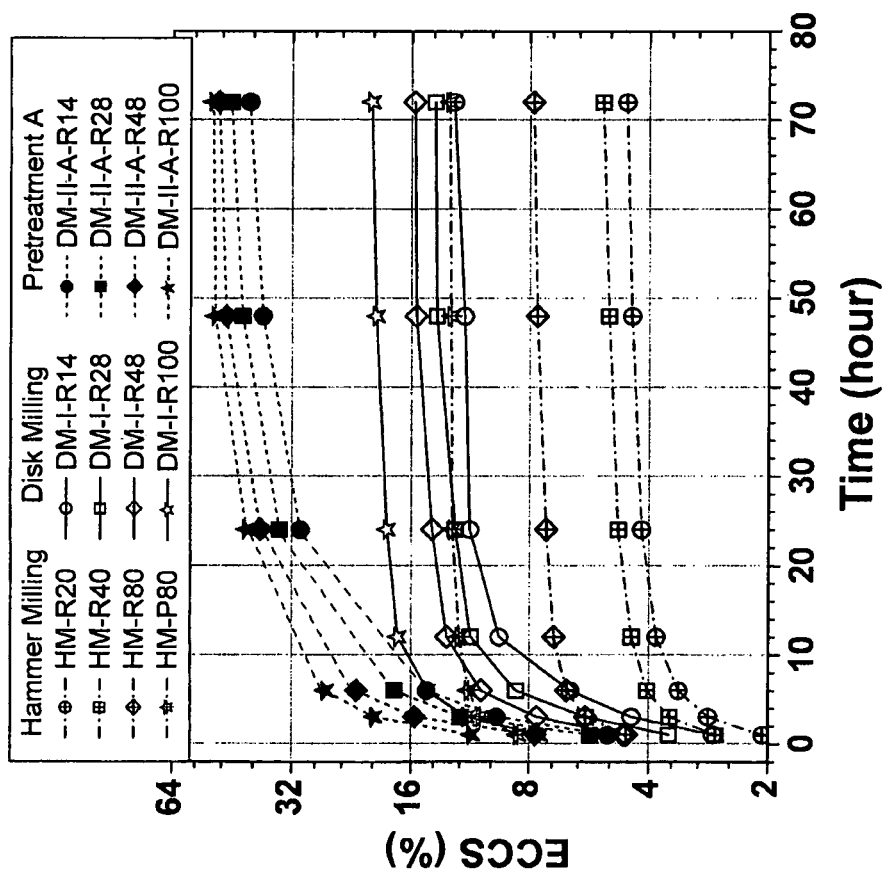
FIG. 28. Time-dependent cellulose conversion efficiencies of disk- and hammer-milled substrates.

Table 17 shows variations in the chemical compositions of the fractionated and three chemically pretreated substrates from disk milling-I (DM-I). The measurement standard deviations of different species were obtained from regular internal quality assurance and quality control. Lignin content of the fractions was measured using the Klason method, i.e., acid-insoluble lignin (Kirk and Obst, 1988; Lai and Sarkanen, 1971). Wood cellulose content is represented by glucan and the rest carbohydrate are hemicelluloses in Table 17. There is a general trend that glucan is more associated with the coarse fractions while lignin is more associated with the fine fractions. However, the variations are very small except for the DM-I-P200 substrate. The measured glucan content of each substrate was used in cellulose conversion calculations. FIG. 28 shows the effect of substrate mesh size on the time-dependent cellulose conversion percentage for disk-milled and hammer-milled substrates. The standard deviation in cellulose conversion was 2% obtained from duplicate hydrolysis experiments. The results clearly show that substrate size affects cellulose conversion. The smaller the mesh size of the substrate, the higher the cellulose conversion. The size effect on cellulose conversion exists even after chemical pretreatment (A) of the substrates. However, when comparing cellulose conversion between the disk-milled (DM-I) and hammer-milled (HM) substrates, smaller mesh size does not correspond to higher cellulose conversion, e.g., HM-R20, HM-R40, HM-R80, have smaller mesh size than DM-I-R14, DM-I-R28, DM-I-R48 but produced significantly lower cellulose conversion than their corresponding disk-milled substrates. As shown in FIG. 27, the specific surfaces of hammer-milled substrates are smaller than the specific surfaces of disk-milled substrates under equivalent mesh sizes. Therefore, comparison of the effect of substrate size on cellulose conversion between the disk and hammer milling cannot be made without considering substrate specific surface.

Figure 29:
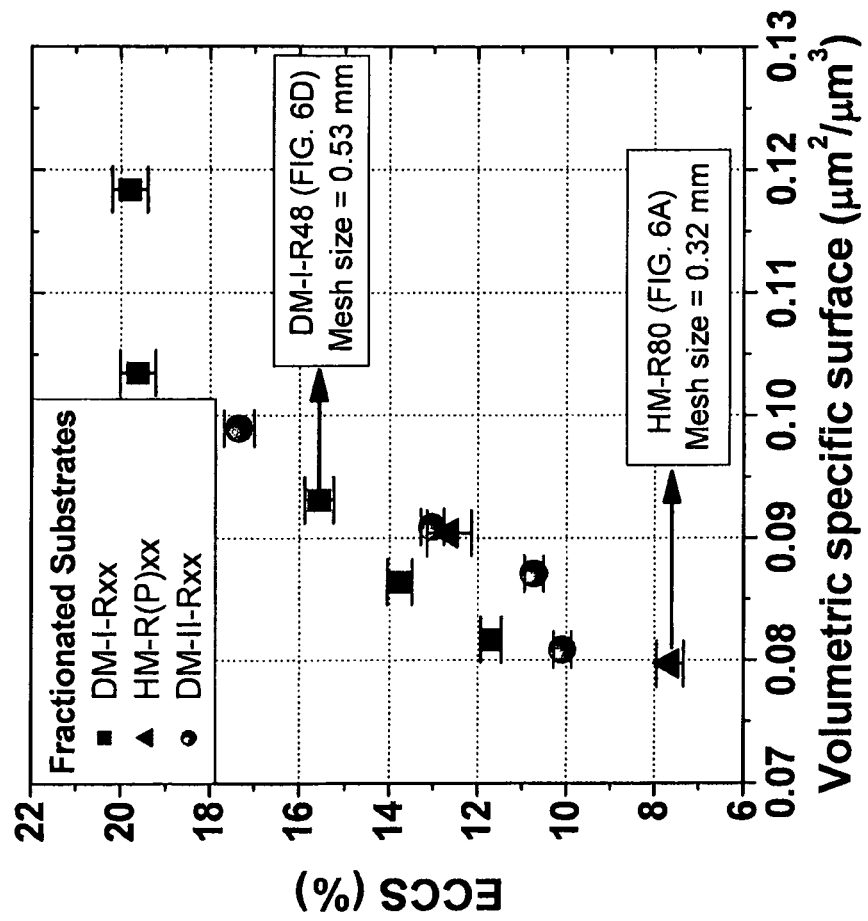
FIG. 29. Comparisons of the effect of volumetric specific surface on cellulose conversion efficiency after 48 h enzymatic hydrolysis among substrates derived from various size-reduction processes.

FIG. 29 shows the cellulose conversion percentages after 48 h of enzymatic hydrolysis as a function of substrate external volumetric specific surface for the untreated substrates. The results clearly show that cellulose conversion percentages increase as substrate external specific surfaces increase for all substrates produced by different size-reduction processes. The results also indicate that DM-I produced higher cellulose conversion percentages than DM-II and hammer milling when comparisons are made under same specific surface. DM-J was a thermomechanical pulping process. More cellulose molecules were exposed on the substrate surface because wood chips were fiberized into individual fibers and fiberization occurred in the S-2 layer with high cellulose content. In DM-II, most wood chips were fiberized into individual fibers and fiberization occurred in the middle lamella (the lignin-rich layer) due to the milling temperature being greater than the glass transition point of lignin; therefore, the substrate was covered with lignin. This can be clearly seen from the color differences between the substrates from DM-I (light) and DM-II (brown). The lignin-covered substrate certainly had lower cellulose conversion efficiency. The data point for the very fine sample DM-I-P200 has completely different chemical composition from those of the rest of the DM-I-Rxx samples (Table 17). The DM-I-P200 contains about 40% more lignin and 33% less glucan than the rest of the DM-I-Rxx samples. Furthermore, this sample has a much larger surface area so that it does not scale well with the rest of the data in graphs.

Hammer milling produced mainly fiber bundles rather than individual fibers even for the HM-R80 fraction (FIG. 6A). As a result, hammer milling is not an efficient size-reduction process to create surface area for enzymatic hydrolysis. FIG. 29 also shows that the cellulose conversion efficiency of a hammer milling produced substrate HM-R80 is lower than that of a disk-milled substrate DM-I-R48, even though the mesh size of HM-R80 is smaller (0.32 mm) than the mesh size of DM-I-R48 (0.53 mm). This clearly indicates that mesh size is not adequate to compare substrates produced from different size reduction processes.

Figure 30:
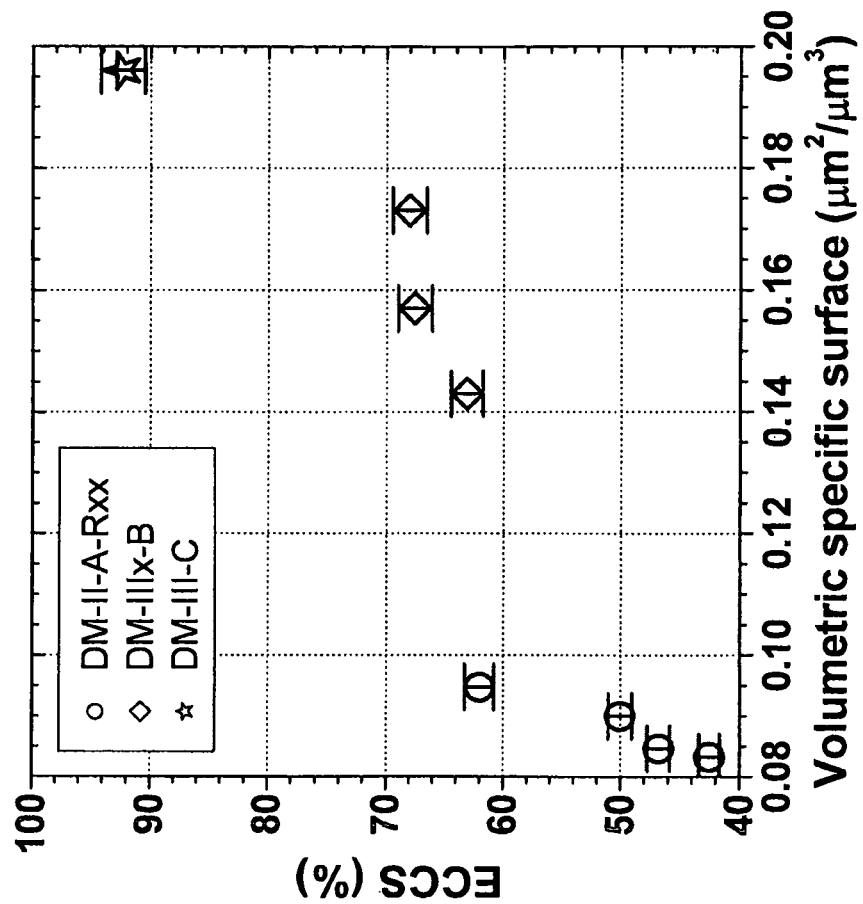
FIG. 30. Comparisons of the effect of volumetric specific surface on cellulose conversion efficiency after 48 h enzymatic hydrolysis among substrates derived from various pretreatment processes.

FIG. 30 shows the effects of three different chemical pretreatments on cellulose conversion with respect to mean substrate volumetric specific surface. The inventors would like to emphasize the term of mean specific surface in the following discussion. The results indicate that the SPORL pretreatment (B) combined with atmospheric disk milling (DM-IIIx, x=1, 2, 3 see Table 1) is more effective than the cold alkaline pretreatment A with high temperature milling (DM-II). The DM-III-C substrate has the highest digestibility, with cellulose conversion over 90%. The effectiveness of SPORL pretreatment C can be seen from the large specific mean surface area and low energy consumption in milling to be discussed later.

FIG. 30 also shows a smaller slope in cellulose conversion vs mean volumetric specific surface for the unfractionated pretreated substrates (DM-IIIx-B) than the slope of the fractionated substrates (DMII-A-Rxx). This suggests that increasing mean specific surface by means of size reduction has a significant effect for the fractionated substrates (DM-II-A) comparing to the unfractionated substrates (DM-IIIx-B). This is because the fractionated substrates have relatively uniform fibers, and therefore the mean specific surface is closer to the individual specific surface of the particles. The effect of enzyme accessibility on cellulose conversion can be effectively characterized using the mean specific surface. As discussed previously, the uniformity in fiber specific surface of the unfractionated substrates is poor. These substrates contain some very small fibers that can be easily digested by the enzymes, in particular the substrates were chemically pretreated. They also contain some very large fibers that can remain intact after many hours of enzymatic digestion. When the increase in the mean specific surface is mainly due to the reduced size of the small fibers and not due to increased mass fraction of the small fibers, the increase in cellulose conversion will be limited.

Figure 31:
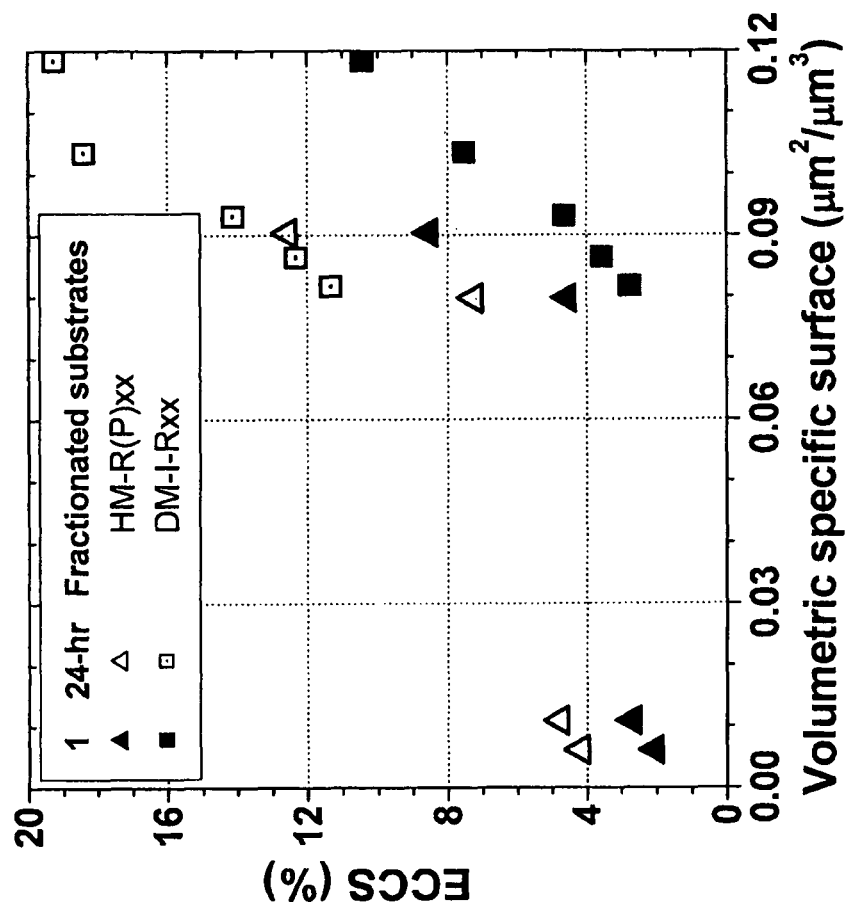
FIG. 31. Comparisons of cellulose conversion efficiency between a set of fractionated disk-milled and a set of fractionated hammer-milled substrates after 1 and 24 h enzymatic hydrolysis.

FIG. 31 shows the comparison of cellulose conversion efficiencies between untreated disk-milled and hammer-milled substrates at two different enzymatic hydrolysis duration times. The results indicate that hammer milling produced a higher cellulose conversion percentage than disk milling at the first hour under same volumetric specific surface. In other words, the initial hydrolysis rates of the hammer milling substrates are faster than those for disk milling. This is probably because many very small particles in a hammer milling substrate were attached to the larger particles of the substrate by static force during dry sieving, as visually observed. The very small particles have a very large specific surface and can be easily digested by the enzymes, which contributed to the high initial hydrolysis rate. In contrast, the disk milling substrates were fractionated by a wet classifier under very dilute fiber concentrations of less than 0.2% at the start, which prevented the attachment of small fractions to the large fraction since wood fibers are hydrophilic. After completing the hydrolysis of the very small particles in certain time period, the hydrolysis of the hammer milling substrates slowed dramatically when compared to the disk milling substrates with the same specific surface, for the reason explained previously. As a result, after 24 h of enzymatic hydrolysis, the percentages of cellulose conversion of the hammer milling substrates are lower than those from the disk milling substrates (FIG. 31). This suggests that enzymes selectively attack easily accessible surfaces—the external surface of small particles in this case. The small particles not only have large specific surfaces but also may have low crystallinity and degree of polymerization from milling. The fast hydrolysis of small particles and their disappearance phenomena due to enzyme digestion agree with that reported by Schell et al. (1989).

TABLE 17

Chemical compositions of the fractionated substrates from the disk milling-I substrates

| | K. Lig. (%) | Arab (%) | Galac (%) | Rham (%) | Glucan (%) | Xylan (%) | Mannan (%) | Sum (%) | Pre-treatment solid yield |
|---|---|---|---|---|---|---|---|---|---|
| Spruce wood | 28.6 | 1.24 | 2.40 | 0.12 | 42.8 | 5.8 | 11.2 | 92.1 | No pre-treatment |
| DM-I-R14 | 26.3 | 0.94 | 1.66 | 0.08 | 46.8 | 5.7 | 12.0 | 93.4 | 100% |
| DM-I-R28 | 26.1 | 0.97 | 1.76 | 0.08 | 46.1 | 5.8 | 11.9 | 92.7 | |
| DM-I-R48 | 27.5 | 1.01 | 1.93 | 0.07 | 45.1 | 6.0 | 11.7 | 93.4 | |
| DM-I-R100 | 27.5 | 1.08 | 2.23 | 0.10 | 44.3 | 6.1 | 11.2 | 92.4 | |

TABLE 17-continued

Chemical compositions of the fractionated substrates from the disk milling-I substrates

| | K. Lig. (%) | Arab (%) | Galac (%) | Rham (%) | Glucan (%) | Xylan (%) | Mannan (%) | Sum (%) | Pre-treatment solid yield |
|---|---|---|---|---|---|---|---|---|---|
| DM-I-R200 | 28.9 | 1.25 | 2.13 | 0.12 | 42.0 | 6.3 | 10.6 | 91.3 | |
| DM-I-P200 | 38.7 | 2.12 | 3.28 | 0.34 | 29.4 | 7.1 | 7.7 | 88.6 | |
| DM-II-A | 31.4 | 1.04 | 1.34 | 0.02 | 47.1 | 5.7 | 6.9 | 93.5 | 85.0% |
| DM-III-B | 29.4 | 0.77 | 1.20 | 0 | 50.8 | 3.1 | 3.6 | 88.9 | 77.0% |
| DM-III-C | 35.4 | 0 | 0 | 0 | 61.5 | 0.65 | 0.3 | 98.9 | 61.8% |
| RSD | 0.8 | 1.6 | 2.9 | 15.9 | 1.0 | 1.4 | 1.4 | | |

Key:
K. Lig.—Klason lignin;
Arab—arabinan;
Galac—galactan;
Rham—rhamnan.

Example 18

Unit Surface Glucose Yield and Biomass Substrate Specific Surface

Figure 32:
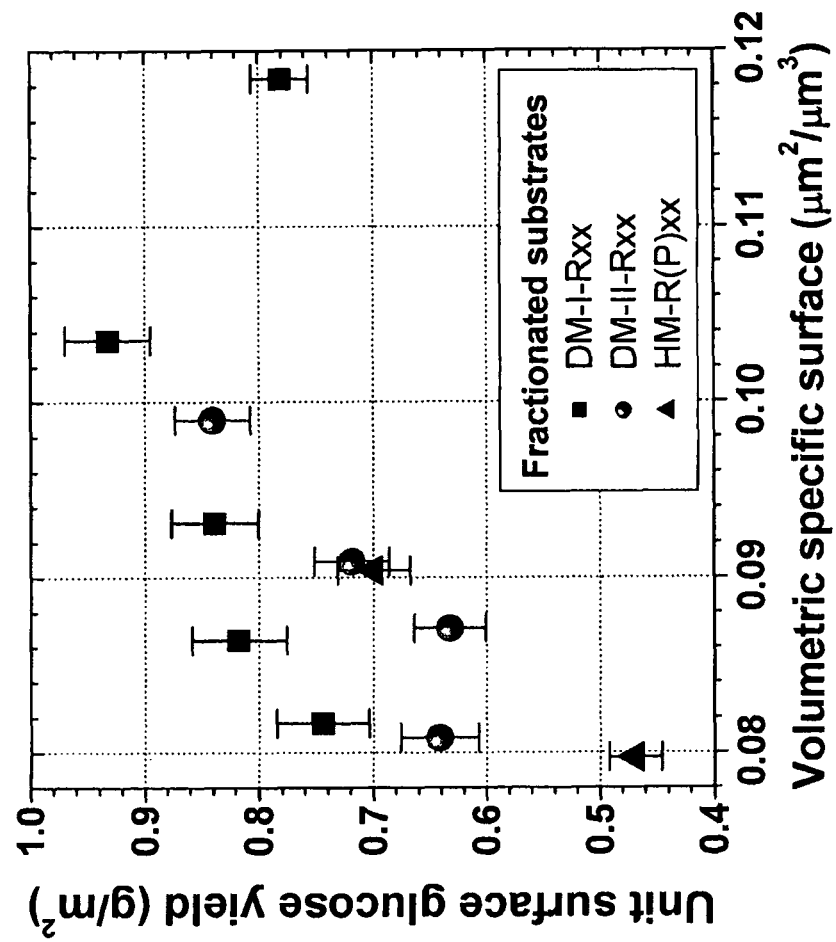
FIG. 32. Comparisons of the effect of substrate volumetric surface on unit surface enzymatic hydrolysis glucose yield (EHGY) among various size-reduction processes.

FIG. 32 shows the EHGY per unit external surface after 48 h of enzymatic hydrolysis as a function of volumetric specific surface. The results indicate that DM-I produced more glucose than hammer milling, and DM-I produced more glucose than DM-II on unit-specific surfaces for the same reasons discussed in the previous section. The inventors also observed an optimal specific surface at which unit surface glucose production reaches a maximal value for untreated DM-I substrates. The product of the x and y coordinate of FIG. 32, the unit substrate volume EHGY (g glucose/cm$^3$ substrate), is the measure of total cellulose conversion per unit volume of wood. The total EHGY, not the unit surface EHGY, may be of the most interest in practice. In other words, the peak unit surface EHGY is not necessarily the economical optimum degree of size reduction. There is a trade off between size reduction and EHGY. Increased specific surface through size reduction may be desirable based on total EHGY, but the benefit of further size reduction past the peak EHGY diminishes.

Example 19

Figure 33:
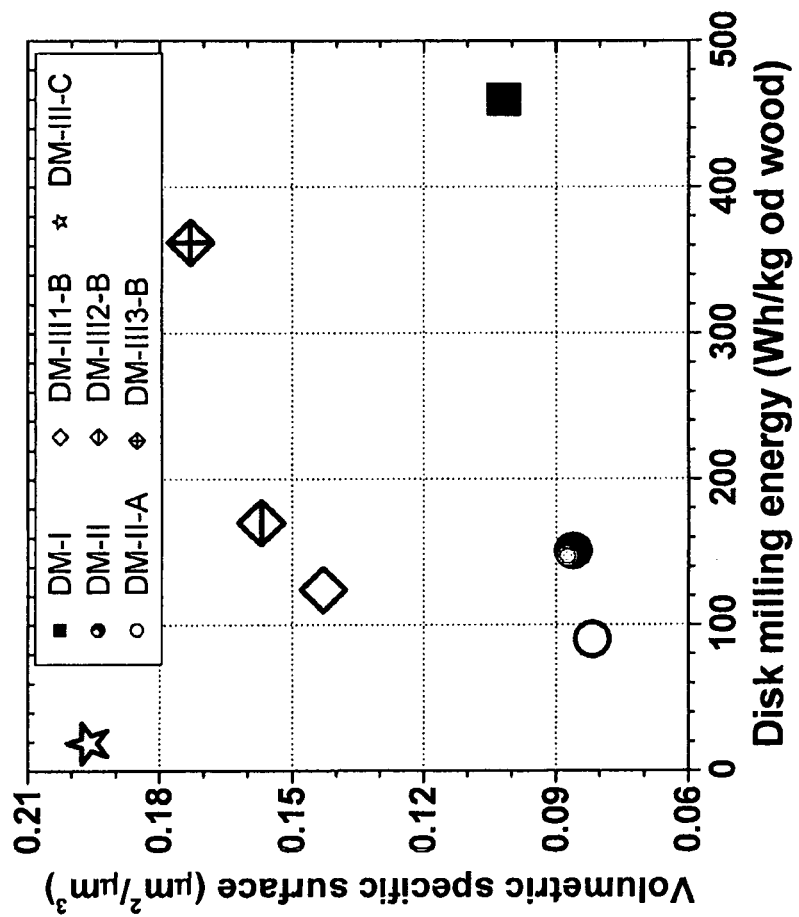
FIG. 33. Effect of chemical pretreatment on disk milling energy consumption and the resultant substrate volumetric specific surface.

Specific Surface Increase, Glucose Yield and Size-Reduction Energy Consumption It is not possible to obtain electric energy consumption on the fractionated samples, as discussed previously. The hammer mill used in the examples was not equipped with an energy measurement device. Therefore, the discussions in the following two examples were focused on the disk-milled whole (unfractionated) pulp samples with the measured size-reduction energy consumption data. FIG. 33 shows the volumetric specific surface of the whole pulp samples and their corresponding electric energy consumption in producing the pulps on unit oven dry kg wood. The specific surface of the wood chips was not measured but very small with respect to the specific surfaces of the fiber samples and can be ignored. Therefore, the y coordinate can be approximated to the specific surface increase through disk milling. The energy data presented in FIG. 33 were on untreated wood mass basis, i.e., corrected for solid yield loss in the pretreatment. The data for the untreated DM-I and DM-II and DM-II-A (treated) substrates seemed to follow the same trend with disk milling energy consumption. The slope of these substrates is 53.2 kg/mWh. The slope for the DM-IIIx-B substrate is 71.6 kg/mWh, greater than the untreated DM-J and DM-II substrates, indicating pretreatment B) increased substrate surface with less energy consumption. Pretreatment C is very effective as DM-III-C falls in the very upper left corner in FIG. 33.

Figure 34:
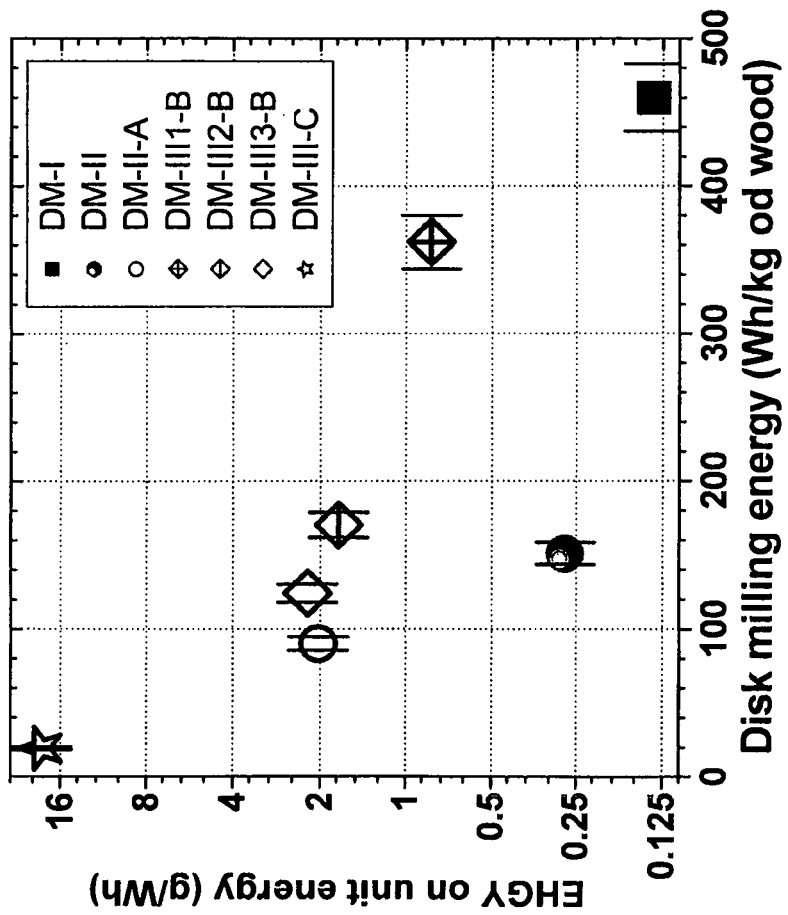
FIG. 34. Comparisons of enzymatic hydrolysis glucose yield (EHGY) per unit energy consumption among various disk milling and pretreatment processes.

FIG. 34 shows the EHGY per watt hour (Wh) energy consumed in mechanical milling after 48 h of enzymatic hydrolysis as a function of milling energy consumption per unit oven dry kg wood for the substrates discussed in FIG. 33. The y coordinate in FIG. 34 is a measure of size-reduction efficiency. The results indicate that DM-II is more efficient than DM-I in terms of size-reduction electric energy consumption. Using more milling energy to increase substrate surface is not effective for the pretreated substrates DM-IIIx-B. Enzymatic cellulose conversion is controlled by the physical and chemical barriers. In this case mechanical size reduction has reached the limit to further remove the physical barrier for effective enzymatic cellulose conversion. Milling conditions significantly affected the energy consumption for pretreated (B) wood chips. Furthermore, the results also indicate that pretreatment significantly improved the EHGY per unit energy consumption. Pretreatment C is the most efficient pretreatment. It not only enhanced the enzyme accessibility to achieve cellulose conversion over 90% (FIG. 30), but it also altered the physical structure of spruce wood to significantly reduce the mechanical milling energy consumption to only 19 kJ/kg oven dry untreated wood. The product of the x and y coordinates is unit wood mass EHGY (g glucose/kg od wood), the same measure of total cellulose conversion discussed above (FIG. 32). The economical degree of size reduction should take not only milling energy consumption but also the total EHGY into consideration.

Example 20

Materials and Methods for Reducing Energy Consumption in Size-Reduction Optimization A. Materials Several Lodgepole Pine trees were harvested from the Pringle Falls Experimental Forest, Deschutes National Forest, Oregan. The logs were debarked and chipped at the US Forest Service, Forest Products Laboratory. The wood chips were screened to remove all particles greater than 38 mm and less than 6 mm in length. The thickness of the accepted chips ranged from 2 to 6 mm.

Commercial enzymes as described in Example 1 were used

Sulfuric acid and sodium bisulfite were used as received from Sigma-Aldrich (St. Louis, Mo., USA).

B. Chemical Pretreatment

When pretreatment is carried out in a separate process, traditional pulping digesters can be used. In the examples discussed below a 23 liter stainless steel digester as described in Example 1 was used The pretreatment with sulfite referred to SPORL in the discussion below is described in the Example 1 of this invention and in a publication by the present inventors (Zhu et al., 2009b). The liquor to wood (oven dry) ratio was 3. The bisulfate charge on oven dry (od) wood solid was 8% and acid charge on wood varied from 0 to 2.21%, which resulted in the pH of the pretreatment solution varying from about 2-5. In hot-water pretreatment, no any chemicals were added. During pretreatment, the temperature was raised to 180° C. and maintained for 30 minutes. Wood chip solid yield was determined from the measured wet weight and moisture content of the collected wood chips. At the end of the pretreatment, the solid was collected and separated from spent liquor and directly transferred to size reduction without washing. An additional post size-reduction solid (fiber or substrate in this case) yield was then determined from the measured wet weight and moisture content of the collected size-reduced fiber solid.

C. Mechanical Size Reduction

Disk milling as described in Example 16 was used to carry out size-reduction of wood in the examples described below. Wood chips were directly fed into the disk refiner. Disk milling was carried out in a laboratory 12-inch disk refiner (Andritz Sprout-Bauer Atmospheric Refiner) under atmospheric conditions but using different process parameters, disk gaps 0.254-1.524 mm, solids content of 3-50%. The batch size of each milling was varied from 0.15 to 1 kg. The size-reduced solid collected was not separately washed, but dewatered through pressing. The dewatering process serves as washing to obtain substrate for enzymatic hydrolysis.

The electrical energy consumption of the disk refiner was collected with a digital load monitor system as described in Example 16. The milling energy consumed is divided by the total oven dry (od) mass of wood chips fed to each batch run to give Wh/kg od fed chips. For pretreated wood chips, this milling energy consumption is multiplied by the wood chip solid yield from pretreatment to obtain size reduction energy consumption based on untreated wood, i.e., Wh/kg od untreated wood. Triplicate repeatability test using pretreated wood chips showed the relative standard deviation in size-reduction energy consumption was only 4%.

D. Enzymatic Hydrolysis

Enzymatic hydrolysis was conducted as described in Example 1.

E. Analytical Methods

Cellulase activity was determined as described in Example 1.

The chemical contents of the original and pretreated biomass were measured as described in Example 1.

Example 21

Figure 35:
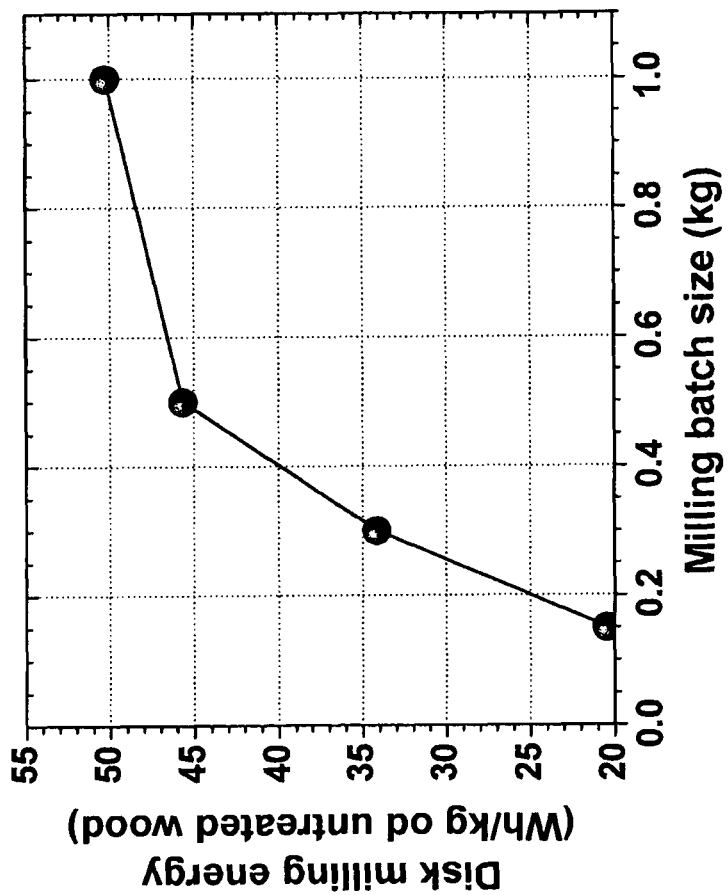
FIG. 35. Effect of the amount of wood chips used in batch disk-milling on measured size-reduction energy consumption. Wood chips were pretreated by SPORL at acid charge of 2.21% (initial pH=1.9). Disk-milling solids-loading was 10% and disk-plate gap was 0.76 mm.

Effect of Chemical Pretreatment on Size-Reduction Energy Consumption and Enzymatic Saccharification Efficiency In batch disk milling, the startup and ending period can affect the measurements of milling energy consumption. A minimum batch size is used to attain stable milling for consistent milling energy measurements. The batch size was varied form 0.15 to 1 kg. It was found that the milling energy increases as batch size increased (FIG. 35). However, the milling energy consumption approached an asymptotic value as batch size was increased over 0.5 kg. Therefore, a milling batch size of 0.5 kg was used in the examples below.

To demonstrate the approach of post-pretreatment size-reduction proposed in the present invention, a dilute acid and two SPORL as described in EXAMPLE 1 in this invention pretreatments were conducted. The pretreated wood chips were then milled at 20% consistency with a disk plate gap of 0.76 mm. The results show that pretreatments reduced milling energy as expected (Table 18). For the SPORL pretreated wood chips at initial pH=1.9, the size-reduction energy consumption was reduced close to 20%. Both SPORL pretreatments on wood chips were found to be very effective in terms of enzymatic cellulose conversion and EHGY. The enzymatic cellulose conversion of substrate (ECCS) were over 92, 96% and EHGY were about 37, and 44% of the total wood for the low pH and high pH SPORL pretreatment, respectively. The lower EHGY for the low pH SPORL pretreatment is due to the loss of about 15% glucan during pretreatment based on carbohydrate analysis (Table 19) However, the high pH SPORL pretreatment reduced size-reduction energy only to about 80%. The acid pretreatment reduced size-reduction energy consumption to about half, but acid pretreatment was not effective for enzymatic cellulose conversion with conversion efficiency of only 41% EHGY was only about 15% of wood. Therefore acid pretreatment is less effective than the low pH SPORL pretreatment in terms of EHGY and size-reduction energy consumption. The performance of the hot-water pretreatment is about the same as that of dilute acid pretreatment in terms of cellulose conversion.

TABLE 18

Effect of chemical pretreatment on size-reduction energy consumption and enzymatic hydrolysis glucose yield (EHGY). Milling solids-loading at 20% with disk plate gap of 0.76 mm

| Pretreatment for 30 min @180° C. | Pretreatment wood chip yield (%) | Milling energy (Wh/kg od untreated wood) | Substrate yield after size-reduction (%) | ECCS @ 48 h (ECCS) (%) | EHGY @48 h (% od wood) |
|---|---|---|---|---|---|
| None | 100.0 | 615.9 | 100 | 12.7 | 5.4 |
| Hot-water | 87.2 | 537.0 | 84.0 | 41.8 | 16.5 |
| Acid, pH = 1.1 | 77.0 | 335.6 | 71.0 | 41.2 | 15.6 |
| SPORL, pH = 4.2 | 86.1 | 499.3 | 78.3 | 96.4 | 44.2 |
| SPORL, pH = 1.9 | 80.7 | 134.5 | 68.1 | 92.2 | 36.8 |

TABLE 19

Weights of wood components after various pretreatment at 180° C. for 30 min.
Sodium bisulfite charge was 8% on od wood for the two SPORL runs. Sulfuric acid charge
was 2.21% (wt/wt) on od wood for the dilute acid and low pH SPORL runs, and 0 for the
hot water and high pH SPORL runs.

| Pretreatment | Initial pH | Final pH | Klason lignin | Arab | Galac | Rham | Glucan | Xylan | Mannan | Sum (g) | Total (g) |
|---|---|---|---|---|---|---|---|---|---|---|---|
| Untreated sample | | | 26.99 | 1.54 | 2.16 | 0.00 | 45.18 | 6.83 | 10.88 | 93.62 | 100 |
| Hot water | 5.0 | 3.3 | 26.72 | 0.32 | 0.53 | 0.00 | 44.78 | 3.48 | 3.27 | 79.10 | 84.0 |
| Dilute acid | 1.1 | 1.5 | 26.40 | 0 | 0 | 0 | 37.67 | 0.40 | 0.20 | 64.13 | 71.4 |
| SPROL | 4.2 | 2.5 | 24.29 | 0 | 0 | 0 | 44.56 | 1.79 | 0.91 | 71.56 | 76.9 |
| SPORL | 1.9 | 1.5 | 24.92 | 0 | 0 | 0 | 38.33 | 0.29 | 0.26 | 63.91 | 66.7 |
| RSTD (%) | | | 0.80 | 1.60 | 2.90 | 15.90 | 1.00 | 1.40 | 1.40 | | |

Example 22

Effect of Wood Chip Solids-Loading on Size-Reduction Energy Consumption and Enzymatic Saccharification Efficiency For enzymatic saccharification applications, the requirements for the final fibers are very different from and much less restricted than those for papermaking. This provides opportunities for reducing energy consumption in wood chip disk milling by adjusting various milling conditions. This example demonstrates the effect of wood chip solids-loading on size-reduction energy consumption. For the untreated wood chips, size-reduction energy consumption was over 800 Wh/kg od wood chip when the wood chips from chipping were directly milled with moisture content of 50% (Table 20). Adding water in milling reduced the solids-loading during milling, which resulted in reduction in milling energy consumption as shown in Table 20. The size-reduction energy consumption was reduced by 34% when solids-loading was reduced to 10% from 50%. The lower size-reduction energy consumption did not reduce enzymatic hydrolysis cellulose conversion (FIG. 36) and EHGYs from the milled substrates. The EHGYs remained relatively unchanged when milling solids-loading was varied from 10-50%. A slight increase in EHGY was obtained from the substrate milled at the lowest solids-loading (Table 20).

TABLE 20

Effect of milling wood solids-loading on milling energy consumption
and enzymatic hydrolysis glucose yield (EHGY).

| Milling wood solids-loading (%) | Milling energy (Wh/kg od wood) | EHGY @48 h (% od wood) |
|---|---|---|
| 10 | 562.9 | 7.1 |
| 20 | 615.9 | 5.3 |
| 30 | 699.3 | 6.0 |
| 50 | 858.4 | 5.2 |

Lodgepole pine wood chips were untreated. Disk plate gap = 0.76 mm

Figure 36:
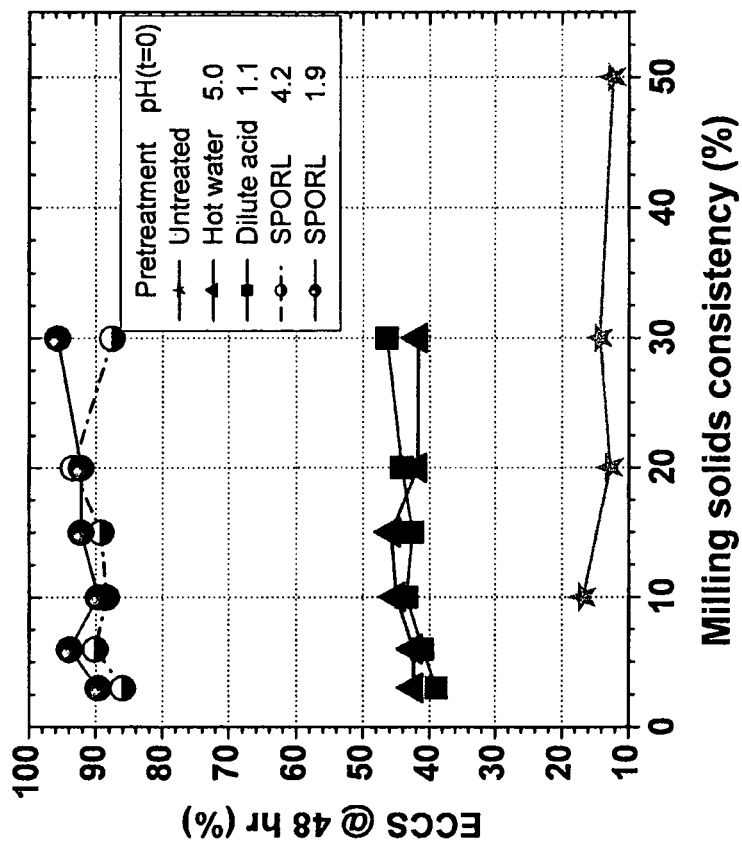
FIG. 36. Effects of solids-loading during disk-milling on enzymatic hydrolysis cellulose conversion of substrates (ECCS) produced by four different pretreatment processes. Disk plate gap in milling was 0.76 mm.

When the low-solids-loading milling was applied to pretreated wood chips, the effect of size-reduction energy consumption was much more significant. For wood chips pretreated by low pH SPORL, the feedstock size-reduction energy consumption was reduced by a factor of 15 when solids-loading was reduced from 30% to 3% (Table 21 and FIG. 37). The combined effect of pretreatment and low solids-loading can reduce size-reduction energy consumption to a very reasonable level, i.e., less than 100 Wh/kg od wood, at solids-loading about 15-20%, and less than 50 Wh/kg od wood at solids-loading less than 10%. Typical milling energy consumption in size-reduction of agriculture residual is about 50 Wh/kg od feedstock (Cadoche and Lopez, 1989). Therefore, the present invention can achieve equivalent level of energy consumption for woody biomass to those for agricultural residual. This will significantly improve the economics of woody biomass conversion. Furthermore, the enzymatic hydrolysis cellulose conversion was not affected or remained at above 90% by the solids-loading in disk milling (FIG. 36). EHGYs were between 33-38% of wood (Table 21).

TABLE 21

Effect of milling wood solids-loading on milling energy consumption
and enzymatic hydrolysis glucose yield (EHGY) for pretreated wood
chip by a SPORL process at initial pH = 1.9.

| Milling wood solids-loading (%) | Milling Energy (Wh/kg od wood) | Substrate yield after size-reduction (%) | EHGY @48 h (% od wood) |
|---|---|---|---|
| 3 | 10.0 | 66.9 | 36.8 |
| 6 | 15.7 | 65.0 | 34.5 |
| 10 | 45.8 | 67.9 | 36.0 |
| 15 | 71.9 | 65.3 | 33.6 |
| 20 | 134.5 | 68.1 | 36.8 |
| 30 | 152.6 | 67.8 | 34.9 |

Wood chip yield from pretreatment = 80.7%. Disk milling plate gap = 0.76 mm.

Figure 37:
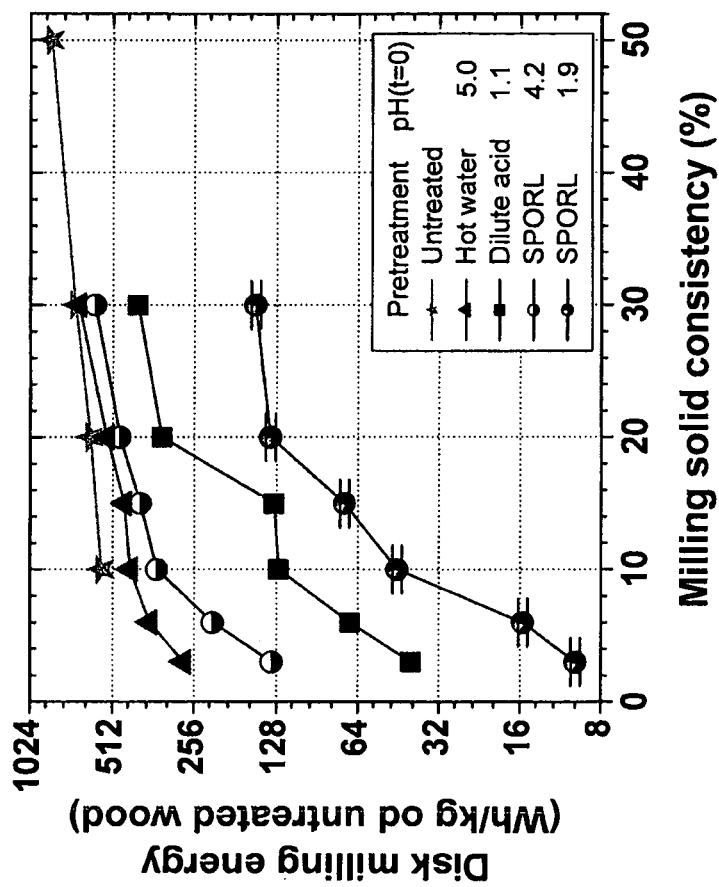
FIG. 37. Effects of solids-loading during disk-milling on size-reduction energy consumption. Disk-plate gap in milling was 0.76 mm.

Savings in size-reduction energy consumption were also achieved for wood chips pretreated by high pH SPORL and dilute acid process (FIG. 37). However the amount of savings varies with pretreatment process. For example, about a factor of 5 and 10 reductions in energy was realized for wood chips pretreated by high pH SPORL and dilute acid, respectively, when milling solids loadings was reduced from 30% to 3%. The low energy consumption millings using low solids-loading did not affect enzymatic cellulose conversion (FIG. 36) for wood chips pretreated by both the high pH SPORL and dilute acid. Enzymatic cellulose conversions were all over 90% for substrates produced by high pH SPORL at low-solids loading millings (FIG. 36). As is well known, dilute acid pretreatment is not highly effective for removing softwood recalcitrance, and cellulose conversion was less than 50% (FIG. 36) with EHGY of about 15% of od wood (Table 22). By comparing acid pretreatment (Table 22) to SPORL low pH pretreatment (Table 21), one can find that acid pretreatment is not as effective as the low pH SPORL pretreatment in terms of not only EHGY, but also reducing size-reduction energy consumption (FIGS. 36 and 37).

TABLE 22

Effect of milling wood solids-loading on milling energy consumption and enzymatic hydrolysis glucose yield (EHGY) for pretreated wood chip by a dilute acid pretreatment with initial pH = 1.1.

| Milling wood solids-loading (%) | Milling energy (Wh/kg od wood) | Substrate yield after size-reduction (%) | EHGY @48 h (% od wood) |
|---|---|---|---|
| 3 | 40.7 | 72.8 | 16.8 |
| 6 | 68.4 | 72.4 | 15.9 |
| 10 | 125.4 | 72.2 | 15.2 |
| 15 | 130.4 | 70.7 | 15.3 |
| 20 | 335.6 | 71.0 | 14.5 |
| 30 | 412.5 | 69.4 | 13.5 |

Wood chip yield from pretreatment = 77.0%. Disk milling plate gap = 0.76 mm.

Example 23

Effect of Disk Plate Gap on Size-Reduction Energy Consumption and Enzymatic Saccharification Efficiency Milling disk plate gap is another milling process parameter that can be adjusted to reduce size-reduction energy consumption. For the SPORL pretreated wood chips at initial pH=1.9, an increasing disk plate gap in milling from 0.38 mm to 1.5 mm, size-reduction energy consumption can be reduced by a factor of 3 (Table 23 and FIG. 38). The increased disk gap did not affect EHGY as clearly shown in Table 23 and FIG. 39. This suggests a disk plate gap large than 1.5 mm can be used for reducing energy consumption in feedstock size reduction. The limit of the largest gap without affecting cellulose conversion often depends on pretreatment conditions.

Figure 38:
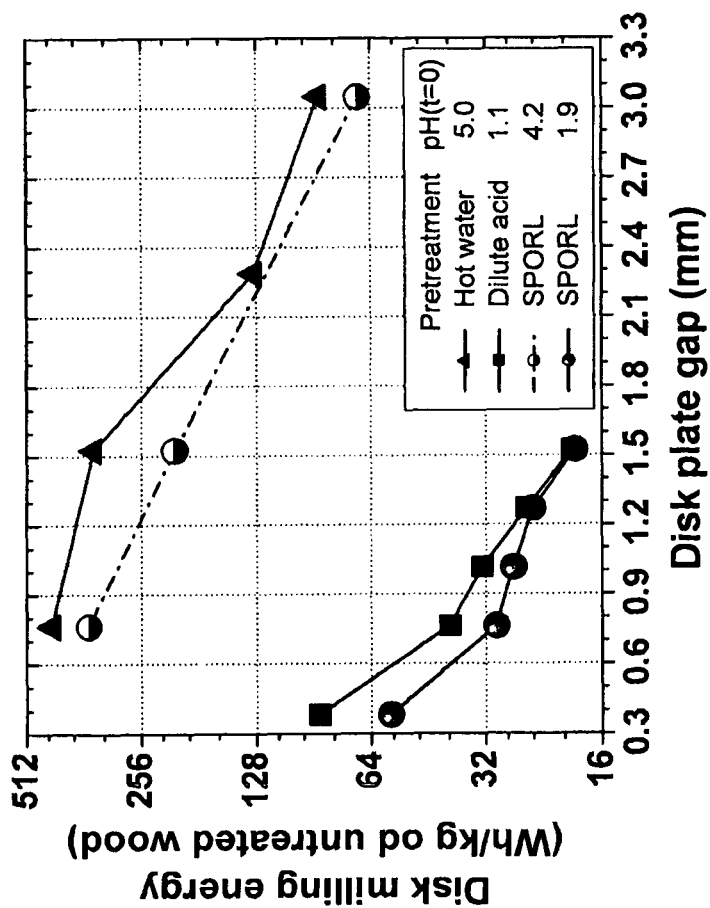
FIG. 38. Effects of disk-plate gap during disk milling on size-reduction energy consumption. Solids-loading in milling was 10%.
Figure 39:
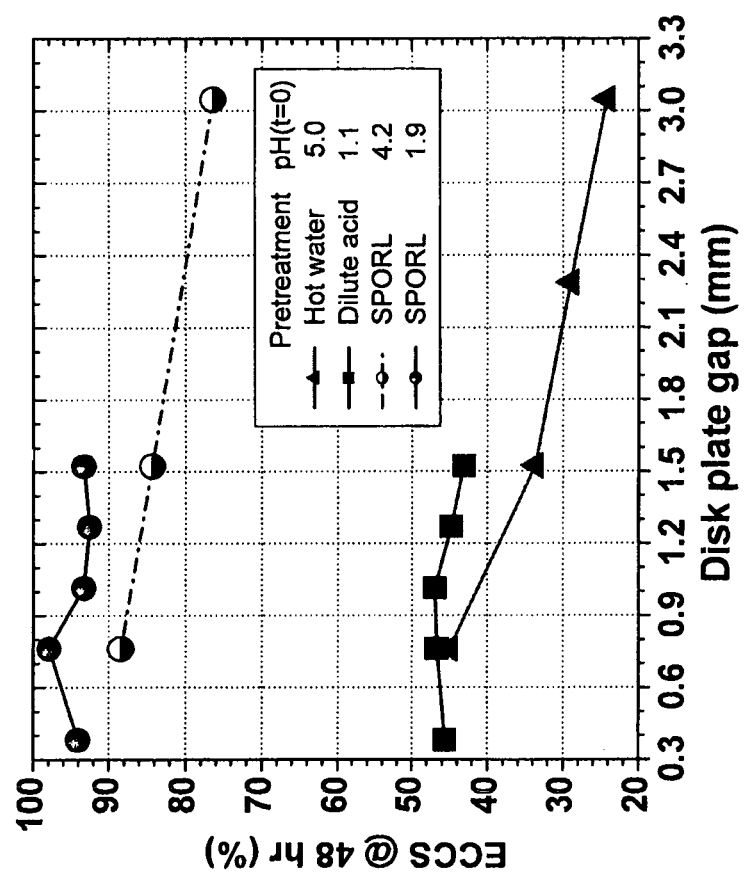
FIG. 39. Effects of disk-plate gap on enzymatic hydrolysis cellulose conversion of substrates (ECCS) produced by four different pretreatment processes. Solids-loading in milling was 10%.

Similar results in energy savings were obtained for dilute acid (Table 24 and FIG. 38), hot-water pretreated wood chips (FIG. 38). However, the dilute acid and hot-water pretreatments were not as effective as the SPORL low pH pretreatment in reducing size-reduction energy consumption and improve EHGY. Size-reduction energy consumption for milling the acid pretreated wood chips was higher than that used for milling the SPORL pretreated wood chips under the same milling disk gaps, but cellulose conversion of acid pretreated substrate was only about 40% of that achieved from the SPORL pretreated substrate. The hot-water pretreatment only achieved a maximum of 40% cellulose conversion but consumed more than 10 times size-reduction energy used by low pH SPORL under the similar milling disk gaps (FIGS. 38 and 39).

TABLE 23

Effect of disk milling plate gap on milling energy consumption and enzymatic hydrolysis glucose yield (EHGY) for pretreated wood chip by a SPORL process at initial pH = 1.9.

| Plate Gap (mm) | Milling energy (Wh/kg od wood) | Substrate yield after size-reduction (%) | EHGY @48 h (% od wood) |
|---|---|---|---|
| 0.381 | 56.81 | 67.2 | 41.0 |
| 0.762 | 30.02 | 67.9 | 43.1 |
| 1.016 | 27.07 | 67.4 | 40.8 |
| 1.27 | 24.13 | 67.6 | 40.6 |
| 1.524 | 18.79 | 68.0 | 41.1 |

Wood chip yield from pretreatment = 80.7%. Disk milling solids-loading = 10%

TABLE 24

Effect of disk milling plate gap on milling energy consumption and enzymatic hydrolysis glucose yield (EHGY) for pretreated wood chip by a dilute acid pretreatment at initial pH = 1.1.

| Plate Gap (mm) | Milling energy (Wh/kg od wood) | Substrate yield after size-reduction (%) | EHGY @48 h (% od wood) |
|---|---|---|---|
| 0.381 | 87.27 | 71.8 | 16.3 |
| 0.762 | 39.74 | 72.2 | 16.8 |
| 1.016 | 32.66 | 72.0 | 16.8 |
| 1.27 | 24.98 | 72.5 | 16.1 |
| 1.524 | 19.11 | 72.9 | 15.6 |

Wood chip yield from pretreatment = 77%. Disk milling solids-loading = 10%

Since the high pH SPORL pretreatment (initial pH=4.2) produced highest EHGY (Table 18) and less fermentation inhibitors as discussed in Example 13. Furthermore, it is always desirable to use less acid in pretreatment to reduce chemical costs, equipment corrosion, and improve operation safety. The inventors used large disk plate gap to bring down the size-reduction energy consumption for chips from SPORL high pH runs (Table 25). The disk plate gasp were varied from 0.76 mm to 3 mm. It was found that the gap can be opened to 1.5 mm without affect EHGY. EHGY decreased by about 10% to 40.1 wt % wood when the disk gap was further opened to about 3 mm. It should be pointed out that EHGY of 40 wt % wood is considered very high. The size-reduction energy was reduced from 335 Wh/kg od wood to about 69 Wh/kg od wood when the disk gap is opened form 0.76 mm to about 3 mm with only about 10% reduction in EHGY. In general, enzymatic cellulose conversion efficiency decreased linearly with the increase in disk plate gap for wood chips pretreated by high pH SPORL (initial pH=4.2) as shown in FIG. 39. So, optimization is possible when integrate EHGY and size-reduction energy consumption.

TABLE 25

Effect of disk milling plate gap on milling energy consumption and enzymatic hydrolysis glucose yield (EHGY) for pretreated wood chip by a SPORL process at initial pH = 4.2.

| Plate Gap (mm) | Milling energy (Wh/kg od wood) | Substrate yield after size-reduction (%) | EHGY @48 h (% od wood) |
|---|---|---|---|
| 0.762 (Run 1) | 366.2 | 78.3 | 44.2 |
| 0.762 | 335.4 | 77.8 | 41.2 |
| 1.524 | 208.8 | 77.8 | 40.1 |
| 3.048 | 69.1 | 77.8 | 36.6 |

Wood chip yield from pretreatment = 86.1%. Disk milling solids-loading = 10%

All of the products and/or methods disclosed and claimed herein can be made and executed without undue experimentation in light of the present disclosure. While the products and methods of this invention have been described in terms of particular embodiments, it will be apparent to those of skill in the art that variations may be applied to the products and/or methods in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

V. References

The following references, to the extent that they provide exemplary procedural or other details supplementary to those set forth herein, are specifically incorporated herein by reference:

U.S. Pat. No. 2,924,547
U.S. Pat. No. 3,808,090
U.S. Pat. No. 3,998,688
U.S. Pat. No. 4,461,648
U.S. Pat. No. 4,767,499
U.S. Pat. No. 5,916,780
U.S. Pat. No. 7,182,836
Alami et al., In: *Canadian Pulp and Paper Association*, Proc. 1995 Int. Mechanical Pulping Conference, Ottawa, Montreal, 203-211, 1995.
Allen et al., *Ind. Eng. Chem. Res.*, 40:2352-2361, 2001.
Ballesteros et al., *Applied Biochem. Biotechnol.*, 84-86:97-110, 2000.
Bryce, In: *Pulping, Pulp and Paper Chemistry and Chemical Technology*, 3$^{rd}$ Ed., 1(4):291-376, Casey (Ed.), John Wiley & Sons, NY, 1980.
Cadoche and Lopez, *Biological Wastes*, 30:153-157, 1989.
Chum et al., *Applied Biochem. Biotechnol.*, 24/25:1-14, 1990.
Chundawat et al., *Biotechnol. Bioengine.*, 96:219-231, 2007.
Cullis et al. *Biotechnol. Bioengineer.*, 85(4):413-421, 2004.
Dasari and Berson, *Applied Biochem. Biotech.*, 137:289-299, 2007.
Davis, *J. Wood Chem. Technol.*, 18:235-252, 1998.
De Bari et al., *Ind. Eng. Che. Res.*, 46:7711-7720, 2007.
Eggeman and Elander, *Bioresour. Technol.*, 96(18):2019-2025, 2005.
Emmel et al., *Bioresource Technol.*, 86(2):105-115, 2003.
Excoffer et al., *Biotechnolo. Bioeng.*, 38:1308-1317, 1991.
Galbe and Zacchi, *Appl. Microbiol. Biotech.*, 59(6):618-628, 2002.
Guy et al. In: *Comparison of Fiber Length Analyzers*, Proc. 2005 TAPPI Papermakers Conf., Milwaukee, Wis., 2005.
Hall and Stockman, In: *Sulfitkokning vid Olika Aciditet*, Svensk Papperstidn., 61:871, 1958.
Heitz et al., *Biotech. Bioeng.*, 35:23-32, 1991.
Heuser, In: *Trends in Fundamental Research in the Cellulose and Wood Pulp Field*, TAPPI, 33(3):118, 1950.
Himmel et al., *Science*, 315:804-807, 2007.
Hinman et al., *Appl. Biochem. Biotech.*, 34-35:639-649, 1992.
Holtzapple et al., *Biotech. Bioeng.*, 33:207-210, 1989.
Hoque et al., In: *Review and analysis of performance and productivity of size equipment for fibrous materials*, ASABE Annual International Meeting, Minneappolis, Minn., 2007.
Ingruber, In: *Sulfite Science and Technology*, Ingruber et al. (Eds.), Joint Textbook Committee of the Paper Industry, TAPPI and CPPA., 3$^{rd}$ Ed., 3-23, 1985.
Irvine, *Wood Science and Technology*, 19:139-149, 1985.
Janson and Sjostrom, In: *Behaviour of Xylan During Sulphite Cooking of Birchwood*, Svensk Papperstidn., 67:764, 1964.
Jeoh et al., *Biotechnol. Bioeng.*, 98(1):112-122, 2007.
Kenealy et al., *Holzforschung*, 61:223-229, 2007.
Kirk and Obst, *Lignin Determination. Methods Enzymol.*, 161:65-73, 1988.
Kurdin, In: *Pulping, Pulp and Paper Chemistry and Chemical Technology*, 3$^{rd}$ Ed. 1(4): 197-252, Casey (Ed.), John Wiley & Sons, NY, 1980.
Lai and Sarkanen, In: *Lignins: Occurane, Formation, Structure and Reactions*, Sarkanen and Ludwig (Eds.), Wiley-Interscience, NY, 1971.
Larsson et al., *Enzyme Microbial. Tech.*, 24:151-159, 1999.
Laureano-Perez et al., *Appl. Biochem. Biotech.*, 121:1081-1099, 2005.
Lefebvre, In: *Atomization and Sprays*, Hemisphere Publishing Corp., NY, p 91, 1989.
Levenspiel, In: *Chemical Reaction Engineering*, NY, John Wiley and Sons. 460-477, 1972.
Lynd, *Ann. Rev. Energy and the Environment*, 21:403-465, 1996.
Mabee et al., *Appl. Biochem. Biotech.*, 129-132:5570, 2006.
Mani et al., *Biomass and Bioenergy*, 27:339-352, 2004.
Manisfield et al., *Biotech. Progress*, 15:804-816, 1999.
Marteny, In: Pulping, Pulp and Paper Chemistry and Chemical Technology, 3$^{rd}$ Ed., Casey (Ed.), John Wiley & Sons, NY, 1(4):252-291, 1980.
Meier, In: *On the behaviour of Wood Hemcelluloses under Different Pulping Conditions, Part I and II*, Svensk Papperstidn., 65(8):299; 65(16):589, 1962
Mooney et al. *Enzyme and Microbial Technol.*, 25:644-650, 1999.
Mosier et al., *Bioresource Tech.*, 96(6):673-686, 2005.
Nguyen et al., *Appl. Biochem. Biotech.*, 84-86:561-576, 2000.
Pan et al., *Biotech. and Bioengin.*, 90(4):473-481, 2005.
Pan et al., *Biotech. and Bioengin.*, 94(5):851-861, 2006.
Pfister and Sjostrom, In: *The Formation of Monosaccharides and Aldonic and Uronic Acids during Sulphite Cooking*, Paperi Puu, 59(11):711, 1977.
Reineke, *J. Appl. Physiol.*, 16:944-946, 1961.
Rivers and Emert, *Biotechnology Letters*, 9(5):365-368, 1987.
Salmen et al., In: *Mechanical Pulping*, Sundholm (Ed.)., Finland, 35-65, 1999.
Sangseethong et al., *J. Food Biochem.*, 22:321-330, 1998.
Schell and Harwood, *Appl. Biochem. Biotech.*, 45/46, 1994.
Schell et al. *Biotechnology Letters*, 11(10):745-748, 1989.
Sowa, *Atomization and Sprays*, 2(1):1-15, 1992.
Stenberg et al., *Biotechnol Bioeng.*, 68(2):204-10, 2000.
Sun and Cheng, *Bioresource Technol*, 83(1):1-11, 2002.
Sundman, In: *Sockerutlosningen vid Sulfitcellulosakoket*, Paperi Puu, 32(9):267, 1950.
Thompson and Kaustinen, In: *A Study of Certain Carbohydrate Degradations during Sulfite Pulping*, TAPPI, 49(12): 550, 1966.
Tillman et al., *Applied Biochem. Biotechnol.*, 20-21:107-117, 1989.
Tillman et al., *Applied Biochem. Biotechnol.*, 24-25:103-113, 1990.
Wingren et al., *Biotechnol. Prog.*, 19:1109-1117, 2003.
Wood and Bhat, *Methods Enzymol: Biomass, Part A: Cellulose and Hemicellulose*, 160:87-112, 1988.
Yang and Wyman, *Biotech. and Bioengin.*, 86(1):88-95, 2004.
Yorston, In: *Studies in Sulphite Pulping*, Dominion For. Serv. Bull., No 97, Ottawa, Canada, 56, 1942.
Zhao et al., *Biotechnol. Bioengineer.*, 99(6):1320-1328, 2008.
Zhu et al., Wood and Fiber Sci., 39:502-512, 2007.
Zhu et al., *Appl. Biochem. Biotech.*, 121-124:1045-1054, 2005.
Zhu et al., *Chem. Eng. Sci.*, 64(3):474-485, 2009a.
Zhu et al., *Bioresource Technology*, 2009b, (in press)

What is claimed:

1. A method for treating a cellulose-containing material to produce sugars comprising the steps of:
   (a) providing cellulose-containing woody biomass comprising hemicellulose and lignin;
   (b) treating the woody biomass of step (a) for 0.1 to 120 minutes with a solution comprising a base of sulfite or bisulfite adjusted to have an initial pH of from about 1.5 to 5.0, wherein said treating is at a temperature of about 150 to 250° C., wherein sulfite or bisulfite charge (w/w), based on oven dried woody biomass, is no more than 9%, but greater than 0, and wherein treating removes hemicellulose and produces only partial delignification; and
   (c) enzymatically hydrolyzing the resultant treated biomass of step (b) to produce sugars,
   wherein the woody biomass is mechanically size-reduced or treated by steam explosion prior to or during step (a) or (b).

2. The method of claim 1, wherein the temperature of step (b) is about 150 to 220° C.

3. The method of claim 1, wherein the sulfite or bisulfite base further comprises sulfur dioxide.

4. The method of claim 1, wherein the mass ratio between the sulfite or bisulfite base and the woody biomass in step (b) is about 1:100 to about 1:10.

5. The method of claim 1, wherein the bisulfite is sodium bisulfite, magnesium bisulfite, ammonium bisulfite, calcium bisulfite, or potassium bisulfite.

6. The method of claim 1, wherein the mechanical size reduction comprises disk milling or hammer milling.

7. The method of claim 1, wherein step (b) takes place in a feeder coupled to a device used for the mechanical size reduction.

8. The method of claim 1, wherein the method comprises treating the woody biomass with steam explosion at the same time as step (b).

9. The method of claim 1, where the method further comprises fermenting the sugars into ethanol.

10. The method of claim 1, wherein the method further comprises chemically converting the sugars to a biofuel or a biochemical.

11. The method of claim 1, wherein the biomass ratio between the sulfite or bisulfite base and the woody biomass in step (b) is about 1:40 to about 1:15.

* * * * *